United States Patent
Shuttleworth et al.

(10) Patent No.: US 9,676,765 B2
(45) Date of Patent: Jun. 13, 2017

(54) HISTONE DEACETYLASE INHIBITORS AND THEIR USE IN THERAPY

(71) Applicant: Karus Therapeutics Limited, Oxfordshire (GB)

(72) Inventors: Stephen J. Shuttleworth, Oxfordshire (GB); Cyrille D. Tomassi, Oxfordshire (GB); Alexander R. Cecil, Oxfordshire (GB); Somhairle Maccormick, Oxfordshire (GB); William J. Nodes, Oxfordshire (GB); Franck A. Silva, Oxfordshire (GB)

(73) Assignee: Karus Therapeutics Limited, Oxfordshire (GB)

( * ) Notice: Subject to any disclaimer, the term of this patent is extended or adjusted under 35 U.S.C. 154(b) by 0 days.

(21) Appl. No.: 14/441,401

(22) PCT Filed: Nov. 6, 2013

(86) PCT No.: PCT/GB2013/052917
§ 371 (c)(1),
(2) Date: May 7, 2015

(87) PCT Pub. No.: WO2014/072714
PCT Pub. Date: May 15, 2014

(65) Prior Publication Data
US 2015/0361074 A1   Dec. 17, 2015

(30) Foreign Application Priority Data

Nov. 7, 2012 (GB) .................................. 1220029.1
May 20, 2013 (GB) .................................. 1309015.4
Aug. 28, 2013 (GB) .................................. 1315254.1

(51) Int. Cl.
| | | |
|---|---|---|
| *A61K 31/4439* | (2006.01) | |
| *C07D 413/12* | (2006.01) | |
| *C07D 417/12* | (2006.01) | |
| *A61K 45/06* | (2006.01) | |
| *C07D 401/12* | (2006.01) | |

(52) U.S. Cl.
CPC ........ *C07D 417/12* (2013.01); *A61K 31/4439* (2013.01); *A61K 45/06* (2013.01); *C07D 401/12* (2013.01); *C07D 413/12* (2013.01)

(58) Field of Classification Search
CPC .. C07D 413/12; C07D 401/12; C07D 417/12; A61K 31/4439; A61K 45/06
USPC ..................................................... 546/268.1
See application file for complete search history.

(56) References Cited

U.S. PATENT DOCUMENTS

| | | |
|---|---|---|
| 4,017,500 A | 4/1977 | Mayer et al. |
| 7,022,840 B2 | 4/2006 | Kobuke et al. |
| 8,748,458 B2 | 6/2014 | Shuttleworth et al. |
| 9,200,007 B2 | 12/2015 | Shuttleworth et al. |
| 9,266,879 B2 | 2/2016 | Shuttleworth et al. |
| 9,340,503 B2 * | 5/2016 | Shuttleworth ....... C07D 213/55 514/312 |
| 2002/0099210 A1 | 7/2002 | Alexander et al. |
| 2002/0151544 A1 | 10/2002 | Hayakawa et al. |
| 2004/0106787 A1 | 6/2004 | Kobuke et al. |
| 2004/0235888 A1 | 11/2004 | Yamamori et al. |
| 2007/0135466 A1 | 6/2007 | Ledeboer et al. |
| 2008/0125440 A1 | 5/2008 | Cai et al. |
| 2008/0207729 A1 * | 8/2008 | Pisano ................. C07D 209/18 514/415 |
| 2008/0221112 A1 | 9/2008 | Yamamori et al. |
| 2011/0201608 A1 | 8/2011 | Hoffmann et al. |
| 2011/0305729 A1 | 12/2011 | Shuttleworth et al. |
| 2012/0171199 A1 | 7/2012 | Dotson et al. |
| 2012/0178737 A1 | 7/2012 | Shuttleworth et al. |
| 2013/0109688 A1 | 5/2013 | Shuttleworth et al. |
| 2014/0235671 A1 | 8/2014 | Shuttleworth et al. |
| 2015/0080395 A1 | 3/2015 | Shuttleworth et al. |
| 2016/0096804 A1 | 4/2016 | Shuttleworth et al. |
| 2016/0108057 A1 | 4/2016 | Shuttleworth et al. |

FOREIGN PATENT DOCUMENTS

| | | |
|---|---|---|
| CN | 101228161 A | 7/2008 |
| CN | 101663276 A | 3/2010 |
| CN | 104125946 A | 10/2014 |
| EP | 0226099 A2 | 6/1987 |

(Continued)

OTHER PUBLICATIONS

Lee; Tetrahedron 2010, 66, 9440-9444.*

(Continued)

*Primary Examiner* — Noble Jarrell
*Assistant Examiner* — Daniel Carcanague
(74) *Attorney, Agent, or Firm* — Goodwin Procter LLP

(57) ABSTRACT

A compound of the formula: (I) or a pharmaceutically acceptable salt thereof, wherein: L is a 5-membered nitrogen-containing heteroaryl which is optionally fused to a benzene; Y is a 5, 6 or 7-membered nitrogen-containing heteroaryl, which is optionally fused to a benzene; and W is a zinc-binding group. The compounds are HDAC inhibitors and therefore have potential utility in therapy.

8 Claims, No Drawings

(56) References Cited

FOREIGN PATENT DOCUMENTS

| | | | |
|---|---|---|---|
| EP | 0509400 | A1 | 10/1992 |
| EP | 0556396 | A1 | 8/1993 |
| EP | 0887348 | A1 | 12/1998 |
| EP | 1277738 | A1 | 1/2003 |
| EP | 1724267 | A1 | 11/2006 |
| EP | 2508510 | A1 | 10/2012 |
| EP | 2813506 | A1 | 12/2014 |
| JP | H11302254 | A | 11/1999 |
| JP | 2008542428 | A | 11/2008 |
| JP | 2012508223 | A | 4/2012 |
| JP | 201139550 | A | 5/2013 |
| JP | 2014503535 | A | 2/2014 |
| WO | WO-97/40017 | A2 | 10/1997 |
| WO | WO-01/83456 | A1 | 11/2001 |
| WO | WO-02/02551 | A1 | 1/2002 |
| WO | WO0234748 | * | 5/2002 |
| WO | WO-02/085400 | A1 | 10/2002 |
| WO | WO-03/075929 | A1 | 9/2003 |
| WO | WO-2004/072047 | A1 | 8/2004 |
| WO | WO-2006/037335 | A2 | 4/2006 |
| WO | WO-2006/046035 | A1 | 5/2006 |
| WO | WO-2006/088949 | | 8/2006 |
| WO | WO-2006/127587 | A1 | 11/2006 |
| WO | WO-2006/131484 | | 12/2006 |
| WO | WO-2007/050348 | A2 | 5/2007 |
| WO | WO-2007/084667 | A2 | 7/2007 |
| WO | WO-2007/085540 | A1 | 8/2007 |
| WO | WO-2007/122410 | A1 | 11/2007 |
| WO | WO-2007/127183 | A1 | 11/2007 |
| WO | WO-2008/007780 | A1 | 1/2008 |
| WO | WO-2008/033746 | | 3/2008 |
| WO | WO-2008/055068 | A2 | 5/2008 |
| WO | WO-2008/062201 | A1 | 5/2008 |
| WO | WO-2008/094992 | A2 | 8/2008 |
| WO | WO-2008/139987 | A1 | 11/2008 |
| WO | WO2008137270 | * | 11/2008 |
| WO | WO-2008/145688 | A2 | 12/2008 |
| WO | WO-2008/150827 | A1 | 12/2008 |
| WO | WO-2009/063240 | A1 | 5/2009 |
| WO | WO-2009/137462 | A2 | 11/2009 |
| WO | WO-2010/015520 | A1 | 2/2010 |
| WO | WO-2010/037765 | A2 | 4/2010 |
| WO | WO-2010/052569 | A2 | 5/2010 |
| WO | WO-2010/086646 | A1 | 8/2010 |
| WO | WO-2012/045804 | A1 | 4/2012 |
| WO | WO-2012/082997 | A1 | 6/2012 |
| WO | WO-2012/106343 | A2 | 8/2012 |
| WO | WO-2012/136722 | A1 | 10/2012 |
| WO | WO-2013/052110 | A1 | 4/2013 |
| WO | WO2013052613 | * | 4/2013 |
| WO | WO-2013/088404 | A1 | 6/2013 |
| WO | WO-2013/095060 | A1 | 6/2013 |
| WO | WO-2013/132270 | A1 | 9/2013 |
| WO | WO-2014/032019 | A2 | 2/2014 |
| WO | WO-2014/072714 | A1 | 5/2014 |
| WO | WO-2014/072937 | A1 | 5/2014 |
| WO | WO-2014/100227 | A1 | 6/2014 |
| WO | WO-2014/139465 | A1 | 9/2014 |
| WO | WO-2014/153280 | A1 | 9/2014 |
| WO | WO-2014/181137 | A1 | 11/2014 |
| WO | WO-2015/121657 | A1 | 8/2015 |
| WO | WO-2016/031815 | A1 | 3/2016 |
| WO | WO 2016/067040 | * | 5/2016 |

OTHER PUBLICATIONS

Elslager; Journal of Heterocyclic Chemistry 1973, 10, 611-622.*
Alvarez-Rua C et al., 'Multiple Hydrogen Bonds and Tautomerism in Naphthyridine Derivatives,' New J Chem, May 7, 2004 (May 7, 2004)(ePub), 28:700-7.
Anonymous, 'Abstract No. 2009:1018972 CAPLUS,' for 'Lett Drug Des Disc, (2009), 6(4):268-77,' STN CA Caesar Accession No. 1028, Nov. 17, 2015 (Nov. 17, 2015), CAplus Chemical Abstract Service, American Chemical Society, Columbus, OH (Publ), pp. 1-2 XP-002751577.
Anonymous, 'CAS Registration No. RN-1257852-06-4 for Glycine, N-1H-imadazol-1-yl-N-3-pyridazinyl,' Dec. 29, 2010 (Dec. 29, 2010), CAS Registry, Chemical Abstracts Service, American Chemical Society, Columbus, OG (Publ), pp. 1, XP-002751578.
Anonymous, Chemcats, Accession No. 0056415163, for '1,6-Naphthyridine, 7-(3-methylphenyl)-5-(4-morpholinyl)-' Apr. 22, 2011 (Apr. 22, 2011), CAS Registry No. 1214393-37-9, Chemical Abstracts Service, American Chemical Society, Columbus, OH (Publ), pp. 1, XP-002643660.
Anonymous, Chemcats, Accession No. 0056415178, for '1,6-Naphthyridine, 5-(4-morpholinyl)-7-(2-pyridinyl)-,' Apr. 22, 2011 (Apr. 22, 2011), CAS Registry No. 1214438-02-4, Chemical Abstracts Service, American Chemical Society, Columbus, OH (Publ), pp. 1, XP-002643660.
Anonymous, PubChem, '3-(1H-Indol-3-y1)-3-(pyridin-4-yl)propionic acid—Compound Summary,' CID 4715104, AC1NFWP0, MolPort-000-861-678, BBL022406, STK895679, AKOS000266205, MCULE-7014658967, 3-(1H-indol-3-yl)-3-pyridin-3-ylpropanoic acid, Sep. 17, 2005 (Sep. 17, 2005), National Center for Biotechnology Information, U.S. National Library of Medicine, Bethesda, MD (Publ), pp. 1-6 XP-002718389.
Anonymous, PubChem, '3-(1H-Indol-3-yl)-3-pyridin-4-yl-propionic acid—Compound,' CID 3157817, ST073698 3-(1H-indol-3-yl)-3-pyridin-4-ylpropanoic acid, 3-(1H-indol-3-yl)-3-(pyridin-4-yl)propanoic acid, Aug. 10, 2005 (Aug. 10, 2005), National Center for Biotechnology Information, U.S. National Library of Medicine, Bethesda, MD (Publ), pp. 1-7 XP-002718387.
Anonymous, PubChem, 'AC1LLZ4B—Compound Summary,' CID 1092973, (3S)-3-(1H-indol-3-yl)-3-pyridin-4-ylpropanoic acid, Jul. 10, 2005 (Jul. 10, 2005), National Center for Biotechnology Information, U.S. National Library of Medicine, Bethesda, MD (Publ), pp. 1-5 XP-002718385.
Anonymous, PubChem, 'AC1LLZ4D—Compound Summary,' CID 1092974, (3R)-3-(1H-indol-3-yl)-3-pyridin-4-ylpropanoic acid, Jul. 10, 2005 (Jul. 10, 2005), National Center for Biotechnology Information, U.S. National Library of Medicine, Bethesda, MD (Publ), pp. 1-5 XP-002718386.
Anonymous, PubChem, 'CID 40480236—Compound Summary,' CID 40480236, (3R)-3-(1H-indol3-yl)-3-pyridin-3-ylpropanoic acid, May 30, 2009 (May 30, 2009), National Center for Biotechnology Information, U.S. National Library of Medicine, Bethesda, MD (Publ), pp. 1-4 XP-002718391.
Anonymous, PubChem, 'ethyl 2 [pyridine-4-yl(pyrrol-1-yl)amino]acetate; hydrochloride,' CID 67857985, Nov. 30, 2012 (Nov. 30, 2012), National Center for Biotechnology Information, U.S. National Library of Medicine, Bethesda, MD (Publ), pp. 1-5 XP-002718393.
Anonymous, PubChem, 'SureCN2072816—Compound Summary,' CID 58088407, 3-(4-methoxy-1H-indol-3-yl)-3-pyridin-4-ylpropanoic acid, Aug. 19, 2012 (Aug. 19, 2012), National Center for Biotechnology Information, U.S. National Library of Medicine, Bethesda, MD (Publ), pp. 1-5 XP-002718392.
Anonymous, PubChem, 'SureCN9469183—Compound Summary,' CID 14373294, ethyl 2-[pyridine-4-yl(pyrrol-1-yl)amino]acetate, Feb. 9, 2007 (Feb. 9, 2007), National Center for Biotechnology Information, U.S. National Library of Medicine, Bethesda, MD (Publ), pp. 1-5 XP-002718390.
Assem el-SK et al., 'Effects of a Section of Histone Deacetylase Inhibitors on Mast Cell Activation and Airway and Colonic Smooth Muscles Contraction,' Int Immunopharmacol, Dec. 20, 2008 (Dec. 20, 2008) Sep. 19, 2008 (Sep. 19, 2008)(ePub), 8(13-14):1793-801.
Bouchecareilh M et al., 'Histone Deactylase Inhibitor (HDACi) Suberoylanilide Hydroxamic Acid (SAHA)-Mediated Correction of alpha1-Antitrypsin Deficiency,' J Biol Chem, Nov. 2, 2012 (Nov. 2, 2012) Sep. 20, 2012 (Sep. 20, 2012)(ePub), 287(45):38265-78.
Bruijnincx PC et al., 'Modeling the 2-His-1-carboxylate Facial Triad: Iron-catecholato Complexes as Structural and Functional Models of the Extrodiol Cleaving Dioxygenases,' J Am Chem Soc, Feb. 28, 2007 (Feb. 28, 2007) Feb. 1, 2007 (Feb. 1, 2007)(ePub), 129(8):2275-86.

(56) References Cited

OTHER PUBLICATIONS

Ciarlo E et al., 'Epigenetics in Sepsis: Targeting Histone Deacetylases,' Int J Antimicrob Agents, Jun. 2013 (Jun. 2013) May 9, 2013 (May 9, 2013)(ePub), 42(Supp):S8-12.

Clarke JD et al., 'Differential Effects of Sulforaphane on Histone Deacetylases, Cell Cycle Arrest and Apoptosis in Normal Prostate Cells Versus Hyperplastic and Cancerous Prostate Cells,' Mol Nutr Food Res, Jul. 2011 (Jul. 2011) Mar. 4, 2011 (Mar. 4, 2011)(ePub), 55(7):999-1009.

Crisanti MC et al., 'The HDAC Inhibitor Panobinostat (LBH589) Inhibits Mesothelioma and Lung Cancer Cells in vitro and in vivo with Particular Efficacy for Small Cell Lung Cancer,' Mol Cancer Ther, Aug. 2009 (Aug. 2009) Aug. 11, 2009 (Aug. 11, 2009)(ePub), 8(8):2221-31.

Cuadro AM et al., 'Synthesis of Highly Stabilised Ylides from N-[2-(1,3-Bensazolylmethyl)] Pyridinium Salts,' Tetrahedron, Jan. 1990 (Jan. 1990), 46(17):6033-46.

Djabali K and Christiano AM, 'Hairless Contains a Novel Nuclear Matrix Targeting Signal and Associates with Histone Deacetylase 3 in Nuclear Speckles,' Differentiation, Oct. 2004 (Oct. 2004), 72(8):410-8.

Downes JM et al., 'Biological Analogs. Spectroscopic Characteristics of Mercato- and Disulfide-Copper (II) Coordination in Relation to Type I Proteins,' Inorg Chem, Apr. 1981 (Apr. 1981), 20(4):1081-6.

Diez-Barra E et al., 'Double Michael Addition of Azoles to Methyl Propiolate: A Straightforward Entry to Ligands With Two Heterocyclic Rings,' Tetrahedron Lett, Aug. 7, 2004 (Aug. 7, 2004)(ePub), 45(2004):6937-9.

Ferrara N and Alitalo K, 'Clinical Applications of Angiogenic Growth Factors and Their Inhibitors,' Nat Med, Dec. 1999 (Dec. 1999), 5(12):1359-64.

Galardon E et al., 'Modeling the Inhibition of Peptide Deformylase by Hydroxamic Acids: Influence of the Sulfur Donor,' Daltron Trans, Mar. 14, 2007 (Mar. 14, 2007) Jan. 23, 2007 (Jan. 23, 2007)(ePub), (10):1047-52.

Giannini G et al., 'Exploring bis-(indolyl)methane Moiety as an Alternative and Innovative CAP Group in the Design of Histone Deacetylase (HDAC) Inhibitors,' Bioorg Med Chem Lett, May 15, 2009 (May 15, 2009) Mar. 26, 2009 (Feb. 26, 2009)(ePub), 19(10):2840-3.

Gillespie J et al., 'Histone Deacetylases are Dysregulated in Rheumatoid Arthritis and a Novel Histone Deacetylase 3-Selective Inhibitor Reduces Interleukin-6 Production by Peripheral Blood Mononuclear Cells from Rheumatoid Arthritis Patients,' Arthritis Rheum, Feb. 2012 (Feb. 2012), 64(2):418-22.

Govindarajan N et al., 'Reducing HDAC6 Ameliorated Cognitive Deficits in Mouse Model for Alzheimer's Disease,' EMBO Mol Med, Jan. 2013 (Jan. 2013) Nov. 26, 2012 (Nov. 26, 2013)(ePub), 5(1):52-63.

Grattagliano I et al., 'Glutathione Peroxidase, Thioredoxin, and Membrane Protein Changes in Erythrocytes Predict Ribavirin-Induced Anemia,' Clin Pharmacol Ther, Oct. 2005 (Oct. 2005), 78(4):422-32.

Gryder BE at al., 'Histone Deacetylase Inhibitors Equipped with Estrogen Receptor Modulation Activity,' J Med Chem, Jul. 25, 2013 (Jul. 25, 2013) Jul. 3, 2013 (Jul. 3, 2013)(ePub), 56(14):5782-96.

Hancock WW et al., 'HDAC Inhibitor Therapy in Autoimmunity and Transplantation,' Ann Rheum Dis, Apr. 2012 (Apr. 2012), 71(Supp 2):i46-54.

Haquette P et al., 'Synthesis of N-Functionalized 2,2'-dipyridylamine Ligands, Complexation to Ruthenium (II) and Anchoring of Complexes to Papain from Papaya Latex,' J Organomet Chem, Mar. 15, 2009 (Mar. 15, 2009), 694(6):937-41.

Hawtree S et al., 'The Role of Histone Deacetylases in Rheumatoid Arthritis Fibroblast-like Synoviocytes,' Biochem Soc Trans, Jun. 2013 (Jun. 2013), 41(3):783-8.

Hayakawa M et al., 'Synthesis and Biological Evaluation of pyrido[3',2':4,5]furo[3,2-d] Pyrimidine Derivatives as Novel P13 Kinasae p110alpha Inhibitors,' Bioorg Med Chem Lett, May 1, 2007 (May 1, 2007) Feb. 15, 2007 (Feb. 15, 2007)(ePub), 17(9):2438-42.

Hebbel RP et al., 'The HDAC Inhibitors Trichostatin A and Suberoylanalide Hydroxamic Acid Exhibit Multiple Modalities of Benefit for the Vascular Pathobiology of Sickle Transgenic Mice,' Blood, Mar. 25, 2010 (Mar. 25, 2010) Jan. 6, 2010 (Jan. 6, 2010), 115(12):2483-90.

Imesch P et al., 'Romidepsin Reduces Histone Deacetylase Activity, Induces Acetylation of Histones, Inhibits Proliferation, and Activates Apoptosis in Immortalized Epithelial Endometriotic Cells,' Fertil Steril, Dec. 2010 (Dec. 2010) Jun. 3, 2010 (Jun. 3, 2010)(ePub), 94(7):2838-42.

International Searching Authority, International Preliminary Report on Patentability (Form IB/373) and Written Opinion (Form ISA/237) for International Application No. PCT/GB2010/050116 (Form ISA/210), (Beligny S), completed on Apr. 27, 2012 (Apr. 27, 2012) and issued on Aug. 2, 2011 (Aug. 2, 2011), pp. 1-11.

International Searching Authority, International Preliminary Report on Patentability (Form IB/373) and Written Opinion (Form ISA/237) for International Application No. PCT/GB2010/051370 (Form ISA/210), (Helps I), completed on Oct. 28, 2010 (Oct. 28, 2010) and issued on Feb. 21, 2012 (Feb. 21, 2012), pp. 1-6.

International Searching Authority, International Preliminary Report on Patentability (Form IB/373) and Written Opinion (Form ISA/237) for International Application No. PCT/GB2011/050824 (Form ISA/210), (Marzi E), completed on Jun. 27, 2011 (Jun. 27, 2011) and issued on Nov. 6, 2012 (Nov. 6, 2012), pp. 1-7.

International Searching Authority, International Preliminary Report on Patentability (Form IB/373) and Written Opinion (Form ISA/237) for International Application No. PCT/GB2013/050583 (Form ISA/210), (Wolf C), completed on Apr. 11, 2013 (Apr. 11, 2013) and issued on Sep. 9, 2014 (Sep. 9, 2014), pp. 1-6.

International Searching Authority, International Preliminary Report on Patentability (Form IB/373) and Written Opinion (Form ISA/237) for International Application No. PCT/GB2013/052917 (Form ISA/210), (Sotoca Usina E), completed on Jan. 8, 2014 (Jan. 8, 2014) and issued on May 12, 2015 (May 12, 2015), pp. 1-11.

International Searching Authority, International Preliminary Report on Patentability (Form IB/373) and Written Opinion (Form ISA/237) for International Application No. PCT/GB2014/051454 (Form ISA/210), (Sotoca Usina E), completed on Jun. 10, 2014 (Jun. 10, 2014) and issued on Nov. 10, 2015 (Nov. 10, 2015), pp. 1-7.

International Searching Authority, International Search Report for International Application No. PCT/GB2010/050116 (Form ISA/210), (Beligny S), completed on Apr. 27, 2012 (Apr. 27, 2012) and mailed on May 10, 2010 (May 10, 2010), pp. 1-6.

International Searching Authority, International Search Report for International Application No. PCT/GB2010/051370 (Form ISA/210), (Helps I), completed on Oct. 28, 2010 (Oct. 28, 2010) and mailed on Nov. 9, 2010 (Nov. 9, 2010), pp. 1-4.

International Searching Authority, International Search Report for International Application No. PCT/GB2011/050824 (Form ISA/210), (Marzi E), completed on Jun. 27, 2011 (Jun. 27, 2011) and mailed on Jul. 12, 2011 (Jul. 12, 2011), pp. 1-5.

International Searching Authority, International Search Report for International Application No. PCT/GB2013/050583 (Form ISA/210), (Wolf C), completed on Apr. 11, 2013 (Apr. 11, 2013) and mailed on May 6, 2013 (May 6, 2013), pp. 1-4.

International Searching Authority, International Search Report for International Application No. PCT/GB2013/052917 (Form ISA/210), (Sotoca Usina E), completed on Jan. 8, 2014 (Jan. 8, 2014) and mailed on Jan. 22, 2014 (Jan. 22, 2014), pp. 1-9.

International Searching Authority, International Search Report for International Application No. PCT/GB2014/051454 (Form ISA/210), (Sotoca Usina E), completed on Jun. 10, 2014 (Jun. 10, 2014) and mailed on Jun. 17. 2014 (Jun. 17, 2014), pp. 1-4.

International Searching Authority, International Search Report for International Application No. PCT/GB2015/053256 (Form ISA/210), (Ladenburger C), completed on Nov. 26, 2015 (Nov. 26, 2015) and mailed on Dec. 8, 2015 (Dec. 8, 2015), pp. 1-7.

(56) References Cited

OTHER PUBLICATIONS

International Searching Authority, International Search Report for International Application No. PCT/GB2015/053260 (Form ISA/210), (Ladenburger C), completed on Nov. 30, 2015 (Nov. 30, 2015) and mailed on Dec. 9, 2015 (Dec. 9, 2015), pp. 1-9.
International Searching Authority, Written Opinion (Form ISA/237) for International Application No. PCT/GB2015/053256 (Form ISA/210), (Ladenburger C), completed on Nov. 26, 2015 (Nov. 26, 2015) and mailed on Dec. 8, 2015 (Dec. 8, 2015), pp. 1-6.
International Searching Authority, Written Opinion (Form ISA/237) for International Application No. PCT/GB2015/053260 (Form ISA/210), (Ladenburger C), completed on Nov. 30, 2015 (Nov. 30, 2015) and mailed on Dec. 9, 2015 (Dec. 9, 2015), pp. 1-7.
Kato K et al., 'Thromboxane Synthetase Inhibitors (TXSI). Design, Synthesis, and Evaluation of Novel Series of Omega-Pyridylalkenoic Acids,' J Med Chem, Mar. 1985 (Mar. 1985), 28(3):287-94.
Kazantsev AG and Thompson LM, 'Therapeutic Application of Histone Deacetylase Inhibitors for Central Nervous System Disorders,' Nat Rev Drug Discov, Oct. 2008 (Oct. 2008), 7(10):854-68.
Kim MG et al., 'The Relationship Between Cisplatin Resistance and Histone Deacetylase Isoform Overexpression in Epithelial Ovarian Cancer Cell Lines,' J Gynecol Oncol, Jul. 2012 (Jul. 2012) Jul. 2, 2012 (Jul. 2, 2012)(ePub), 23(3):182-9.
Kirin Si et al., 'Synthesis and Characterization of CuII Complexes with Amino Acid Substituted di(2-pyridyl)amine Ligands,' Eur J Inorg Chem, Jun. 22, 2007 (Jun. 22, 2007)(ePub), 2007(23):3686-94.
Kovacs J and Mokhir A, 'Nucleic Acid Controlled Catalysts of Carboxylic Esters Hydrolysis,' Bioorg Med Chem Lett, Nov. 1, 2008 (Nov. 1, 2008) Sep. 27, 2008 (Sep. 27, 2008)(ePub), 18(21):5722-4.
Kovalskiy DA and Perevalov VP, 'Synthesis of 7-(3-piperidyl)-[1,6]naphthyridine and 7-(4-pipe-ridyl)[1,6]naphthyridine,' Chem Hetercycl Comp, Nov. 24, 2009 (Nov. 24, 2009)(ePub), 45(9):1053-7 ISSN:0009-3122.
Kuendgen A et al., 'Treatment of Poor-Risk Myelodysplastic Syndromes and Acute Myeloid Leukemia with a Combination of 5-Azacytidine and Valproic Acid,' Clin Epigenetics, Aug. 2011 (Aug. 2011) Apr. 8, 2011 (Apr. 8, 2011)(ePub), 2(2):389-99.
Lee SU et al., 'In vitro and in vivo Osteogenic Activity of Largazole,' ACS Med Chem Lett, Mar. 10, 2011 (Mar. 10, 2011), 2(3):248-51.
Lemon DD et al., 'Cardiac HDAC6 Catalytic Activity is Induced in Response to Chronic Hypertension,' J Mol Cell Cardiol, Jul. 2011 (Jul. 2011) Apr. 23, 2011 (Apr. 23, 2011)(ePub), 51(1):41-50.
Lu W et al., 'Pd-Catalyzed Selective Addition of Heteroaromatic C-H Bonds to C-C Triple Bonds Under Mild Conditions,' Org Lett, Sep. 21, 2000 (Sep. 21, 2000), 2(19):2927-30.
Mai A et al., 'Identification of two new Synthetic Histone Deacetylase Inhibitors that Modulate Globin Gene Expression in Erythroid Cells from Healthy Donors and Patients with Thalassemia,' Mol Pharamcol, Nov. 2007 (Nov. 2007) Jul. 31, 2007 (Jul. 31, 2007)(ePub), 72(5):1111-23.
McGraw AL, 'Romidepsin for the Treatment of T-cell Lymphomas,' Am J Health Syst Pharm, Jul. 1, 2013 (Jul. 1, 2013), 70(13):1115-22.
McKinsey TA, 'The Biology and Therapeutic Implications of HDACs in the Heart,' Handb Exp Pharmacol, 2011 (2011), 206:57-78.
Meredith EL et al., 'Identification of Orally Available Naphthyridine Protein Kinase D Inhibitors,' J Med Chem, Aug. 12, 2010 (Aug. 12, 2010), 53(15):5400-21.
Moradei O et al., 'Histone Deacetylase Inhibitors in Cancer Therapy: New Compounds and Clinical Update of Benzamide-type Agents,' Curr Top Med Chem, 2008 (2008), 8(10):841-58.
Mull RP et al., 'Antihypertensively Active Amidoximes,' J Am Chem Soc, Jul. 1, 1958 (Jul. 1, 1958), 80(14):3769-72.
Nemenoff R, 'Wound Healing: A Role for HDACs in Inhibition of Fibroblast Proliferation Through Repression of PDGF Receptor-alpha. Focus on Repression of PDGF-R-alpha After Cellular Injury Involves TNF-alpha Formation of a c-Fos-YY1 Complex, and Negative Regulation by HDAC,' Am J Physiol Cell Physiol, Jun. 1, 2012 (Jun. 1, 2012) Mar. 28, 2012 (Mar. 28, 2012)(ePub), 302(11):C1588-9.
Ohashi A et al., 'Covalent Linking of Coordination-Organized Slipped Cofacial Porphyrin Dimers,' Bull Chem Soc Jpn, Feb. 10, 2004 (Feb. 10, 2004)(ePub), 77(2004):365-74.
Oyamada J and Kitamura T, 'Pt(II)-Catalyzes Hydroarylation Reaction of Alkynes with Pyrroles and Furans,' Tetrahedron, Mar. 14, 2009 (Mar. 14, 2009)(ePub), 65(2009):3842-7.
Patra N et al., 'A Novel Histone Deacetylase (HDAC) Inhibitor MHY219 Induces Apoptosis via Up-Regulation of Androgen Receptor Expression in Human Prostate Cancer Cells,' Biomed Pharmacother, Jun. 2013 (Jun. 2013) Feb. 16, 2013 (Feb. 16, 2013)(ePub), 67(5):407-15.
Peters L et al., 'Synthesis and Transition Metal Complexes of 3,3-bis(1-vinylimidazol-2-yl)propionic Acid, A New N,N,O Ligand Suitable for Copolymerisation,' Inorg Chim Acta, Mar. 12, 2011 (Mar. 12, 2011), 374(2011):392-40.
Peters L et al., 'The New Facial Tripod Ligand 3,3-bis(1-methylimidazol-2-yl)propionic Acid and Carbonyl Complexes Thereof Containing Manganese and Rhenium,' J Organomet Chem, Nov. 25, 2004 (Nov. 25, 2004), 690(2005):2009-16.
Pham TX and Lee J, 'Dietary Regulation of Histone Acetylases and Deacetylases for the Prevention of Metabolic Diseases,' Nutrients, Nov. 28, 2012 (Nov. 28, 2012), 4(12):1868-86.
Piscopo M et al., 'H3 and H3.3 Histone mRNA Amounts and Ratio in Oral Squamous Cell Carcinoma and Leukoplakia,' Oral Dis, Mar. 2006 (Mar. 2006), 12(2):130-6.
Price S and Dyke HJ, 'Histone Deacetylase Inhibitors: An Analysis of Recent Patenting Activity,' Exp Opin Therap Patents, Aug. 7, 2007 (Aug. 7, 2007)(ePub), 17(7):745-65.
Richardson PG et al., 'Preclinical Data and Early Clinical Experience Supporting the Use of Histone Deacetylase Inhibitors in Multiple Myeloma,' Leuk Res, Jul. 2013 (Jul. 2013) Apr. 9, 2013 (Apr. 9, 2013), 37(7):829-37.
Rotili D et al., 'Non-Cancer Uses of Histone Deacetylase Inhibitors: Effects on Infectious Diseases and beta-Hemoglobinopathies,' Curr Top Med Chem, 2009 (2009), 9(3):272-91.
Safdy ME et al., 'Tryptophan Analogues. 1. Synthesis and Antihypertensive Activity of Positional Isomers,' J Med Chem, Jun. 1982 (Jun. 1982), 25(6):723-30.
Saifuddin M et al., 'Water-Accelerated Cationic ?-(7-endo) Cyclisation: Application to Indole-Based Peri-Annulated Polyheterocycles,' Eur J Org Chem, Sep. 2010 (Sep. 2010) Jul. 20, 2010 (Jul. 20, 2010)(ePub), 2010(26):5108-17.
Shanmugam MK and Sethi G, 'Role of Epigenetics in Inflammation-Associated Diseases,' Subcell Biochem, 2013 (2013), 61:627-57 (PubMed Abstract only).
Singh B et al., 'Novel cAMP PDE III Inhibitors: 1,6-naphthyridin-2(1H)-ones,' J Med Chem, Dec. 25, 1992 (Dec. 25, 1992), 35(26):4858-65.
Singh J et al., 'HDAC Inhibitor SAHA Normalizes the Levels of VLCFAs in Human Skin Fibroblasts from X-ALD Patients and Downregulates the Expression of Proinflammatory Cytokines in Abcd1/2-Silenced Mouse Astrocytes,' J Lipid Res, Nov. 2011 (Nov. 2011) Sep. 4, 2011 (Sep. 4, 2011)(ePub), 52(11):2056-69.
Su GH et al., 'A Novel Histone Deacetylase Inhibitor Identified by High-Throughput Transcriptional Screening of a Compound Library,' Cancer Res, Jun. 15, 2000 (Jun. 15, 2000), 60(12):3137-42.
Suzuki T et al., 'Identification of G Protein-Coupled Receptor 120-Selective Agonists Derived from PPARgamma Agonists,' J Med Chem, Dec. 11, 2008 (Dec. 11, 2008), 51(23):7640-4.
Torrioli M et al., 'Treatment with Valproic Acid Ameliorates ADHD Symptoms in Fragile X Syndrome Boys,' Am J Med Genet A, Jun. 2010 (Jun. 2010), 152A(6):1420-7.
Usui S et al., 'Design, Synthesis, and Biological Activity of Novel PPARgamma Ligands Based on Rosiglitazone and 15d-PGJ2,' Bioorg Med Chem Lett, Mar. 15, 2005 (Mar. 15, 2005), 15(6):1547-51.

(56) References Cited

OTHER PUBLICATIONS

Van Damme M et al., 'HDAC Isoenzyme Expression is Deregulated in Chronic Lymphocytic Leukemia B-Cells and has a Complex Prognostic Significance,' Epigenetics, Dec. 1, 2012 (Dec. 1, 2012) Oct. 29, 2012 (Oct. 29, 2012), 7(12):1403-12.

Yamamoto T et al., 'Structure-Activity Relationship Study of 1,4-dihydropyridine Derivatives Blocking N-type Calcium Channels,' Bioorg Med Chem Lett, Feb. 15, 2006 (Feb. 15, 2006) Nov. 23, 2005 (Nov. 23, 2005)(ePub), 16(4):798-802.

Ye J, 'Improving Insulin Sensitivity with HDAC Inhibitor,' Diabetes, Mar. 2013 (Mar. 2013), 62(3):685-7.

Zakeeruddin SM et al., 'Glucose Oxidase Mediation by Soluble and Immobilized Electroactive Detergents,' Biosens Bioelectron, 1996 (1996), 11(3):305-15.

Zhang L et al., 'Inhibition of Histone Deacetylase-Induced Myocardial Repair is Mediated by c-Kit in Infarcted Hearts,' J Biol Chem, Nov. 16, 2012 (Nov. 16, 2012) Sep. 28, 2012 (Sep. 28, 2012)(ePub), 287(47):39338-48.

Lobera et al., "Selective class IIa deacetylase inhibition via a nonchelating zinc-binding group." Nat. Chem. Biol. 2013, 9, 319-325.

Madsen et al. The effect of various zinc binding groups on inhibition of histone deacetylases 1-11. ChemMedChem. Mar. 27, 2014; 9(3): 614-26.

\* cited by examiner

HISTONE DEACETYLASE INHIBITORS AND THEIR USE IN THERAPY

CROSS-REFERENCE TO RELATED APPLICATIONS

This application is the national phase of International Patent Application No. PCT/GB2013/052917, filed Nov. 6, 2013, which claims priority to applications GB1220029.1, filed Nov. 7, 2012, GB1309015.4, filed May 20, 2013, and GB1315254.1, filed Aug. 28, 2013, the entire disclosure of each of which is incorporated by reference herein.

FIELD OF THE INVENTION

The present invention relates to novel compounds which are inhibitors of histone deacetylase (HDAC) and therefore have therapeutic utility.

BACKGROUND OF THE INVENTION

HDACs are zinc metalloenzymes that catalyse the hydrolysis of acetylated lysine residues. In histones, this returns lysines to their protonated state and is a global mechanism of eukaryotic transcriptional control, resulting in tight packaging of DNA in the nucleosome. Additionally, reversible lysine acetylation is an important regulatory process for non-histone proteins. Thus, compounds which are able to modulate HDAC have important therapeutic potential.

WO2010/086646 discloses compounds which act as inhibitors of HDAC. In the claims, L is defined broadly as being a "nitrogen-containing" heteroaryl. All the exemplified compounds require that L is pyridyl or benzofused pyridyl.

SUMMARY OF THE INVENTION

It has surprisingly been found that replacing one of the "L" groups of the compounds disclosed in WO2010/086646 with a 5-membered heteroaryl, results in compounds with improved bioavailability. Without wishing to be bound by theory, it is believed that substitution of one of the "L" groups by the 5-membered isosteres disclosed herein makes the compounds of the invention less susceptible to oxidative turnover.

Therefore, the present invention is a compound of the formula

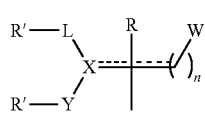

(I)

wherein:
⸗ is a double bond and X is C; or
⸗ is a single bond and X is N, CH or $CQR_1$, and
wherein:
n is 1 to 10;
R is H or $QR_1$;
each R' is independently selected from H and $QR_1$;
each Q is independently selected from a bond, CO, $CO_2$, NH, S, SO, $SO_2$ or O;
each $R_1$ is independently selected from H, $C_1$-$C_{10}$ alkyl, $C_2$-$C_{10}$ alkenyl, $C_2$-$C_{10}$ alkynyl, aryl, heteroaryl, $C_1$-$C_{10}$ cycloalkyl, halogen, $C_1$-$C_{10}$ alkylaryl, $C_{10}$ alkyl heteroaryl, $C_1$-$C_{10}$ heterocycloalkyl or trifluoromethyl;
L is a 5-membered nitrogen-containing heteroaryl which is optionally fused to a benzene;
Y is a 5, 6 or 7-membered nitrogen-containing heteroaryl, which is optionally fused to a benzene;
W is a zinc-binding group; and
each aryl or heteroaryl may be substituted by up to five substituents selected from $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono($C_1$-$C_3$ alkyl)amino $C_1$-$C_3$ alkyl, bis($C_1$-$C_3$ alkyl)amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl,
or a pharmaceutically acceptable salt thereof.

The compounds of the invention may be useful as an inhibitor of HDAC, i.e. in they may be used in a method of treating a disease associated with an over-expression of HDAC.

DESCRIPTION OF THE INVENTION

Definitions

As used herein, "alkyl" means a $C_1$-$C_{10}$ alkyl group, which can be linear or branched. Preferably, it is a $C_1$-$C_6$ alkyl moiety. More preferably, it is a $C_1$-$C_4$ alkyl moiety. Examples include methyl, ethyl, n-propyl and t-butyl. It may be divalent, e.g. propylene.

As used herein, "cycloalkyl" contains from 3 to 10 carbon atoms. It may be monovalent or divalent.

As used herein, "alkenyl" means a $C_2$-$C_{10}$ alkenyl group. Preferably, it is a $C_2$-$C_6$ alkenyl group. More preferably, it is a $C_2$-$C_4$ alkenyl group. The alkenyl radicals may be mono- or di-saturated, more preferably monosaturated. Examples include vinyl, allyl, 1-propenyl, isopropenyl and 1-butenyl. It may be divalent, e.g. propenylene As used herein, "alkynyl" is a $C_2$-$C_{10}$ alkynyl group which can be linear or branched. Preferably, it is a $C_2$-$C_4$ alkynyl group or moiety. It may be divalent.

Each of the $C_1$-$C_{10}$ alkyl, $C_2$-$C_{10}$ alkenyl and $C_2$-$C_{10}$ alkynyl groups may be optionally substituted with each other, i.e. $C_1$-$C_{10}$ alkyl optionally substituted with $C_2$-$C_{10}$ alkenyl. They may also be optionally substituted with aryl, cycloalkyl (preferably $C_3$-$C_{10}$), aryl or heteroaryl. They may also be substituted with halogen (e.g. F, Cl), $NH_2$, $NO_2$ or hydroxyl. Preferably, they may be substituted with up to 10 halogen atoms or more preferably up to 5 halogens. For example, they may be substituted by 1, 2, 3, 4 or 5 halogen atoms. Preferably, the halogen is fluorine.

As used herein, "aryl" means a monocyclic, bicyclic, or tricyclic monovalent or divalent (as appropriate) aromatic radical, such as phenyl, biphenyl, naphthyl, anthracenyl, which can be optionally substituted with up to five substituents preferably selected from the group of $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono($C_1$-$C_3$ alkyl)amino $C_1$-$C_3$ alkyl, bis($C_1$-$C_3$ alkyl)amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

As used herein, heteroaryl means a monocyclic, bicyclic or tricyclic monovalent or divalent (as appropriate) aromatic radical containing up to four heteroatoms selected from oxygen, nitrogen and sulfur, such as thiazolyl, isothiazolyl, tetrazolyl, imidazolyl, oxazolyl, isoxazolyl, thienyl, pyrazolyl, pyridinyl, pyrazinyl, pyrimidinyl, indolyl, quinolyl, isoquinolyl, triazolyl, thiadiazolyl, oxadiazolyl, said radical being optionally substituted with up to three substituents preferably selected from the group of $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono($C_1$-$C_3$ alkyl)amino $C_1$-$C_3$ alkyl, bis($C_1$-$C_3$ alkyl)amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

Preferred L groups are thiazolyl, imidazolyl, oxazolyl, pyrazolyl, thiadiazolyl and oxadiazolyl.

In the compounds of the invention, certain heteroaryl groups (i.e. L or Y) are attached to R'. However, they may still be substituted by up to three additional substituents, selected from the groups defined above.

As used herein, the term "heterocycle" or "heterocycloalkyl" is a mono- or di-valent carbocyclic radical containing up to 4 heteroatoms selected from oxygen, nitrogen and sulfur. It may be monocyclic or bicyclic. It is preferably saturated. The word 'linker' has been used herein to mean di-valent. If the heterocycle is a di-valent linker, the heterocycle may be attached to neighbouring groups through a carbon atom, or through on of the heteroatoms, e.g. a N. Examples of heterocycles are piperazine or morpholine.

The heterocyclic ring may be mono- or di-unsaturated. The radical may be optionally substituted with up to three substituents independently selected from $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono($C_1$-$C_3$ alkyl)amino $C_1$-$C_3$ alkyl, bis($C_1$-$C_3$ alkyl)amino $C_1$-$C_3$ alkyl, $C_1$-$C_3$-acylamino, $C_1$-$C_3$ alkyl sulfonylamino, halo e.g. F, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

As used herein, the above groups can be followed by the suffix-ene. This means that the group is divalent, i.e. a linker group.

Preferred Groups of the Invention

The group W is a zinc-chelating residue, i.e. a metallophile capable of binding with zinc in the active site of HDAC. Suitable metallophiles are known to those skilled in the art.

In a preferred embodiment, W is selected from:

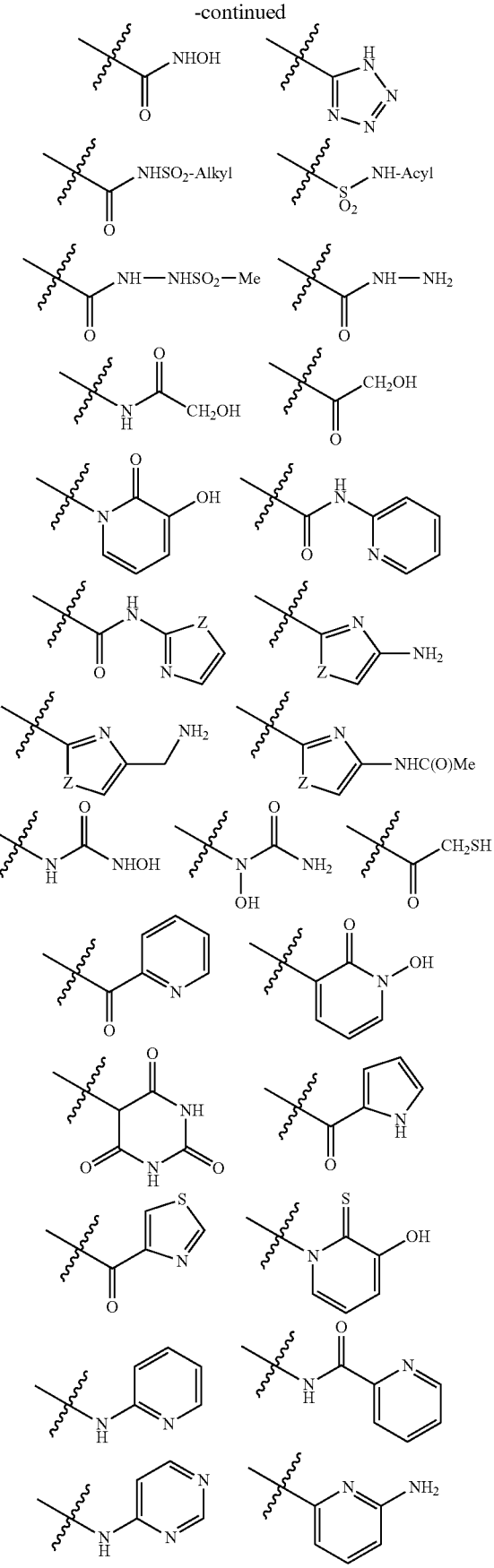

-continued

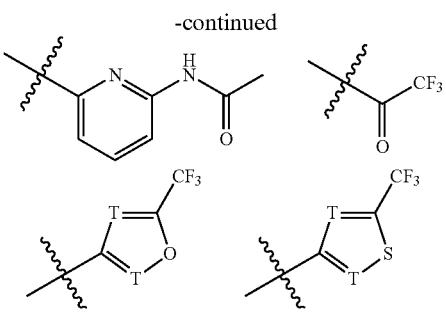

wherein $R_1$ is as defined in claim 1, $Pr^2$ is H or a thiol protecting group, Z is selected from O, S or NH and T is N or CH.

When W is $COOR_1$, preferably $R_1$ is not halogen. More preferably, when W is $COOR_1$, $R_1$ is H or $C_1$-$C_{10}$ alkyl.

Preferably, W is —COOH, COOMe, —CONHOH, —CONHSO$_2$CH$_3$, —CONHNHSO$_2$CH$_3$, —CONHNH$_2$, —CONH(2-pyridyl), —NHCONHOH, tetrazole, hydroxypyridin-2-thione or hydroxypyridin-2-one. Preferably W is not $COOR_1$. More preferably, W is COOMe, —CONHOH, CONHSO$_2$CH$_3$, —CONHNHSO$_2$CH$_3$, —CONHNH$_2$, —CONH(2-pyridyl) —NHCONHOH, tetrazole, hydroxypyridin-2-thione or hydroxypyridin-2-one. Even more preferably, W is —CONHOH, tetrazole, hydroxypyridin-2-thione or hydroxypyridin-2-one. Most preferably, W is —CONHOH.

Preferably, n is 3 to 7. More preferably, n is 6 or 7.

In a preferred embodiment, X--- is N— or, X--- is C=. Preferably, X--- is N.

In a preferred embodiment, at least one R′ is H, halogen (preferably F), $C_1$-$C_{10}$ alkyl or O—($C_1$-$C_{10}$ alkyl). Preferably, at least one R′ is substituted or unsubstituted aryl or O-(substituted or unsubstituted aryl). Preferably, at least one R′ is aryl or O-aryl, each of which may be substituted with a halogen, amino or $C_1$-$C_{10}$ alkyl. The aryl may be substituted in any position. The aryl may be mono-, bis-, or tri-substituted.

In a preferred embodiment, at least one R′ is H, $C_1$-$C_{10}$ alkyl or O—($C_1$-$C_{10}$ alkyl). Preferably, at least one R′ is substituted or unsubstituted aryl or O— (substituted or unsubstituted aryl). Preferably, at least one R′ is aryl or O-aryl, each of which may be substituted with a halogen, amino or $C_1$-$C_{10}$ alkyl. The aryl may be substituted in any position. The aryl may be mono-, bis-, or tri-substituted.

R′ may be substituted onto any of the ring atoms of the L or Y groups, i.e. the nitrogen-containing heteroaryl group. The nitrogen-containing heteroaryl may be benzofused, and the R′ may be substituted onto the benzo-portion of the L or Y group.

Preferably, Q is a direct bond or —O—. More preferably, Q is a direct bond.

Preferably, $R_1$ is halogen (preferably F), $C_1$-$C_{10}$ alkyl, $C_2$-$C_{10}$ alkenyl or $C_2$-$C_{10}$ alkynyl, preferably substituted with halogen, NH$_2$, NO$_2$ or hydroxyl. More preferably, $R_1$ is $C_1$-$C_{10}$ alkyl substituted with halogen which is preferably fluorine. The $C_1$-$C_{10}$ alkyl group may be substituted by up to 10 halogen atoms or preferably, by up to 5 halogen atoms, i.e., 1, 2, 3, 4 or 5 halogen atoms. For example, $R_1$ may be CF$_3$, CHF$_2$, CH$_2$CF$_3$, CH$_2$CHF$_2$ or CF$_2$CF$_3$. This means that R′ may be CF$_3$, CHF$_2$, CH$_2$CF$_3$, CH$_2$CHF$_2$ or CF$_2$CF$_3$ or OCF$_3$, OCHF$_2$, OCH$_2$CF$_3$, OCH$_2$CHF$_2$ or OCF$_2$CF$_3$.

Preferably, $R_1$ is $C_1$-$C_{10}$ alkyl, $C_2$-$C_{10}$ alkenyl or $C_2$-$C_{10}$ alkynyl, preferably substituted with halogen, NH$_2$, NO$_2$ or hydroxyl. More preferably, $R_1$ is $C_1$-$C_{10}$ alkyl substituted with halogen which is preferably fluorine. The $C_1$-$C_{10}$ alkyl group may be substituted by up to 10 halogen atoms or preferably, by up to 5 halogen atoms, i.e., 1, 2, 3, 4 or 5 halogen atoms. For example, $R_1$ may be CF$_3$, CHF$_2$, CH$_2$CF$_3$, CH$_2$CHF$_2$ or CF$_2$CF$_3$. This means that R′ may be CF$_3$, CHF$_2$, CH$_2$CF$_3$, CH$_2$CHF$_2$ or CF$_2$CF$_3$ or OCF$_3$, OCHF$_2$, OCH$_2$CF$_3$, OCH$_2$CHF$_2$ or OCF$_2$CF$_3$.

In a preferred embodiment, R is H or $C_1$ to $C_6$ alkyl.

In a preferred embodiment, L and/or Y is a hydrogen bond-acceptor, and preferably not also a hydrogen bond donor. Preferably, L and/or Y does not have a hydrogen atom attached to an electronegative atom, such as N or O. More preferably, L is not pyrrole or benzofused pyrrole. More preferably, L, most preferably L and Y, are hydrogen-bond acceptors.

The definitions of hydrogen bond acceptors/donors are known to those skilled in the art. For example, a hydrogen bond donor will have a hydrogen attached to an electronegative atom, such as N or O. For example, a hydrogen bond acceptor will have a N or O, which has a free lone pair.

Preferably in at least one, preferably both, of L and Y, the atom that is directly bonded to X is a carbon, and at least one nitrogen atom is directly bonded to said carbon (preferably via a double bond). More preferably, said nitrogen atom is a hydrogen bond acceptor.

Preferably, in addition to a N atom, L contains at least one other heteroatom in the heteroaryl ring which is selected from N, O or S.

In a preferred embodiment, L is:

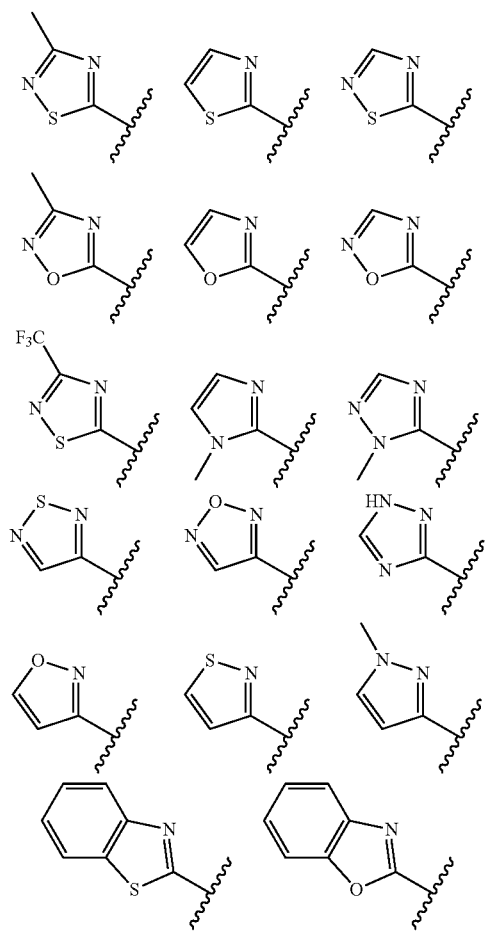

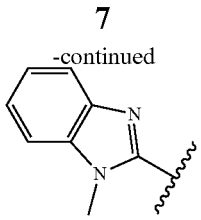

In a preferred embodiment, Y is:

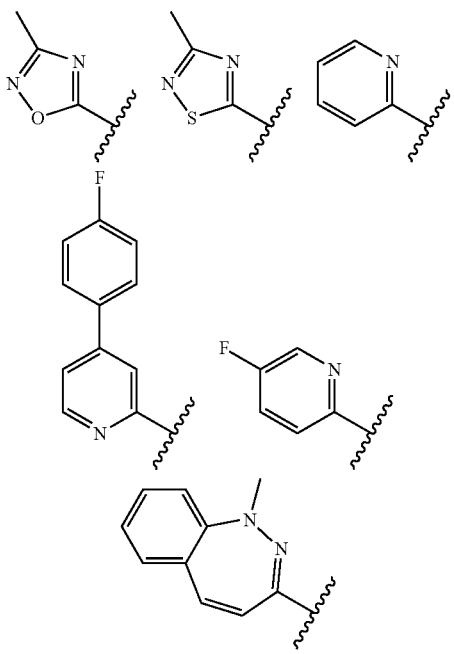

A pharmaceutical composition of the invention comprises a compound as defined above, and a pharmaceutically acceptable carrier or diluent. A pharmaceutical composition of the invention typically contains up to 85 wt % of a compound of the invention. More typically, it contains up to 50 wt % of a compound of the invention. Preferred pharmaceutical compositions are sterile and pyrogen-free. Further, the pharmaceutical compositions provided by the invention typically contain a compound of the invention which is a substantially pure optical isomer. Preferably, the pharmaceutical composition comprises a pharmaceutically acceptable salt form of a compound of the invention.

As used herein, a pharmaceutically acceptable salt is a salt with a pharmaceutically acceptable acid or base. Pharmaceutically acceptable acids include both inorganic acids such as hydrochloric, sulfuric, phosphoric, diphosphoric, hydrobromic or nitric acid and organic acids such as citric, fumaric, maleic, malic, ascorbic, succinic, tartaric, benzoic, acetic, methanesulfonic, ethanesulfonic, ethanedisulfonic, salicylic, stearic, benzenesulfonic or p-toluenesulfonic acid. Pharmaceutically acceptable bases include alkali metal (e.g. sodium or potassium) and alkali earth metal (e.g. calcium or magnesium) hydroxides and organic bases such as alkyl amines, aryl amines or heterocyclic amines.

For the avoidance of doubt, the present invention also embraces prodrugs which react in vivo to give a compound of the present invention.

The compounds of the present invention are found to be inhibitors of HDAC. The compounds of the present invention are therefore therapeutically useful in the treatment of conditions affected by HDAC activity.

The compounds of the invention may be prepared by synthetic routes that will be apparent to those skilled in the art, e.g. based on the Examples.

The compounds of the present invention are found to be inhibitors of HDAC. The compounds of the present invention are therefore therapeutically useful.

The compounds of the invention and compositions comprising them may be administered in a variety of dosage forms. In one embodiment, a pharmaceutical composition comprising a compound of the invention may be formulated in a format suitable for oral, rectal, parenteral, intranasal or transdermal administration or administration by inhalation or by suppository. Typical routes of administration are parenteral, intranasal or transdermal administration or administration by inhalation.

The compounds of the invention can be administered orally, for example as tablets, troches, lozenges, aqueous or oily suspensions, dispersible powders or granules. Preferred pharmaceutical compositions of the invention are compositions suitable for oral administration, for example tablets and capsules.

The compounds of the invention may also be administered parenterally, whether subcutaneously, intravenously, intramuscularly, intrasternally, transdermally or by infusion techniques. The compounds may also be administered as suppositories.

The compounds of the invention may also be administered by inhalation. An advantage of inhaled medications is their direct delivery to the area of rich blood supply in comparison to many medications taken by oral route. Thus, the absorption is very rapid as the alveoli have an enormous surface area and rich blood supply and first pass metabolism is bypassed. A further advantage may be to treat diseases of the pulmonary system, such that delivering drugs by inhalation delivers them to the proximity of the cells which are required to be treated.

The present invention also provides an inhalation device containing such a pharmaceutical composition. Typically said device is a metered dose inhaler (MDI), which contains a pharmaceutically acceptable chemical propellant to push the medication out of the inhaler.

The compounds of the invention may also be administered by intranasal administration. The nasal cavity's highly permeable tissue is very receptive to medication and absorbs it quickly and efficiently, more so than drugs in tablet form. Nasal drug delivery is less painful and invasive than injections, generating less anxiety among patients. By this method absorption is very rapid and first pass metabolism is usually bypassed, thus reducing inter-patient variability. Further, the present invention also provides an intranasal device containing such a pharmaceutical composition.

The compounds of the invention may also be administered by transdermal administration. The present invention therefore also provides a transdermal patch containing a compound of the invention.

The compounds of the invention may also be administered by sublingual administration. The present invention therefore also provides a sub-lingual tablet comprising a compound of the invention.

A compound of the invention may also be formulated with an agent which reduces degradation of the substance by processes other than the normal metabolism of the patient, such as anti-bacterial agents, or inhibitors of protease enzymes which might be the present in the patient or in commensural or parasite organisms living on or within the patient, and which are capable of degrading the compound.

Liquid dispersions for oral administration may be syrups, emulsions and suspensions.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

In one embodiment the compounds of the present invention may be used in combination with another known inhibitor of HDAC, such as SAHA. In this embodiment, the combination product may be formulated such that it comprises each of the medicaments for simultaneous, separate or sequential use.

The compounds of the present invention can be used in both the treatment and prevention of cancer and can be used in a monotherapy or in a combination therapy. When used in a combination therapy, the compounds of the present invention are typically used together with small chemical compounds such as platinum complexes, anti-metabolites, DNA topoisomerase inhibitors, radiation, antibody-based therapies (for example herceptin and rituximab), anti-cancer vaccination, gene therapy, cellular therapies, hormone therapies or cytokine therapy.

In one embodiment of the invention a compound of the invention is used in combination with another chemotherapeutic or antineoplastic agent in the treatment of a cancer. Examples of such other chemotherapeutic or antineoplastic agents include platinum complexes including cisplatin and carboplatin, mitoxantrone, vinca alkaloids for example vincristine and vinblastine, anthracycline antibiotics for example daunorubicin and doxorubicin, alkylating agents for example chlorambucil and melphalan, taxanes for example paclitaxel, antifolates for example methotrexate and tomudex, epipodophyllotoxins for example etoposide, camptothecins for example irinotecan and its active metabolite SN38 and DNA methylation inhibitors for example the DNA methylation inhibitors disclosed in WO02/085400.

According to the invention, therefore, products are provided which contain a compound of the invention and another chemotherapeutic or antineoplastic agent as a combined preparation for simultaneous, separate or sequential use in alleviating a cancer. Also provided according to the invention is the use of compound of the invention in the manufacture of a medicament for use in the alleviation of cancer by coadministration with another chemotherapeutic or antineoplastic agent. The compound of the invention and the said other agent may be administrated in any order. In both these cases the compound of the invention and the other agent may be administered together or, if separately, in any order as determined by a physician.

HDAC is believed to contribute to the pathology and/or symptomology of several different diseases such that reduction of the activity of HDAC in a subject through inhibition of HDAC may be used to therapeutically address these disease states. Examples of various diseases that may be treated using the HDAC inhibitors of the present invention are described herein.

One set of indications that HDAC inhibitors of the present invention may be used to treat is those involving undesirable or uncontrolled cell proliferation. Such indications include benign tumours, various types of cancers such as primary tumours and tumour metastasis, restenosis (e.g. coronary, carotid, and cerebral lesions), abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants. More specific indications for HDAC inhibitors include, but are not limited to prostate cancer, lung cancer, acute leukaemia, multiple myeloma, bladder carcinoma, renal carcinoma, breast carcinoma, colorectal carcinoma, neuroblastoma and melanoma.

In one embodiment, a method is provided for treating diseases associated with undesired and uncontrolled cell proliferation. The method comprises administering to a subject suffering from uncontrolled cell proliferation a therapeutically effective amount of a HDAC inhibitor according to the present invention, such that said uncontrolled cell proliferation is reduced. The particular dosage of the inhibitor to be used will depend on the severity of the disease state, the route of administration, and related factors that can be determined by the attending physician. Generally, acceptable and effective daily doses are amounts sufficient to effectively slow or eliminate uncontrolled cell proliferation.

HDAC inhibitors according to the present invention may also be used in conjunction with other agents to inhibit undesirable and uncontrolled cell proliferation. Examples of other anti-cell proliferation agents that may be used in conjunction with the HDAC inhibitors of the present invention include, but are not limited to, retinoid acid and derivatives thereof, 2-methoxyestradiol, Angiostatin™ protein, Endostatin™ protein, suramin, squalamine, tissue inhibitor of metalloproteinase-I, tissue inhibitor of metalloproteinase-2, plasminogen activator inhibitor-1, plasminogen activator inhibitor-2, cartilage-derived inhibitor, paclitaxel, platelet factor 4, protamine sulfate (clupeine), sulfated chitin derivatives (prepared from queen crab shells), sulfated polysaccharide peptidoglycan complex (sp-pg), staurosporine, modulators of matrix metabolism, including for example, proline analogs ((1-azetidine-2-carboxylic acid (LACA), cishydroxyproline, d,l-3,4-dehydroproline, thiaproline), beta-aminopropionitrile fumarate, 4-propyl-5-(4-pyridinyl)-2(3H)-oxazolone; methotrexate, mitoxantrone, heparin, interferons, 2 macroglobulin-serum, chimp-3, chymostatin, beta-cyclodextrin tetradecasulfate, eponemycin; fumagillin, gold sodium thiomalate, d-penicillamine (CDPT), beta-1-anticollagenase-serum, alpha-2-antiplasmin, bisantrene, lobenzarit disodium, n-(2-carboxyphenyl-4-chloroanthronilic acid disodium or "CCA", thalidomide; angiostatic steroid, carboxyaminoimidazole; metalloproteinase inhibitors such as BB94. Other anti-angiogenesis agents that may be used include antibodies, preferably monoclonal antibodies against these angiogenic growth factors: bFGF, aFGF, FGF-5, VEGF isoforms, VEGF-C, HGF/SF and Ang-1/Ang-2. Ferrara N. and Alitalo, K. "Clinical application of angiogenic growth factors and their inhibitors" (1999) Nature Medicine 5:1359-1364.

Generally, cells in benign tumours retain their differentiated features and do not divide in a completely uncontrolled manner. A benign tumour is usually localized and nonmetastatic. Specific types of benign tumours that can be treated using HDAC inhibitors of the present invention include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In the case of malignant tumors, cells become undifferentiated, do not respond to the body's growth control signals, and multiply in an uncontrolled manner. Malignant tumors are invasive and capable of spreading to distant sites (metastasizing). Malignant tumors are generally divided into two categories: primary and secondary. Primary tumors arise directly from the tissue in which they are found. Secondary tumours, or metastases, are tumours that originated elsewhere in the body but have now spread to distant organs. Common routes for metastasis are direct growth into adjacent structures, spread through the vascular or lymphatic systems, and tracking along tissue planes and body spaces (peritoneal fluid, cerebrospinal fluid, etc.).

Specific types of cancers or malignant tumours, either primary or secondary, that can be treated using the HDAC inhibitors of the present invention include, but are not limited to, leukaemia, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumour, small-cell lung tumour, gallstones, islet cell tumour, primary brain tumour, acute and chronic lymphocytic and granulocytic tumours, hairy-cell tumour, adenoma, hyperplasia, medullary carcinoma, pheochromocytoma, mucosal neuromas, intestinal ganglloneuromas, hyperplastic corneal nerve tumour, marfanoid habitus tumour, Wilms' tumour, seminoma, ovarian tumour, leiomyomater tumour, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumour, polycythermia vera, adenocarcinoma, glioblastoma multiforme, leukemias, lymphomas, malignant melanomas, epidermoid carcinomas, and other carcinomas and sarcomas.

The HDAC inhibitors of the present invention may also be used to treat abnormal cell proliferation due to insults to body tissue during surgery. These insults may arise as a result of a variety of surgical procedures such as joint surgery, bowel surgery, and cheloid scarring. Diseases that produce fibrotic tissue that may be treated using the HDAC inhibitors of the present invention include emphysema. Repetitive motion disorders that may be treated using the present invention include carpal tunnel syndrome. An example of a cell proliferative disorder that may be treated using the invention is a bone tumour.

Proliferative responses associated with organ transplantation that may be treated using HDAC inhibitors of the invention include proliferative responses contributing to potential organ rejections or associated complications. Specifically, these proliferative responses may occur during transplantation of the heart, lung, liver, kidney, and other body organs or organ systems.

Abnormal angiogenesis that may be treated using this invention include those abnormal angiogenesis accompanying rheumatoid arthritis, ischemic-reperfusion related brain edema and injury, cortical ischemia, ovarian hyperplasia and hypervascularity, polycystic ovary syndrome, endometriosis, psoriasis, diabetic retinopathy, and other ocular angiogenic diseases such as retinopathy of prematurity (retrolental fibroplastic), macular degeneration, corneal graft rejection, neuroscular glaucoma and Oster Webber syndrome.

Examples of diseases associated with uncontrolled angiogenesis that may be treated according to the present invention include, but are not limited to retinal/choroidal neovascularization and corneal neovascularization. Examples of diseases which include some component of retinal/choroidal neovascularization include, but are not limited to, Best's diseases, myopia, optic pits, Stargart's diseases, Paget's disease, vein occlusion, artery occlusion, sickle cell anemia, sarcoid, syphilis, pseudoxanthoma elasticum carotid apo structive diseases, chronic uveitis/vitritis, mycobacterial infections, Lyme's disease, systemic lupus erythematosus, retinopathy of prematurity, Eale's disease, diabetic retinopathy, macular degeneration, Bechet's diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi sarcoma.

Chronic inflammatory diseases associated with uncontrolled angiogenesis may also be treated using HDAC inhibitors of the present invention. Chronic inflammation depends on continuous formation of capillary sprouts to maintain an influx of inflammatory cells. The influx and presence of the inflammatory cells produce granulomas and thus maintains the chronic inflammatory state. Inhibition of angiogenesis using a HDAC inhibitor alone or in conjunction with other anti-inflammatory agents may prevent the formation of the granulosmas and thus alleviate the disease. Examples of chronic inflammatory diseases include, but are not limited to, inflammatory bowel diseases such as Crohn's disease and ulcerative colitis, psoriasis, sarcoidosis, and rheumatoid arthritis.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhoea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhoea. These inflammatory bowel diseases are generally caused by chronic granulomatous inflammation throughout the gastrointestinal tract, involving new capillary sprouts surrounded by a cylinder of inflammatory cells. Inhibition of angiogenesis by these inhibitors should inhibit the formation of the sprouts and prevent the formation of granulomas. Inflammatory bowel diseases also exhibit extra intestinal manifestations, such as skin lesions. Such lesions are characterized by inflammation and angiogenesis and can occur at many sites other the gastrointestinal tract. Inhibition of angiogenesis by HDAC inhibitors according to the present invention can reduce the influx of inflammatory cells and prevent lesion formation.

Sarcoidosis, another chronic inflammatory disease, is characterized as a multisystem granulomatous disorder. The granulomas of this disease can form anywhere in the body. Thus, the symptoms depend on the site of the granulomas and whether the disease is active. The granulomas are created by the angiogenic capillary sprouts providing a constant supply of inflammatory cells. By using HDAC inhibitors according to the present invention to inhibit angiogenesis, such granulomas formation can be inhibited. Psoriasis, also a chronic and recurrent inflammatory disease, is characterized by papules and plaques of various sizes. Treatment using these inhibitors alone or in conjunction with other anti-inflammatory agents should prevent the formation of new blood vessels necessary to maintain the characteristic lesions and provide the patient relief from the symptoms.

Rheumatoid arthritis (RA) is also a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using HDAC inhibitors according to the present invention alone or in conjunction with other anti-RA agents may prevent the formation of new blood vessels necessary to maintain the chronic inflammation.

The compounds of the present invention can further be used in the treatment of cardiac/vasculature diseases such as hypertrophy, hypertension, myocardial infarction, reperfusion, ischaemic heart disease, angina, arryhtmias, hypercholesterolemia, atherosclerosis and stroke. The compounds can further be used to treat neurodegenerative disorders/CNS disorders such as acute and chronic neurological diseases, including stroke, Huntington's disease, Amyotrophic Lateral Sclerosis and Alzheimer's disease.

The compounds of the present invention can also be used as antimicrobial agents, for example antibacterial agents. The invention therefore also provides a compound for use in the treatment of a bacterial infection. The compounds of the present invention can be used as anti-infectious compounds against viral, bacterial, fungal and parasitic infections. Examples of infections include protozoal parasitic infections (including *plasmodium, cryptosporidium parvum, toxoplasma gondii, sarcocystis neurona* and *Eimeria* sp.)

The compounds of the present invention are particularly suitable for the treatment of undesirable or uncontrolled cell proliferation, preferably for the treatment of benign tumours/hyperplasias and malignant tumours, more preferably for the treatment of malignant tumours and most preferably for the treatment of chronic lymphocytic leukaemia (CLL), breast cancer, prostate cancer, ovarian cancer, mesothelioma, T-cell lymphoma.

In a preferred embodiment of the invention, the compounds of the invention are used to alleviate cancer, cardiac hypertrophy, chronic heart failure, an inflammatory condition, a cardiovascular disease, a haemoglobinopathy, a thalassemia, a sickle cell disease, a CNS disorder, an autoimmune disease, organ transplant rejection, diabetes, osteoporosis, MDS, benign prostatic hyperplasia, oral leukoplakia, a genentically related metabolic disorder, an infection, Rubens-Taybi, fragile X syndrome, or alpha-1 antitrypsin deficiency, or to accelerate wound healing, to protect hair follicles or as an immunosuppressant.

Typically, said inflammatory condition is a skin inflammatory condition (for example psoriasis, acne and eczema), asthma, chronic obstructive pulmonary disease (COPD), rheumatoid arthritis (RA), inflammatory bowel disease (IBD), Crohn's disease or colitis.

Typically, said cancer is chronic lymphocytic leukaemia, breast cancer, prostate cancer, ovarian cancer, mesothelioma or T-cell lymphoma.

Typically, said cardiovascular disease is hypertension, myocardial infarction (MI), ischemic heart disease (IHD) (reperfusion), angina pectoris, arrhythmia, hypercholesterolemia, hyperlipidaemia, atherosclerosis, stroke, myocarditis, congestive heart failure, primary and secondary i.e. dilated (congestive) cardiomyopathy, hypertrophic cardiomyopathy, restrictive cardiomyopathy, peripheral vascular disease, tachycardia, high blood pressure or thrombosis.

Typically, said genentically related metabolic disorder is cystic fibrosis (CF), peroxisome biogenesis disorder or adrenoleukodystrophy.

Typically, the compounds of the invention are used as an immunosuppressant following organ transplant.

Typically, said infection is a viral, bacterial, fungal or parasitic infection, in particular an infection by *S. aureus, P. acne, candida* or *aspergillus*.

Typically, said CNS disorder is Huntingdon's disease, Alzheimer's disease, multiple sclerosis or amyotrophic lateral sclerosis.

In this embodiment, the compounds of the invention may be used to alleviate cancer, cardiac hypertrophy, chronic heart failure, an inflammatory condition, a cardiovascular disease, a haemoglobinopathy, a thalassemia, a sickle cell disease, a CNS disorder, an autoimmune disease, diabetes or osteoporosis, or are used as an immunosuppressant.

The compounds of the invention may also be used to alleviate chronic lymphocytic leukaemia (CLL), breast cancer, prostate cancer, ovarian cancer, mesothelioma, T-cell lymphoma, cardiac hypertrophy, chronic heart failure or a skin inflammatory condition, in particular psoriasis, acne or eczema.

The compounds of the present invention can be used in the treatment of animals, preferably in the treatment of mammals and more preferably in the treatment of humans.

The compounds of the invention may, where appropriate, be used prophylactically to reduce the incidence of such conditions.

In use, a therapeutically effective amount of a compound of the invention is administered to a patient. A typical dose is from about 0.001 to 50 mg per kg of body weight, according to the activity of the specific compound, the age, weight and conditions of the subject to be treated, the type and severity of the disease and the frequency and route of administration.

Compounds of the invention may be tested for HDAC inhibitory activity by any suitable assay, e.g. the assay described in WO2008/062201.

The following Examples illustrate the invention.

Example A: N-Hydroxy-7-[(3-methyl-1,2,4-thiadiazol-5-yl)(pyridin-2-yl)amino]heptanamide

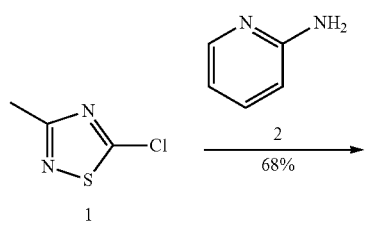

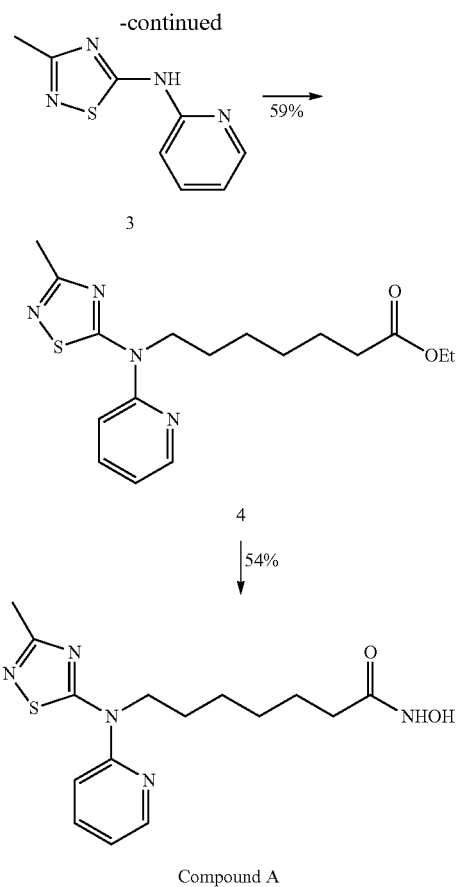

a. N-(3-Methyl-1,2,4-thiadiazol-5-yl)pyridin-2-amine (3)

5-Chloro-3-methyl-1,2,4-thiadiazole, 1 (362 mg, 2.69 mmol), 2-aminopyridine, 2 (460 mg, 2.69 mmol), tBuOK (453 mg, 4.03 mmol), (±) BINAP (67 mg, 0.10 mmol) and Pd$_2$(dba)$_3$ (61 mg, 0.07 mmol) were stirred in toluene (5 mL) at 90° C. under Ar(g) for 25 h. The reaction mixture was subsequently diluted with CH$_2$Cl$_2$ (5 mL); silica was then added and the solvent was removed by evaporation under reduced pressure. The resulting dry loaded material was purified by silica gel column chromatography, eluting with hexanes/EtOAc (6:1-2:1) to furnish 3 as a white solid (360 mg, 68%).

LCMS (ES): found 193.1 [MH]$^+$.

b. Ethyl-7-[(3-Methyl-1,2,4-thiadiazol-5-yl)(pyridin-2-yl)amino]heptanoate (4)

NaH (75 mg, 1.97 mmol) was added to N-(3-methyl-1,2,4-thiadiazol-5H)pyridin-2-amine, 3 (360 mg, 1.87 mmol) in DMF (10 mL) at rt. After 15 min, ethyl-7-iodoheptanoate (690 mg, 2.43 mmol) was added, and the resulting reaction mixture was stirred at 90° C. for 3 h under Ar(g). Once cooled to rt, the reaction mixture was poured onto brine (100 mL) and was then extracted twice with EtOAc (2×25 mL). The organic phases were combined, dried over MgSO$_4$, filtered, and subsequently evaporated under reduced pressure. The resulting residue was purified by silica gel column chromatography, eluting with hexanes/EtOAc (9:1-4:1) to furnish 4 as colourless oil (385 mg, 59%).

LCMS (ES): found 349.3 [MH]$^+$.

c. N-Hydroxy-7-[(3-methyl-1,2,4-thiadiazol-5-yl)(pyridin-2-yl)amino]heptanamide

Example A

A freshly prepared solution of NH$_2$OH in MeOH (1M, 25 mL) was added to 7-[(3-methyl-1,2,4-thiadiazol-5-yl)(pyridin-2-yl)amino]heptanoate, 4 (355 mg, 1.02 mmol) at 0° C. followed by KOH solubilised in MeOH (2M, 5 mL). The reaction mixture was then stirred at it for 21 h, was subsequently concentrated in vacuo (to 5 mL), then poured onto brine (50 mL), and extracted with EtOAc (3×25 mL). The organic phases were combined, dried over MgSO$_4$, filtered, and subsequently evaporated under reduced pressure. The resulting residue was purified by silica gel column chromatography, eluting with CH$_2$Cl$_2$/MeOH (25:1-20:1), to provide N-hydroxy-7-[(3-methyl-1,2,4-thiadiazol-5-yl)(pyridin-2-yl)amino]heptanamide, Example A, as a white solid (184 mg, 54%).

$^1$H NMR (400 MHz, Methanol-d$_4$) δ$_H$ (ppm): 1.37-1.53 (m, 4H), 1.64 (dt, J=14.7 Hz, 7.1 Hz, 2H), 1.81 (dt, J=14.3 Hz, 7.3 Hz, 2H), 2.10 (t, J=7.3 Hz, 2H), 2.48 (s, 3H), 4.45 (t, J=7.6 Hz, 2H), 7.12 (dd, J=7.3, 5.3 Hz, 1H), 7.37 (d, J=8.6 Hz, 1H), 7.92 (ddd, J=8.7 Hz, 7.2 Hz, 1.8 Hz, 1H), 8.49 (d, J=5.1 Hz, 1H).

LCMS (ES): found 336.0 [MH]$^+$.

Example B

N-Hydroxy-7-[(3-methyl-1,2,4-thiadiazol-5-yl)(pyridin-3-yl)amino]heptanamide

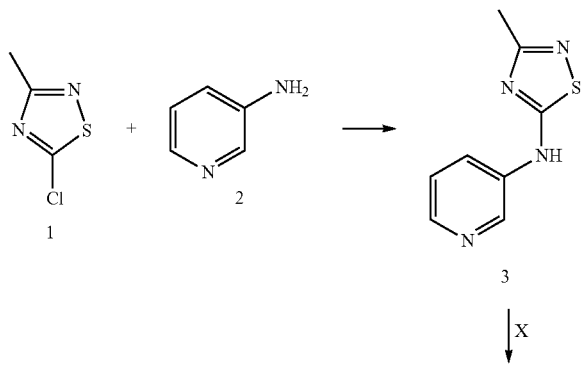

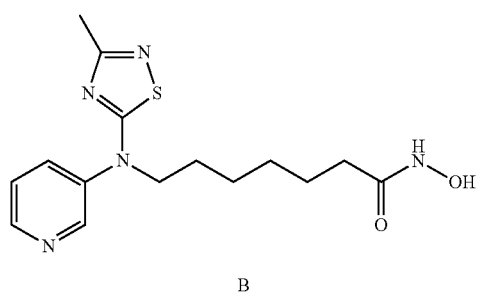

B

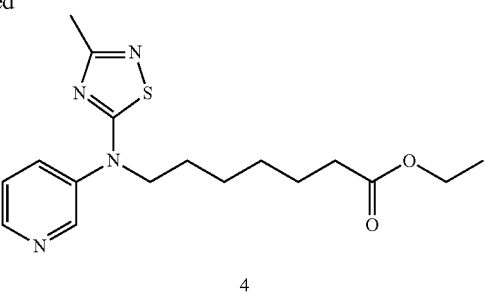

4 i. Ethyl 7-iodoheptanoate (X)

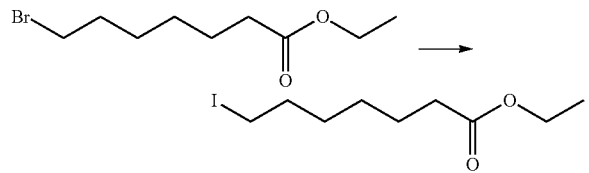

Sodium iodide (1.0 g, 6.67 mmol) was added to ethyl 7-bromoheptanoate (1.5 g, 5.97 mmol) in acetone (30 mL) and stirred with heating at 60° C. for 18 h. On cooling, TBME (30 mL) was added and the salts were filtered-off and washed with TBME (2×20 mL). The filtrate was then evaporated and the residue was treated with TBME (30 mL), this was then filtered, washed with TBME (2×20 mL) and evaporated, to afford (X) as an oil (1.8 g, 91%).

ii. N-Hydroxy-7-[(3-methyl-1,2,4-thiadiazol-5-yl)(pyridin-3-yl)amino]heptanamide (B)

A mixture of 3-aminopyridine (2) (0.32 g, 3.4 mmol), 5-chloro-3-methyl-1,2,4-thiadiazole (1) (0.45 g, 3.34 mmol), potassium t-butoxide (0.57 g, 5.1 mmol) and ±BINAP (85 mg, 4 mol %) in toluene (10 mL) was degassed by bubbling $N_2$(g) through for 10 min. $Pd_2$(dba)$_3$ (78 mg, 2.5 mol %) was added and degassed by bubbling $N_2$(g) through for 10 min, and the reaction mixture was then heated with stirring at 90° C. After 18 h, the reaction mixture was cooled, diluted with $CH_2Cl_2$ and evaporated onto silica. Purification on silica, eluting with petrol/EtOAc (1:1-0:1), afforded a yellow solid. This solid was subsequently dissolved in $CH_2Cl_2$/methanol (1:1) (100 mL) and was gently stirred with MP-TMT resin (0.57 g). After 1 day, the resin was removed by filtration, and the filtrate was evaporated to furnish (3) as a solid (340 mg, 51%).

LCMS (ES): found 193.0 [MH]$^+$.

NaH (60% in oil) (78 mg) was added to a solution of N-(3-methyl-1,2,4-thiadiazol-5-yl)pyridin-3-amine (3) (340 mg, 1.77 mmol) in DMF (10 mL). After 1 h, ethyl 7-iodoheptanoate (X) (650 mg, 2.2 mmol) in DMF (2 mL) was added, and the reaction mixture heated under $N_2$(g) with stirring, at 70° C. After 18 h, the reaction mixture was cooled, poured onto saturated brine solution and extracted with EtOAc (×3). The combined organic fractions were washed with saturated brine solution, dried over sodium sulfate, filtered and evaporated. Purification on silica eluting with petrol/EtOAc (1:1-1:3) furnished (4) an orange oil (500 mg, 81%).

LCMS (ES): found 349.0 [MH]$^+$.

50% Hydroxylamine aqueous solution (4 mL) was added to a solution of ethyl 7-[(3-methyl-1,2,4-thiadiazol-5-yl)(pyridin-3-yl)amino]heptanoate (4) (250 mg, 0.71 mmol) in methanol (4 mL), and the resulting solution was stirred at 30° C. for 24 h. Further 50% hydroxylamine aqueous solution (2 mL) was then added, and heating was continued at 30° C. for an additional 24 h. The reaction mixture was evaporated and azeotroped with toluene (×2). Purification on silica, eluting with $CH_2Cl_2$/MeOH (1:0-8:1), afforded N-hydroxy-7-[(3-methyl-1,2,4-thiadiazol-5-yl)(pyridin-3-yl)amino]heptanamide, Example B, as an orange oil (5 mg, 2%).

$^1$H NMR (400 MHz, CHLOROFORM-d) δ: 8.49-8.79 (m, 2H), 7.84 (d, J=7.6 Hz, 1H), 7.46 (d, J=5.5 Hz, 1H), 3.93 (t, J=6.2 Hz, 3H), 2.43 (s, 3H), 2.04-2.24 (m, 2H), 1.55-1.75 (m, 4H), 1.28-1.42 (m, 4H).

LCMS (ES): found 336.0 [MH]$^+$.

Example C

N-Hydroxy-7-((3-methyl-1,2,4-oxadiazol-5-yl)(pyridin-2-yl)amino)heptanamide

-continued

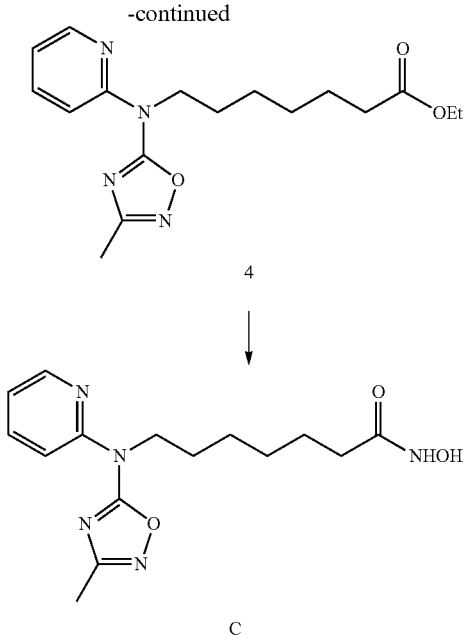

2-Bromopyridine (1) (1.0 g, 6.32 mmol), 3-methyl-1,2,4-oxadiazol-5-amine (2) (0.94 g, 9.49 mmol), Xantphos (0.37 g, 0.63 mmol), and Cs$_2$CO$_3$ (4.1 g, 12.64 mmol) were combined in dry 1,4-dioxane (15 mL). The reaction mixture was degassed with N$_2$(g) and placed under vacuum for 10 min. Pd$_2$(dba)$_3$ (0.28 g, 0.31 mmol) was then added to the reaction mixture, which was heated at 90° C. for 30 h. It was then poured into demineralized water (200 mL) and extracted with EtOAc (3×100 mL). The organic phases were combined, dried over Na$_2$SO$_4$, filtered and subsequently evaporated under vacuum. The resulting residue was purified by flash chromatography, eluting with EtOAc/Hexane (1:1) to provide 3-methyl-N-(pyridin-2-yl)1,2,4-oxadiazol-5-amine (3) as a white solid (0.70 g, 63%).

LCMS (ES): Found 177.1 [MH]$^+$.

NaH (60%) (42 mg, 1.01 mmol) was added portion-wise to 3-methyl-N-(pyridin-2-yl)1,2,4-oxadiazol-5-amine (3) (178 mg, 1.01 mmol) in DMF (5 mL) at 5° C. under Ar(g). The reaction mixture was then stirred for 20 min, and ethyl-7-iodoheptanoate (373 mg, 1.3 mmol) was then added. The reaction mixture was stirred at 80° C. under Ar(g) for 1 h in dark. The reaction mixture was then poured onto demineralized water (100 mL), and extracted with EtOAc (3×50 mL). The organic phases were combined, dried over Na$_2$SO$_4$, filtered and subsequently evaporated under vacuum. The resulting residue was purified by flash chromatography, eluting with EtOAc/Hexane (1:1) to ethyl 7-((3-methyl-1,2,4-oxadiazol-5-yl)(pyridin-2-yl)amino) heptanoate (4) as a white solid (134 mg, 40%).

LCMS (ES): Found 333.3 [MH]+.

A fresh solution of NH$_2$OH in MeOH was prepared [KOH (1.13 g, 20.18 mmol) in MeOH (10 mL) was added to NH$_2$OH.HCl (1.40 g, 20.18 mmol) in MeOH (10 mL) at 0° C.]. The reaction mixture was stirred for 20 min at 0° C., then filtered to remove salts; it was then added to (4) (134 mg, 0.40 mmol), and was then treated with KOH (226 mg, 4.03 mmol) solubilised in MeOH (5 mL). The reaction mixture was stirred at rt for 21 h, and then concentrated in vacuo, poured onto brine/H$_2$O (15 mL/35 mL), and extracted with CH$_2$Cl$_2$ (3×50 mL). The organic phases were combined, dried over MgSO$_4$, filtered, and subsequently evaporated under vacuum. The resulting residue was purified by silica gel column chromatography, eluting with MeOH/CH$_2$Cl$_2$ (1:9) to provide N-hydroxy-7-((3-methyl-1,2,4-oxadiazol-5-yl)(pyridin-2-yl)amino)heptanamide, Example C, as a light yellow solid (46 mg, 40%).

$^1$H NMR (400 MHz, DMSO-d$_5$) δ: 10.33 (br. s., 1H), 8.66 (br. s., 1H), 8.42-8.49 (m, 1H), 7.84-7.94 (m, 2H), 7.20-7.25 (m, 1H), 4.15 (t, J=7.4 Hz, 2H), 2.23 (s, 3H), 1.90 (t, J=7.3 Hz, 2H), 1.57-1.68 (m, 2H), 1.40-1.50 (m, 2H), 1.19-1.32 (m, 4H).

LCMS (ES): Found 320.1[MH]+.

Example D

N-Hydroxy-8-((3-methyl-1,2,4-oxadiazol-5-yl)(pyridin-2-yl)amino)octanamide

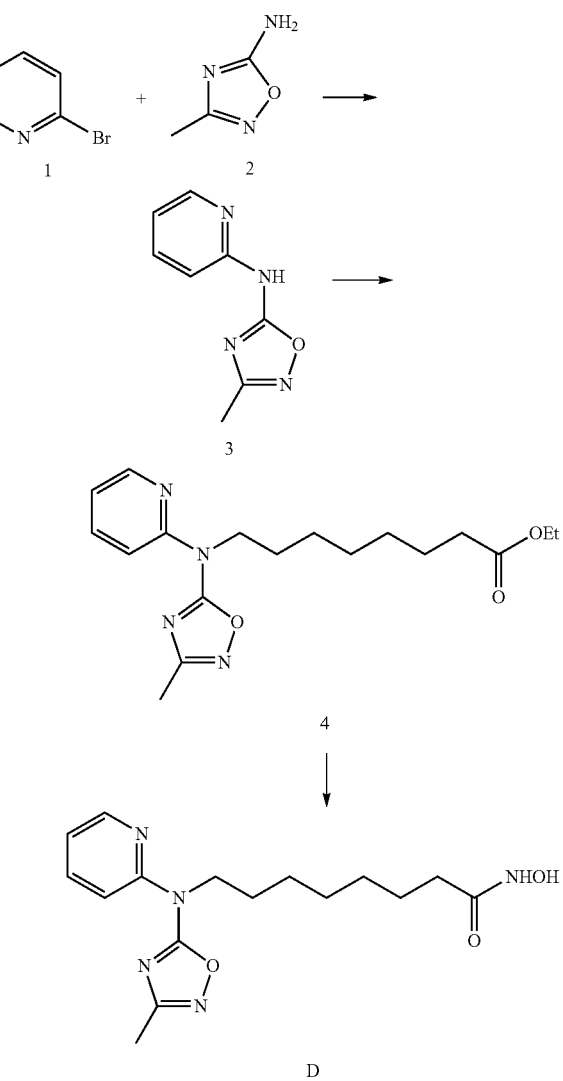

i. Ethyl 8-iodooctanoate

A mixture of ethyl 8-bromooctanoate (5 g, 19.9 mmol) and sodium iodide (2.98 g, 19.9 mmol) in Acetone (50 mL) was heated at 60° C. under nitrogen for 18 h. The reaction mixture was then concentrated under vacuum. Purification by silica gel column chromatography, using EtOAc/Hexane (1:90) as eluant, provided ethyl 8-iodooctanoate as a colourless liquid (5.5 g, 93.2%).

LCMS (ES): Found 299.2 [MH]+.

ii. N-hydroxy-8-((3-methyl-1,2,4-oxadiazol-5-yl) (pyridin-2-yl)amino)octanamide (D)

NaH (60%) (35 mg, 0.85 mmol) was added portion-wise to 3-methyl-N-(pyridin-2-yl)1,2,4-oxadiazol-5-amine (3) (150 mg, 0.85 mmol) in DMF (5 mL) at 5° C. under Ar(g). The reaction mixture was then stirred for 20 min, and ethyl-8-iodooctanoate (330 mg, 1.1 mmol) was then added. The reaction mixture was stirred at 80° C. under Ar(g) for 1 h in dark, then poured onto demineralized water (100 mL), and extracted with EtOAc (3×50 mL). The organic phases were combined, dried over Na$_2$SO$_4$, filtered and subsequently evaporated under vacuum. The resulting residue was purified by flash chromatography, eluting with EtOAc/Hexane (1:1) to furnish ethyl 8-((3-methyl-1,2,4-oxadiazol-5-yl)(pyridin-2-yl)amino)octanoate (4) as a white solid (134 mg, 40%).

LCMS (ES): Found 347.2 [MH]+.

A fresh solution of NH$_2$OH in MeOH was prepared [KOH (1.09 g, 19.50 mmol) in MeOH (10 mL) was added to NH$_2$OH.HCl (1.35 g, 19.50 mmol) in MeOH (10 mL) at 0° C.]. The reaction mixture was stirred for 20 min at 0° C., then filtered to remove salts; the filtrate was then added to (4) (135 mg, 0.39 mmol), and was then treated with KOH (218 mg, 3.9 mmol) solubilised in MeOH (5 mL). The reaction mixture was stirred at rt for 21 h, and then concentrated in vacuo, poured onto brine/H$_2$O (15 mL/35 mL), and extracted with EtOAc (3×300 mL). The organic phases were combined, dried over MgSO$_4$, filtered, and subsequently evaporated under vacuum. The resulting residue was purified by silica gel column chromatography, eluting with MeOH/CH$_2$Cl$_2$ (1:9) provide N-hydroxy-8-((3-methyl-1,2,4-oxadiazol-5-yl)(pyridin-2-yl)amino)octanamide, Example D, as a yellow solid (12.2 mg, 40%).

$^1$H NMR (400 MHz, METHANOL-d$_4$) δ: 8.44 (dt, J=4.7, 1.4 Hz, 1H), 7.82-7.87 (m, 2H), 7.21 (td, J=5.1, 2.9 Hz, 1H), 4.16-4.25 (m, 2H), 2.26 (s, 3H), 2.06 (t, J=7.4 Hz, 2H), 1.66-1.76 (m, 2H), 1.53-1.64 (m, 2H), 1.30-1.41 (m, 6H).

LCMS (ES): Found 334.3 [MH]+.

Example E

N-Hydroxy-7-((1-methyl-1H-pyrazol-3-yl)(pyridin-2-yl)amino)heptanamide

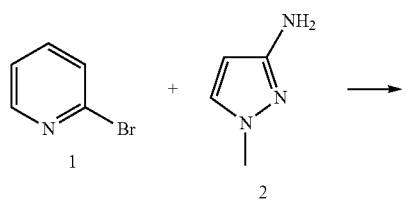

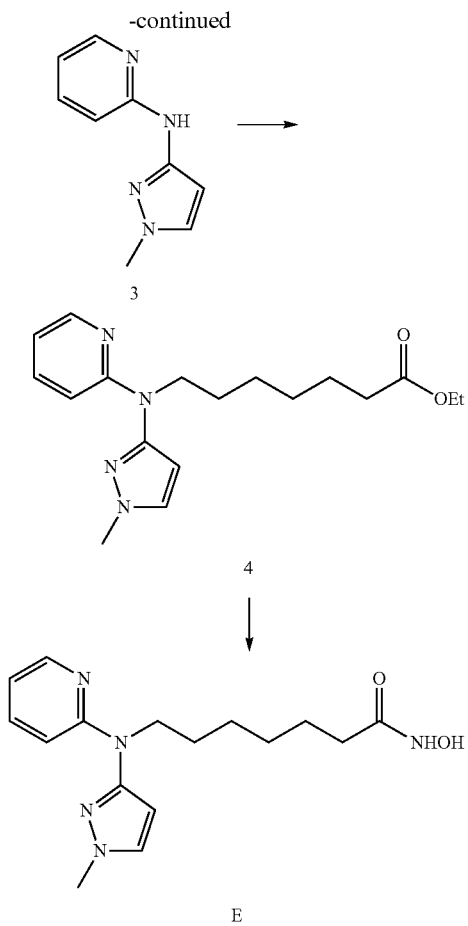

2-Bromopyridine (1) (1.0 g, 6.3 mmol), 1-methyl-1H-pyrazol-3-amine (2) (0.79 g, 8.2 mmol), Xantphos (0.37 g, 0.63 mmol), and Cs$_2$CO$_3$ (4.1 g, 12.6 mmol) were combined in dry 1,4-dioxane (15 mL). The reaction mixture was then degassed with N$_2$(g), and placed under vacuum for 10 min. Pd$_2$(dba)$_3$ (0.29 g, 0.31 mmol) was added and the resulting reaction mixture was heated at 90° C. for 30 h. It was then poured onto demineralized water (200 mL), and extracted with EtOAc (3×100 mL). The organic phases were combined, dried over Na$_2$SO$_4$, filtered and subsequently evaporated under vacuum. The resulting residue was purified by flash chromatography, eluting with EtOAc/Hexane (1:1) to provide N-(1-methyl-1H-pyrazol-3-yl)pyridin-2-amine (3) as a yellow solid (0.75 g, 68%).

LCMS (ES): Found 175.2 [MH]$^+$.

NaH (60%) (48 mg, 1.2 mmol) was added portion-wise to N-(1-methyl-1H-pyrazol-3-yl)pyridin-2-amine (3) (200 mg, 1.1 mmol) in DMF (8 mL) at 5° C. under Ar(g). The resulting reaction mixture was stirred for 20 min, and ethyl-7-iodoheptanoate (428 mg, 1.5 mmol) was added. The reaction mixture was then stirred at 70° C. under Ar(g) for 1 h in the dark; it was then poured onto demineralized water (100 mL), and extracted with EtOAc (3×50 mL). The organic phases were combined, dried over Na$_2$SO$_4$, filtered and subsequently evaporated under vacuum. The resulting residue was purified by flash chromatography, eluting with EtOAc/Hexane (3:7) to furnish ethyl 7-((1-methyl-1H-pyrazol-3-yl)(pyridin-2-yl)amino)heptanoate (4) as a yellow solid (170 mg, 44%).

LCMS (ES): Found 331.4 [MH]+.

A fresh solution of NH₂OH in MeOH was prepared [KOH (1.44 g, 25.7 mmol) in MeOH (5 mL) was added to NH₂OH.HCl (1.7 g, 25.7 mmol) in MeOH (15 mL) at 0° C.]. The reaction mixture was stirred for 20 min at 0° C., then filtered to remove salts; it was then added to (4) (170 mg, 0.51 mmol), and was then treated with KOH (288 mg, 5.1 mmol) solubilised in MeOH (5 mL). The reaction mixture was stirred at it for 21 h, and then concentrated in vacuo (ca. 200 mL), poured onto brine/H₂O (30 mL/70 mL), and extracted with CH₂Cl₂ (3×50 mL). The organic phases were combined, dried over MgSO₄, filtered, and subsequently evaporated under vacuum. The resulting residue was purified by silica gel column chromatography, eluting with MeOH/CH₂Cl₂ (1:9) to provide N-hydroxy-7-((1-methyl-1H-pyrazol-3-yl)(pyridin-2-yl)amino)heptanamide, Example E, as a yellow liquid (45 mg, 26%).

¹H NMR (400 MHz, DMSO-d₅) δ: 10.32 (br. s, 1H), 8.66 (br. s., 1H), 8.14 (dd, J=4.8, 1.1 Hz, 1H), 7.68 (d, J=2.1 Hz, 1H), 7.44 (t, J=7.0 Hz, 1H), 6.79 (d, J=8.5 Hz, 1H), 6.65 (dd, J=6.4, 5.3 Hz, 1H), 6.12 (d, J=2.1 Hz, 1H), 3.82-3.90 (m, 2H), 3.79 (s, 3H), 1.91 (t, J=7.4 Hz, 2H), 1.55 (br. s, 1H), 1.39-1.50 (m, 2H), 1.11-1.33 (m, 4H).

LCMS (ES): Found 318.2 [MH]⁺.

Example F

N-Hydroxy-8-((1-methyl-1H-pyrazol-3-yl)(pyridin-2-yl)amino)octanamide

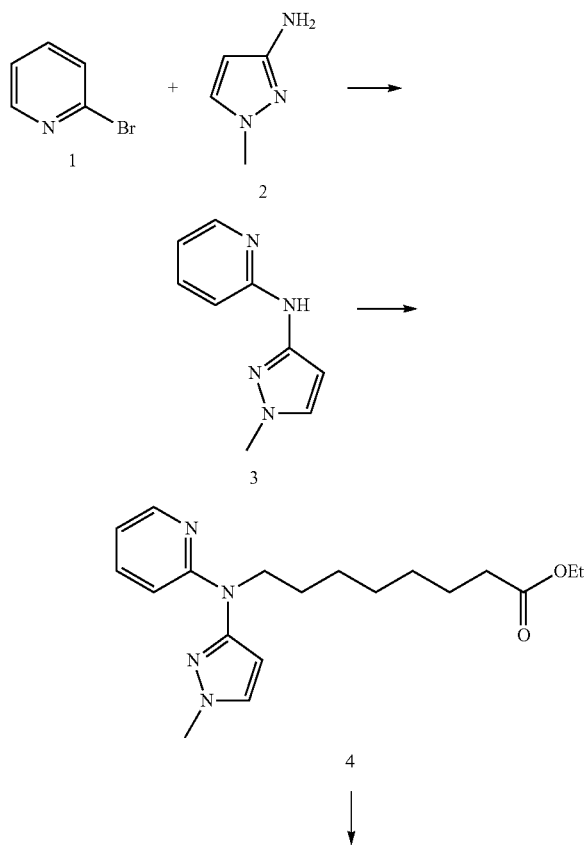

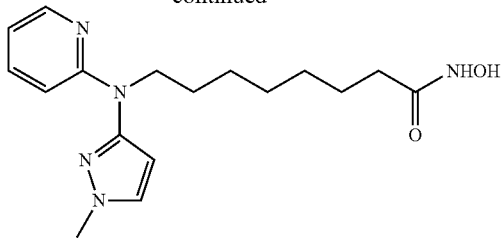

F

2-Bromopyridine (1) (1.0 g, 6.3 mmol), 1-methyl-1H-pyrazol-3-amine (2) (0.79 g, 8.2 mmol), Xantphos (0.366 g, 0.63 mmol), and Cs₂CO₃ (4.1 g, 12.6 mmol) were combined in dry 1,4-dioxane (15 mL). The reaction mixture was degassed with N₂(g) and placed under vacuum for 10 min. Pd₂(dba)₃ (0.289 g, 0.31 mmol) was then added and the resulting reaction mixture was then heated at 90° C. for 30 h. It was then poured onto demineralized water (200 mL), and extracted with EtOAc (3×100 mL). The organic phases were combined, dried over Na₂SO₄, filtered and subsequently evaporated under vacuum. The resulting residue was purified by flash chromatography, eluting with EtOAc/Hexane (1:1) to provide N-(1-methyl-1H-pyrazol-3-yl)pyridin-2-amine (3) as a yellow solid (0.75 g, 68%).

LCMS (ES): Found 175.2 [MH]⁺.

NaH (60%) (60.3 mg, 1.5 mmol) was added portion-wise to (3) (250 mg, 1.4 mmol) in DMF (10 mL) at 5° C. under Ar(g). The reaction mixture was then stirred for 20 min, and ethyl-8-iodooctanoate (556 mg, 1.8 mmol) was added. It was then stirred at 70° C. under Ar(g) for 1 h in dark, then poured onto demineralized water (100 mL), and extracted with EtOAc (3×50 mL). The organic phases were combined, dried over Na₂SO₄, filtered and subsequently evaporated under vacuum. The resulting residue was purified by flash chromatography, eluting with EtOAc/Hexane (3:70) to furnish ethyl 8-((1-methyl-1H-pyrazol-3-yl)(pyridin-2-yl)amino)octanoate (4) as a yellow solid (60 mg, 20%).

LCMS (ES): Found 345.2 [MH]+.

A fresh solution of NH₂OH in MeOH was prepared [KOH (578 mg, 10.3 mmol) in MeOH (10 mL) was added to NH₂OH.HCl (716 mg, 10.3 mmol) in MeOH (10 mL) at 0° C.]. The reaction mixture was stirred for 20 min at 0° C., then filtered to remove salts; the filtrate was then added to (4) (71 mg, 0.20 mmol), and was then treated with KOH (115 mg, 2.06 mmol) solubilised in MeOH (5 mL). The reaction mixture was stirred at rt for 21 h, and then concentrated in vacuo, poured onto brine/H₂O (30 mL/70 mL), and extracted with CH₂Cl₂ (3×50 mL). The organic phases were combined, dried over MgSO₄, filtered, and subsequently evaporated under vacuum. The resulting residue was purified by silica gel column chromatography, eluting with MeOH/CH₂Cl₂ (1:9) to provide N-hydroxy-8-((1-methyl-1H-pyrazol-3-yl)(pyridin-2-yl)amino)octanamide, Example F, as a light yellow semi solid (15 mg, 21%).

¹H NMR (400 MHz, METHANOL-d₄) δ: 8.08 (d, J=4.0 Hz, 1H), 7.60 (d, J=2.1 Hz, 1H), 7.39-7.47 (m, 1H), 6.62-6.74 (m, 2H), 6.12 (d, J=2.1 Hz, 1H), 3.82-3.91 (m, 5H), 2.07 (t, J=7.4 Hz, 2H), 1.51-1.70 (m, 4H), 1.22-1.40 (m, 6H).

LCMS (ES): Found 332.2 [MH]+.

Example G

N-Hydroxy-7-(pyridin-2-yl(1,3,4-thiadiazol-2-yl)amino)heptanamide

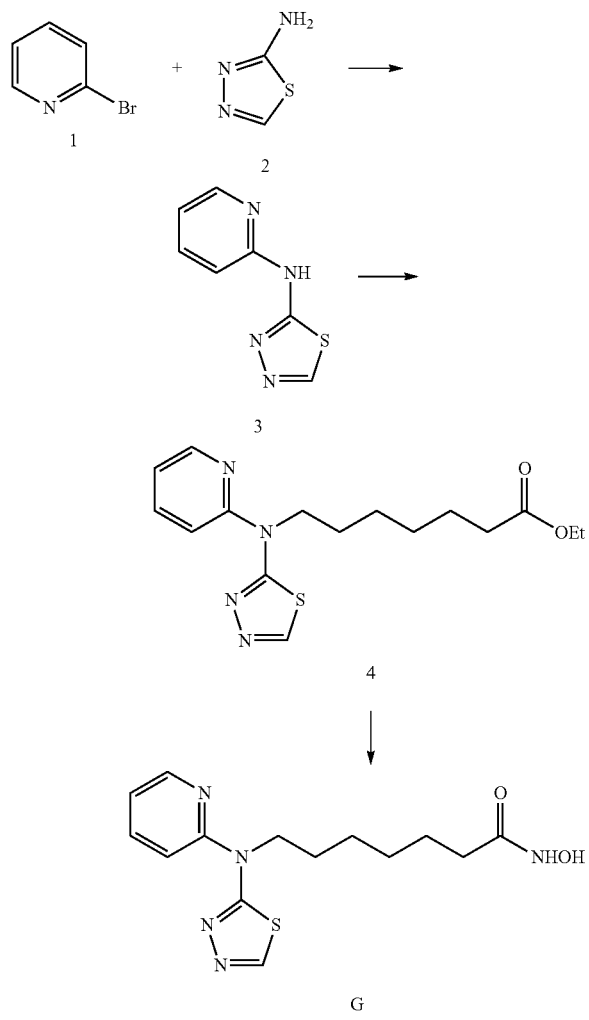

2-Bromopyridine (1) (1.0 g, 6.3 mmol), 1,3,4-thiadiazol-2-amine (2) (0.64 g, 6.3 mmol), Xantphos (0.366 g, 0.63 mmol), and Cs$_2$CO$_3$ (3.09 g, 9.4 mmol) were combined in dry 1,4-dioxane (15 mL). The reaction mixture was degassed with N$_2$(g) and placed under vacuum for 10 min. Pd$_2$(dba)$_3$ (0.289 g, 0.31 mmol) was then added and the resulting reaction mixture was then heated at 90° C. for 30 h. It was then poured onto demineralized water (200 mL), and extracted with EtOAc (3×100 mL). The organic phases were combined, dried over Na$_2$SO$_4$, filtered and subsequently evaporated under vacuum. The resulting residue was purified by flash chromatography, eluting with EtOAc/Hexane (1:1) to provide N-(pyridin-2-yl)-1,3,4-thiadiazol-2-amine (3) as a yellow solid (0.33 g, 30%).

LCMS (ES): Found 179.0 [MH]+.

NaH (60%) (32.8 mg, 0.8 mmol) was added portion-wise to (3) (126 mg, 0.78 mmol) in DMF (5 mL) at 5° C. under Ar(g). The reaction mixture was then stirred for 20 min, and ethyl-7-iodoheptanoate (288 mg, 1.0 mmol) was added. The reaction mixture was stirred at 70° C. under Ar(g) for 1 h in the dark, then poured onto demineralized water (100 mL), and extracted with EtOAc (3×50 mL). The organic phases were combined, dried over Na$_2$SO$_4$, filtered and subsequently evaporated under vacuum. The resulting residue was purified by flash chromatography, eluting with EtOAc/Hexane (3:7) to furnish ethyl 7-(pyridin-2-yl(1,3,4-thiadiazol-2-yl)amino)heptanoate as a yellowish semi solid (110 mg, 44%).

LCMS (ES): Found 335.2 [MH]+.

A fresh solution of NH$_2$OH in MeOH was prepared: [KOH (1.84 g, 32.9 mmol) in MeOH (15 mL) was added to NH$_2$OH.HCl (2.28 g, 32.9 mmol) in MeOH (15 mL) at 0° C.]. The mixture was stirred for 20 min at 0° C., then filtered to remove salts; the filtrate was then added to ethyl 7-(pyridin-2-yl(1,3,4-thiadiazol-2-yl)amino)heptanoate (4) (220 mg, 0.65 mmol) followed by KOH (369 mg, 6.58 mmol) solubilized in MeOH (5 mL). The reaction mixture was stirred at it for 21 h, then concentrated in vacuo, poured onto brine/H$_2$O (30 mL/70 mL), and extracted with CH$_2$Cl$_2$ (3×50 mL). The organic phases were combined, dried over Na$_2$SO$_4$, filtered and subsequently evaporated under vacuum. The resulting residue was purified by flash chromatography, eluting with MeOH/CH$_2$Cl$_2$ 1:9) to provide N-hydroxy-7-(pyridin-2-yl(1,3,4-thiadiazol-2-yl)amino)heptanamide, Example G, as a yellow liquid (7 mg, 3%).

$^1$H NMR (400 MHz, METHANOL-d$_4$) δ: 8.89 (s, 1H), 8.41 (dd, J=4.8, 1.0 Hz, 1H), 7.88 (ddd, J=8.6, 7.2, 1.8 Hz, 1H), 7.30 (d, J=8.5 Hz, 1H), 7.09 (dd, J=7.0, 5.0 Hz, 1H), 4.37-4.48 (m, 2H), 2.10 (t, J=7.4 Hz, 2H), 1.82 (dt, J=15.0, 7.6 Hz, 2H), 1.64 (dt, J=14.5, 7.3 Hz, 2H), 1.37-1.54 (m, 4H).

LCMS (ES): Found 322.1 [MH]+.

Example H

N-Hydroxy-8-(pyridin-2-yl(1,3,4-thiadiazol-2-yl)amino)octanamide

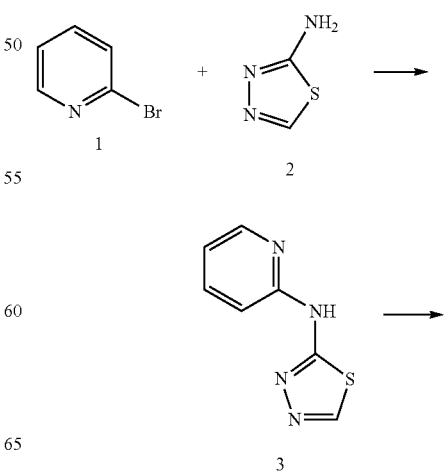

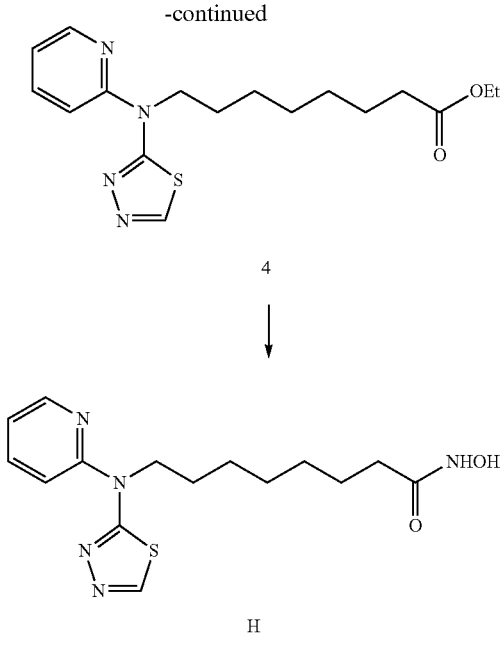

NaH (60%) (41.0 mg, 1.03 mmol) was added portion-wise to N-(pyridin-2-yl)-1,3,4-thiadiazol-2-amine (3) (as per Example G above) (176 mg, 0.98 mmol) in DMF (5 mL) at 5° C. under Ar(g). The reaction mixture was then stirred for 20 min, and ethyl-8-iodooctanoate (382 mg, 1.2 mmol) was added. The reaction mixture was stirred at 70° C. under Ar(g) for 1 h in the dark, then poured onto demineralized water (100 mL), and extracted with EtOAc (3×50 mL). The organic phases were combined, dried over $Na_2SO_4$, filtered and subsequently evaporated under vacuum. The resulting residue was purified by flash chromatography, eluting with EtOAc/Hexane (3:7) to furnish ethyl 8-(pyridin-2-yl(1,3,4-thiadiazol-2-yl)amino)octanoate (4) as a yellow solid (66 mg, 19%).

LCMS (ES): Found 349.1 [MH]+.

A fresh solution of $NH_2OH$ in MeOH was prepared: [KOH (531 mg, 9.46 mmol) in MeOH (10 mL) was added to $NH_2OH \cdot HCl$ (657 mg, 9.46 mmol) in MeOH (10 mL) at 0° C.]. The mixture was stirred for 20 min at 0° C., then filtered to remove salts; the filtrate was then added to ethyl 8-(pyridin-2-yl(1,3,4-thiadiazol-2-yl)amino)octanoate (4) (66 mg, 0.18 mmol) followed by KOH (106 mg, 1.8 mmol) solubilized in MeOH (5 mL). The reaction mixture was stirred at it for 21 h, then concentrated in vacuo, poured onto brine/$H_2O$ (30 mL/70 mL), and extracted with $CH_2Cl_2$ (3×50 mL). The organic phases were combined, dried over $Na_2SO_4$, filtered and subsequently evaporated under vacuum. The resulting residue was purified by flash chromatography, eluting with MeOH/$CH_2Cl_2$ (1:9) to provide N-hydroxy-8-(pyridin-2-yl(1,3,4-thiadiazol-2-yl)amino)oc-tanamide, Example H, as a light yellow solid (15 mg, 23%).

$^1$H NMR (400 MHz, METHANOL-$d_4$) δ: 8.89 (s, 1H), 8.40 (dd, J=4.7, 0.9 Hz, 1H), 7.79-7.94 (m, 1H), 7.29 (d, J=8.6 Hz, 1H), 7.08 (dd, J=7.1, 5.0 Hz, 1H), 4.42 (t, J=7.8 Hz, 2H), 2.09 (t, J=7.3 Hz, 2H), 1.81 (quin, J=7.2 Hz, 2H), 1.62 (quin, J=7.3 Hz, 2H), 1.24-1.52 (m, 6H).

LCMS (ES): Found 336.1[MH]+.

Example I

N-Hydroxy-7-((5-methyl-1,3,4-thiadiazol-2-yl)(pyridin-2-yl)amino)heptanamide 2-Bromopyridine (1) (1.0 g, 6.3 mmol), 5-methyl-1,3,4-thiadiazol-2-amine (2) (0.947 g, 8.2 mmol), Xantphos (0.366 g, 0.63 mmol), and $Cs_2CO_3$ (3.09 g, 9.4 mmol) were combined in dry 1,4-dioxane (15 mL). The reaction mixture was degassed with $N_2$(g) and placed under vacuum for 10 min. $Pd_2(dba)_3$ (0.289 g, 0.31 mmol) was then added and the resulting reaction mixture was heated at 90° C. for 30 h. It was then poured onto demineralized water (200 mL), and extracted with EtOAc (3×100 mL). The organic phases were combined, dried over $Na_2SO_4$, filtered and subsequently evaporated under vacuum. The resulting residue was purified by flash chromatography, eluting with EtOAc/Hexane (1:1) to provide 5-methyl-N-(pyridin-2-yl)-1,3,4-thiadiazol-2-amine (3) as a yellow solid (0.22 g, 18%).

LCMS (ES): Found 193.2 [MH]+.

NaH (60%) (43.7 mg, 1.0 mmol) was added portion-wise to 5-methyl-N-(pyridin-2-yl)-1,3,4-thiadiazol-2-amine (3)

(220 mg, 1.0 mmol) in DMF (5 mL) at 5° C. under Ar(g). The reaction mixture was then stirred for 20 min, and ethyl-7-iodoheptanoate (403 mg, 1.3 mmol) was added. The reaction mixture was stirred at 70° C. under Ar(g) for 1 h in the dark, then poured onto demineralized water (100 mL), and extracted with EtOAc (3×50 mL). The organic phases were combined, dried over Na₂SO₄, filtered and subsequently evaporated under vacuum. The resulting residue was purified by flash chromatography, eluting with EtOAc/Hexane (3:7) to furnish ethyl 7-((5-methyl-1,3,4-thiadiazol-2-yl)(pyridin-2-yl)amino)heptanoate (4) as a yellow solid (128 mg, 33%).

LCMS (ES): Found 349.1 [MH]+.

A fresh solution of NH₂OH in MeOH was prepared: [KOH (1.03 g, 18.5 mmol) in MeOH (15 mL) was added to NH₂OH.HCl (1.28 g, 18.5 mmol) in MeOH (15 mL) at 0° C.]. The mixture was stirred for 20 min at 0° C., then filtered to remove salts; the filtrate was then added to ethyl 7-((5-methyl-1,3,4-thiadiazol-2-yl)(pyridin-2-yl)amino)heptanoate (4) (128 mg, 0.37 mmol) followed by KOH (207 mg, 3.7 mmol) solubilized in MeOH (5 mL). The reaction mixture was stirred at it for 21 h, then concentrated in vacuo, poured onto brine/H₂O (30 mL/70 mL), and extracted with CH₂Cl₂ (3×50 mL). The organic phases were combined, dried over Na₂SO₄, filtered and subsequently evaporated under vacuum. The resulting residue was purified by flash chromatography, eluting with MeOH/CH₂Cl₂ (1:9) to provide N-hydroxy-7-((5-methyl-1,3,4-thiadiazol-2-yl)(pyridin-2-yl)amino)heptanamide, Example I, as a light yellow liquid (22 mg, 17.8%).

$^1$H NMR (400 MHz, METHANOL-$d_4$) δ: 8.38 (dd, J=4.9, 1.0 Hz, 1H), 7.86 (ddd, J=8.7, 7.2, 1.8 Hz, 1H), 7.26 (d, J=8.6 Hz, 1H), 7.06 (dd, J=6.9, 5.0 Hz, 1H), 4.31-4.41 (m, 2H), 3.63-3.70 (m, 1H), 3.52-3.58 (m, 1H), 2.62 (s, 3H), 2.10 (t, J=7.4 Hz, 2H), 1.80 (dt, J=15.1, 7.6 Hz, 2H), 1.64 (dt, J=14.5, 7.4 Hz, 2H), 1.37-1.53 (m, 2H).

LCMS (ES): Found 336.4 [MH]+.

Example J

N-Hydroxy-8-((5-methyl-1,3,4-thiadiazol-2-yl)(pyridin-2-yl)amino)octanamide

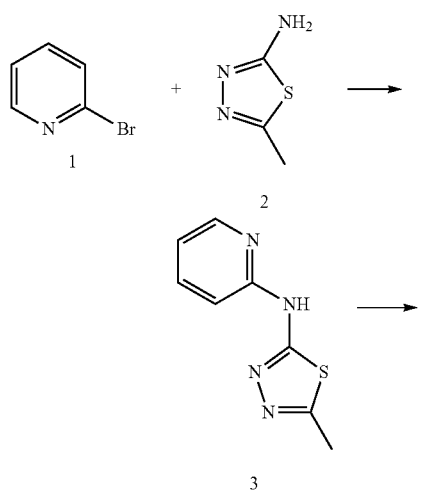

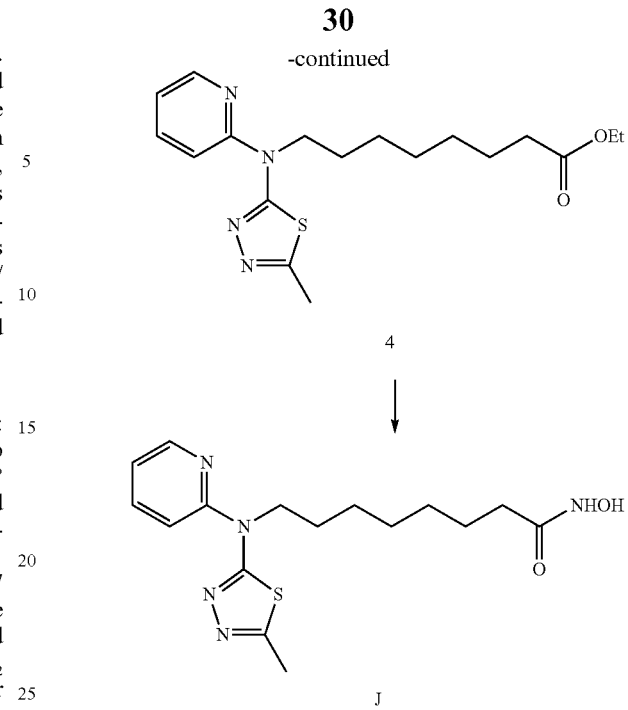

NaH (60%) (42.0 mg, 1.0 mmol) was added portion-wise to 5-methyl-N-(pyridin-2-yl)-1,3,4-thiadiazol-2-amine (3) (as per Example I above) (195 mg, 1.0 mmol) in DMF (5 mL) at 5° C. under Ar(g). The reaction mixture was then stirred for 20 min, and ethyl-8-iodooctanoate (393 mg, 1.3 mmol) was added. The reaction mixture was stirred at 70° C. under Ar(g) for 1 h in the dark, then poured onto demineralized water (100 mL), and extracted with EtOAc (3×50 mL). The organic phases were combined, dried over Na₂SO₄, filtered and subsequently evaporated under vacuum. The resulting residue was purified by flash chromatography, eluting with EtOAc/Hexane (3:7) to furnish (4) as a yellow solid (76 mg, 20%).

LCMS (ES): Found 362.5 [MH]+.

A fresh solution of NH₂OH in MeOH was prepared: [KOH (588 mg, 10.4 mmol) in MeOH (10 mL) was added to NH₂OH.HCl (729 mg, 10.4 mmol) in MeOH (10 mL) at 0° C.]. The mixture was stirred for 20 min at 0° C., then filtered to remove salts; the filtrate was then added to ethyl 8-((5-methyl-1,3,4-thiadiazol-2-yl)(pyridin-2-yl)amino)octanoate (4) (76 mg, 0.2 mmol) followed by KOH (117 mg, 2.0 mmol) solubilized in MeOH (5 mL). The reaction mixture was stirred at it for 21 h, then concentrated in vacuo, poured onto brine/H₂O (30 mL/70 mL), and extracted with CH₂Cl₂ (3×50 mL). The organic phases were combined, dried over Na₂SO₄, filtered and subsequently evaporated under vacuum. The resulting residue was purified by flash chromatography, eluting with MeOH/CH₂Cl₂ (1:9) to provide N-hydroxy-8-((5-methyl-1,3,4-thiadiazol-2-yl)(pyridin-2-yl)amino)octanamide, Example J, as a light yellow solid (8 mg, 11%).

$^1$H NMR (METHANOL-$d_4$) δ: 8.38 (ddd, J=4.9, 1.8, 0.9 Hz, 1H), 7.86 (ddd, J=8.7, 7.1, 1.9 Hz, 1H), 7.26 (d, J=8.6 Hz, 1H), 7.06 (ddd, J=7.2, 4.9, 0.6 Hz, 1H), 4.32-4.40 (m, 2H), 2.62 (s, 3H), 2.09 (t, J=7.4 Hz, 2H), 1.80 (quin, J=7.5 Hz, 2H), 1.62 (quin, J=7.4 Hz, 2H), 1.32-1.51 (m, 6H).

LCMS (ES): Found 350.1 [MH]+.

Example K 7-(Benzo[d]oxazol-2-yl(pyridin-2-yl)amino)-N-hydroxyheptanamide

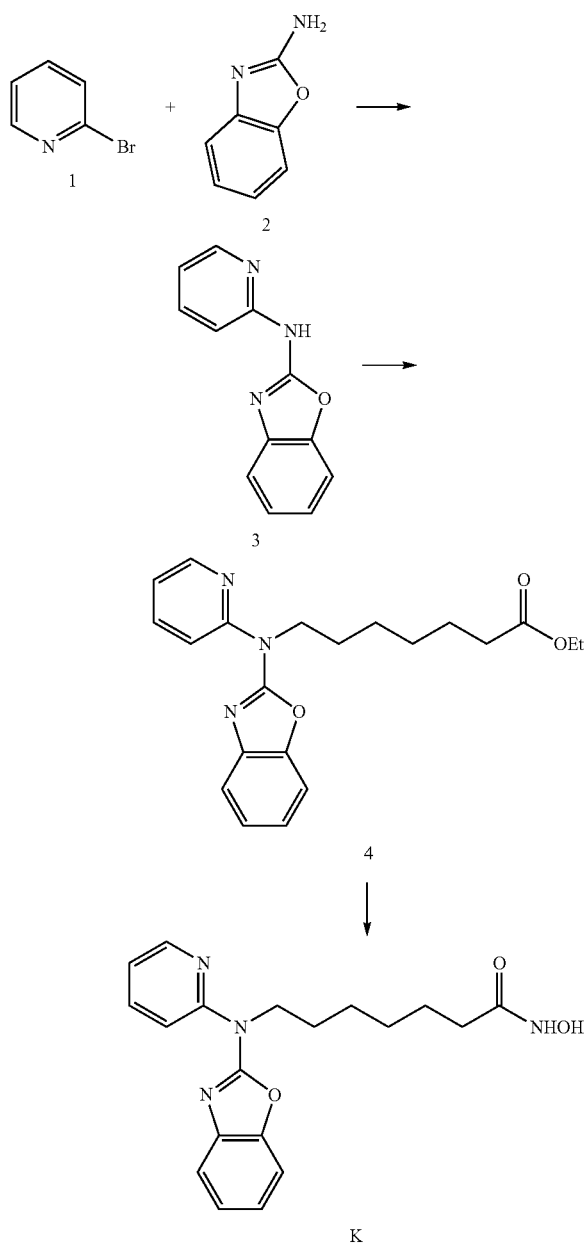

2-Bromopyridine (1) (1.0 g, 6.3 mmol), benzo[d]oxazol-2-amine (2) (0.871 g, 6.4 mmol), Xantphos (0.366 g, 0.63 mmol), and Cs$_2$CO$_3$ (3.09 g, 9.4 mmol) were combined in dry 1,4-dioxane (15 mL). The reaction mixture was degassed with N$_2$(g) and placed under vacuum for 10 min. Pd$_2$(dba)$_3$ (0.289 g, 0.31 mmol) was then added and the resulting reaction mixture was heated at 90° C. for 30 h. It was then poured onto demineralized water (200 mL), and extracted with EtOAc (3×100 mL). The organic phases were combined, dried over Na$_2$SO$_4$, filtered and subsequently evaporated under vacuum. The resulting residue was purified by flash chromatography, eluting with EtOAc/Hexane (1:1) to provide N-(pyridin-2-yl)benzo[d]oxazol-2-amine (3) as a yellow solid (0.8 g, 60%).

LCMS (ES): Found 212.1 [MH]+.

NaH (60%) (35.3 mg, 0.50 mmol) was added portionwise to N-(pyridin-2-yl)benzo[d]oxazol-2-amine (3) (162 mg, 0.48 mmol) in DMF (5 mL) at 5° C. under Ar(g). The reaction mixture was then stirred for 20 min, and ethyl-7-iodoheptanoate (179 mg, 1.3 mmol) was added. The reaction mixture was stirred at 70° C. under Ar(g) for 1 h in the dark, then poured onto demineralized water (100 mL), and extracted with EtOAc (3×50 mL). The organic phases were combined, dried over Na$_2$SO$_4$, filtered and subsequently evaporated under vacuum. The resulting residue was purified by flash chromatography, eluting with EtOAc/Hexane (3:7) to furnish ethyl 7-(benzo[d]oxazol-2-yl(pyridin-2-yl)amino)heptanoate as a yellow solid (80 mg, 28%).

LCMS (ES): Found 368.1 [MH]+.

A fresh solution of NH$_2$OH in MeOH was prepared: [KOH (1.06 g, 18.9 mmol) in MeOH (15 mL) was added to NH$_2$OH.HCl (1.31 g, 18.9 mmol) in MeOH (15 mL) at 0° C.]. The mixture was stirred for 20 min at 0° C., then filtered to remove salts; the filtrate was then added to ethyl 7-(benzo[d]oxazol-2-yl(pyridin-2-yl)amino)heptanoate (3) (80 mg, 0.37 mmol) followed by KOH (212 mg, 3.7 mmol) solubilized in MeOH (5 mL). The reaction mixture was stirred at it for 21 h, then concentrated in vacuo, poured onto brine/H$_2$O (30 mL/70 mL), and extracted with CH$_2$Cl$_2$ (3×50 mL). The organic phases were combined, dried over Na$_2$SO$_4$, filtered and subsequently evaporated under vacuum. The resulting residue was purified by flash chromatography, eluting with MeOH/CH$_2$Cl$_2$ (1:9) to provide 7-(benzo[d]oxazol-2-yl(pyridin-2-yl)amino)-N-hydroxyheptanamide, Example K, as an off-white liquid (20 mg, 25%).

$^1$H NMR (400 MHz, METHANOL-d$_4$) δ: 8.43-8.47 (m, 1H), 7.84-7.88 (m, 2H), 7.39-7.44 (m, 2H), 7.25 (td, J=7.7, 1.1 Hz, 1H), 7.21 (ddd, J=5.9, 5.0, 2.4 Hz, 1H), 7.13-7.19 (m, 1H), 4.24-4.32 (m, 2H), 2.07 (t, J=7.4 Hz, 2H), 1.79 (quin, J=7.4 Hz, 2H), 1.60 (dt, J=14.4, 7.2 Hz, 2H), 1.33-1.47 (m, 4H).

LCMS (ES): Found 355.4 [MH]+.

Example L 8-(Benzo[d]oxazol-2-yl(pyridin-2-yl)amino)-N-hydroxyoctanamide

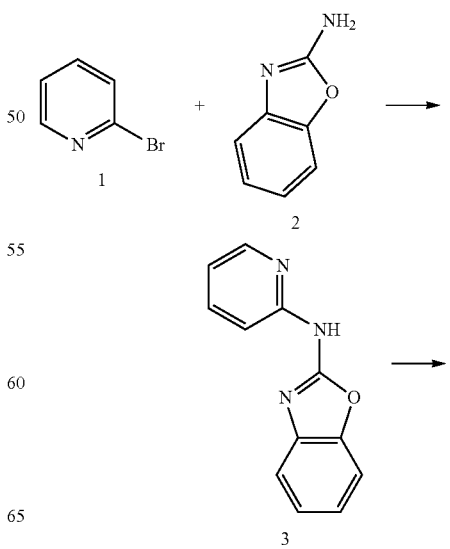

33

-continued

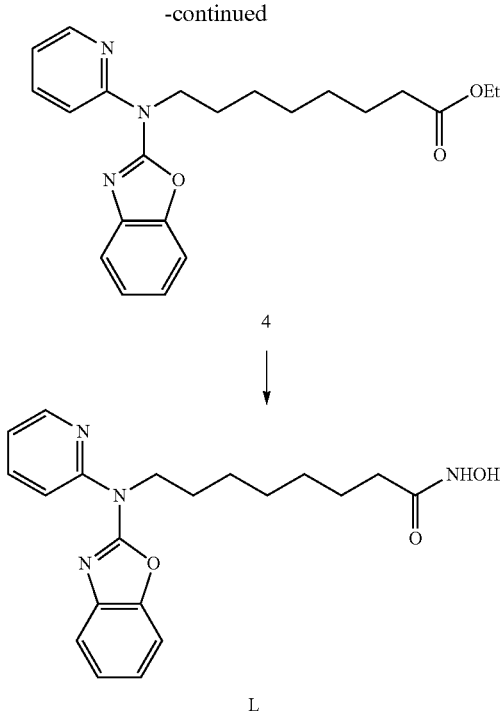

4

↓

L

NaH (60%) (53.7 mg, 1.34 mmol) was added portionwise to N-(pyridin-2-yl)benzo[d]oxazol-2-amine (3) (as per Example K above) (265 mg, 1.28 mmol) in DMF (8 mL) at 5° C. under Ar(g). The reaction mixture was then stirred for 20 min, and ethyl-8-iodooctanoate (495 mg, 1.66 mmol) was added. The reaction mixture was stirred at 70° C. under Ar(g) for 1 h in the dark, then poured onto demineralized water (100 mL), and extracted with EtOAc (3×50 mL). The organic phases were combined, dried over $Na_2SO_4$, filtered and subsequently evaporated under vacuum. The resulting residue was purified by flash chromatography, eluting with EtOAc/Hexane (3:7) to furnish ethyl 8-(benzo[d]oxazol-2-yl(pyridin-2-yl)amino)octanoate (4) as a yellow solid (210 mg, 43%).

LCMS (ES): Found 382.4 [MH]+.

A fresh solution of $NH_2OH$ in MeOH was prepared: [KOH (1.56 mg, 27.8 mmol) in MeOH (15 mL) was added to $NH_2OH.HCl$ (1.94 g, 27.8 mmol) in MeOH (15 mL) at 0° C.]. The reaction mixture was stirred for 20 min at 0° C., then filtered to remove salts; the filtrate was then added to ethyl 8-(benzo[d]oxazol-2-yl(pyridin-2-yl)amino)octanoate (4) (210 mg, 0.55 mmol) followed by KOH (313 mg, 5.57 mmol) solubilized in MeOH (5 mL). The reaction mixture was stirred at it for 21 h, then concentrated in vacuo, poured onto brine/$H_2O$ (30 mL/70 mL), and extracted with $CH_2Cl_2$ (3×50 mL). The organic phases were combined, dried over $Na_2SO_4$, filtered and subsequently evaporated under vacuum. The resulting residue was purified by flash chromatography, eluting with MeOH/$CH_2Cl_2$ (1:9) to provide 8-(benzo[d]oxazol-2-yl(pyridin-2-yl)amino)-N-hydroxyoctanamide, Example L, as a light brown solid (67 mg, 33%).

$^1$H NMR (400 MHz, DMSO-$d_5$) δ: 10.33 (br. s., 1H), 8.68 (br. s., 1H), 8.46 (ddd, J=4.8, 1.8, 1.1 Hz, 1H), 8.01 (d, J=8.4 Hz, 1H), 7.88 (td, J=7.8, 2.0 Hz, 1H), 7.51 (dd, J=18.6, 7.4 Hz, 2H), 7.25 (td, J=7.7, 1.1 Hz, 1H), 7.12-7.21 (m, 2H), 4.20-4.31 (m, 2H), 1.90 (t, J=7.4 Hz, 2H), 1.64-1.75 (m, 2H), 1.45 (dt, J=14.6, 7.3 Hz, 2H), 1.14-1.36 (m, 6H).

LCMS (ES): Found 369.1 [MH]+.

34

Example M

N-Hydroxy-7-((1-methyl-1H-benzo[d]imidazol-2-yl)(pyridin-2-yl)amino)heptanamide

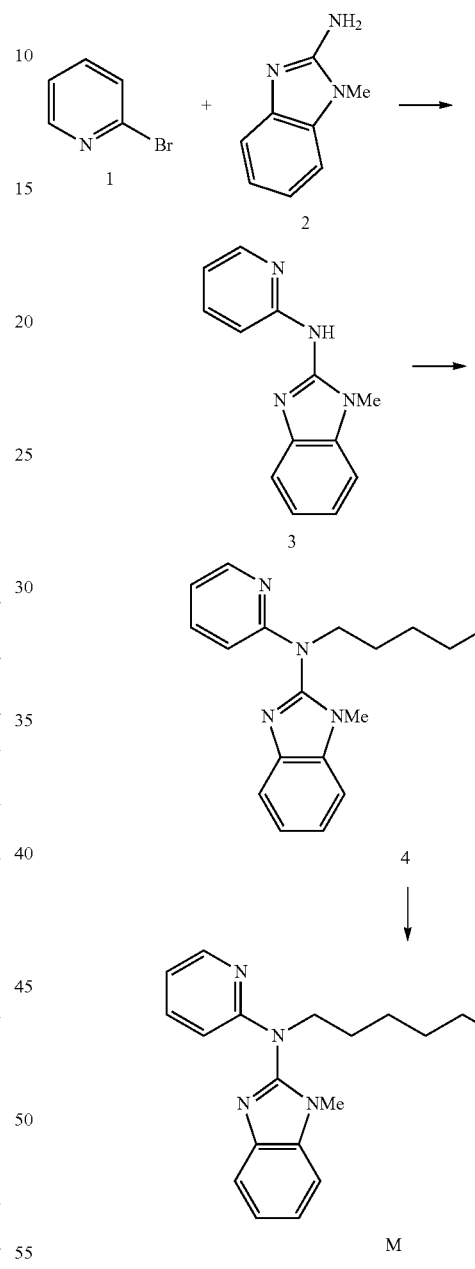

M

2-Bromopyridine (1) (1.0 g, 6.3 mmol), 2-amino-1-methylbenzimidazole (2) (1.21 g, 6.9 mmol), Xantphos (0.37 g, 0.63 mmol), and $Cs_2CO_3$ (4.1 g, 12.6 mmol) were combined in dry 1,4-dioxane (15 mL). The reaction mixture was degassed with $N_2(g)$ and placed under vacuum for 10 min. $Pd_2(dba)_3$ (0.289 g, 0.31 mmol) was then added and the resulting reaction mixture was heated at 90° C. for 30 h. It was then poured onto demineralized water (200 mL), and extracted with EtOAc (3×100 mL). The organic phases were combined, dried over $Na_2SO_4$, filtered and subsequently evaporated under vacuum. The resulting residue was purified by flash chromatography, eluting with EtOAc/Hexane (1:1) to provide 1-methyl-N-(pyridin-2-yl)-1H-benzo[d]imidazol-2-amine (3) as a yellow solid (0.35 g, 25%).

LCMS (ES): Found 225.1 [MH]+.

NaH (60%) (27 mg, 0.68 mmol) was added portion-wise to 1-methyl-N-(pyridin-2-yl)-1H-benzo[d]imidazol-2-amine (3) (147 mg, 0.65 mmol) in DMF (5 mL) at 5° C. under Ar(g). The reaction mixture was then stirred for 20 min, and ethyl-7-iodoheptanoate (242 mg, 0.84 mmol) was added. The reaction mixture was stirred at 70° C. under Ar(g) for 1 h in the dark, then poured onto demineralized water (100 mL), and extracted with EtOAc (3×50 mL). The organic phases were combined, dried over $Na_2SO_4$, filtered and subsequently evaporated under vacuum. The resulting residue was purified by flash chromatography, eluting with EtOAc/Hexane (3:7) to furnish ethyl 7-((1-methyl-1H-benzo[d]imidazol-2-yl)(pyridin-2-yl)amino)heptanoate (4) as a yellow solid (160 mg, 64%).

LCMS (ES): Found 381.2 [MH]+.

A fresh solution of $NH_2OH$ in MeOH was prepared: [KOH (0.59 g, 10.5 mmol) in MeOH (15 mL) was added to $NH_2OH.HCl$ (0.73 g, 10.5 mmol) in MeOH (15 mL) at 0° C.]. The mixture was stirred for 20 min at 0° C., then filtered to remove salts; the filtrate was then added to ethyl 7-((1-methyl-1H-benzo[d]imidazol-2-yl)(pyridin-2-yl)amino) heptanoate (4) (160 mg, 0.42 mmol) followed by KOH (236 mg, 4.2 mmol) solubilized in MeOH (5 mL). The reaction mixture was stirred at it for 21 h, then concentrated in vacuo, poured onto brine/$H_2O$ (30 mL/70 mL), and extracted with $CH_2Cl_2$ (3×50 mL). The organic phases were combined, dried over $Na_2SO_4$, filtered and subsequently evaporated under vacuum. The resulting residue was purified by flash chromatography, eluting with MeOH/$CH_2Cl_2$ (1:90) to provide N-hydroxy-7-((1-methyl-1H-benzo[d]imidazol-2-yl)(pyridin-2-yl)amino)heptanamide, Example M, as a light yellow liquid (10 mg, 6%).

$^1$H NMR (400 MHz, DMSO-$d_5$) δ: 10.32 (br. s, 1H), 8.65 (br. s, 1H), 8.15-8.20 (m, 1H), 7.60-7.64 (m, 1H), 7.58 (d, J=7.1 Hz, 1H), 7.47-7.52 (m, 1H), 7.23 (dtd, J=18.1, 7.4, 1.2 Hz, 2H), 6.86 (dd, J=7.0, 5.2 Hz, 1H), 6.57 (d, J=8.6 Hz, 1H), 3.93-4.00 (m, 2H), 3.50 (s, 3H), 1.90 (t, J=7.2 Hz, 2H), 1.59-1.70 (m, 2H), 1.40-1.50 (m, 2H), 1.28 (d, J=9.8 Hz, 4H).

LCMS (ES): Found 368.2 [MH]+

Example N

N-Hydroxy-8-((1-methyl-1H-benzo[d]imidazol-2-yl)(pyridin-2-yl)amino)octanamide

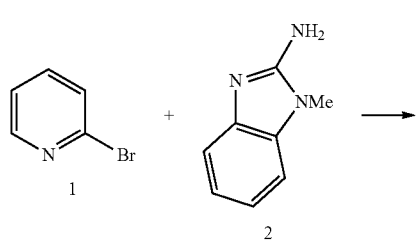

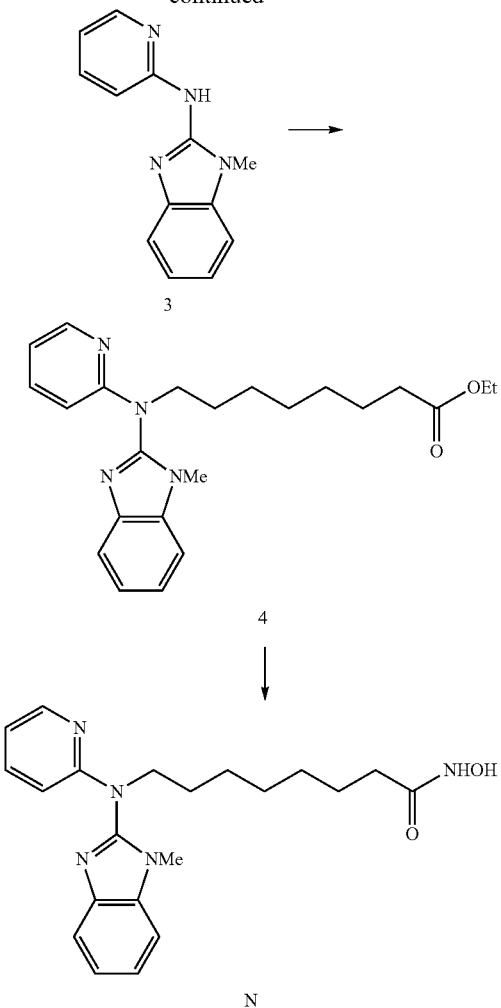

NaH (60%) (32.8 mg, 0.82 mmol) was added portion-wise to 1-methyl-N-(pyridin-2-yl)-1H-benzo[d]imidazol-2-amine (3) (as per Example M above) (175 mg, 0.78 mmol) in DMF (5 mL) at 5° C. under Ar(g). The reaction mixture was then stirred for 20 min, and ethyl-8-iodooctanoate (302 mg, 1.01 mmol) was added. The reaction mixture was stirred at 70° C. under Ar(g) for 1 h in the dark, then poured onto demineralized water (100 mL), extracted with EtOAc (3×50 mL). The organic phases were combined, dried over $Na_2SO_4$, filtered and subsequently evaporated under vacuum. The resulting residue was purified by flash chromatography, eluting with EtOAc/Hexane (3:7) to furnish ethyl 8-((1-methyl-1H-benzo[d]imidazol-2-yl)(pyridin-2-yl)amino)octanoate (4) as a yellow solid (60 mg, 19%).

LCMS (ES): Found 395.2 [MH]+.

A fresh solution of $NH_2OH$ in MeOH was prepared: [KOH (426 mg, 7.6 mmol) in MeOH (10 mL) was added to $NH_2OH.HCl$ (526 mg, 7.6 mmol) in MeOH (10 mL) at 0° C. The mixture was stirred for 20 min at 0° C., then filtered to remove salts; the filtrate was then added to ethyl 8-((1-methyl-1H-benzo[d]imidazol-2-yl)(pyridin-2-yl)amino)octanoate (4) (60 mg, 0.15 mmol) followed by KOH (85.2 mg, 1.52 mmol) solubilized in MeOH (5 mL). The reaction mixture was stirred at it for 21 h, then concentrated in vacuo, poured onto brine/$H_2O$ (30 mL/70 mL), and extracted with $CH_2Cl_2$ (3×50 mL). The organic phases were combined, dried over Na₂SO₄, filtered and subsequently evaporated under vacuum. The resulting residue was purified by flash chromatography, eluting with MeOH/CH₂Cl₂ (1:9) to provide N-hydroxy-8-((1-methyl-1H-benzo[d]imidazol-2-yl)(pyridin-2-yl)amino)octanamide, Example N, as a light yellow solid (11 mg, 18%).

¹H NMR (400 MHz, METHANOL-d₄) δ: 8.17 (d, J=4.0 Hz, 1H), 7.57-7.67 (m, 2H), 7.47 (d, J=7.6 Hz, 1H), 7.25-7.36 (m, 2H), 6.87 (dd, J=6.9, 5.2 Hz, 1H), 6.59 (d, J=8.5 Hz, 1H), 4.01-4.08 (m, 2H), 3.50 (s, 3H), 2.04 (t, J=7.4 Hz, 2H), 1.73 (quin, J=7.1 Hz, 2H), 1.56 (quin, J=7.2 Hz, 2H), 1.29-1.43 (m, 6H).

LCMS (ES): Found 382.4 [MH]+.

Example O

N-Hydroxy-7-(pyridin-2-yl(1,2,4-thiadiazol-5-yl)amino)heptanamide

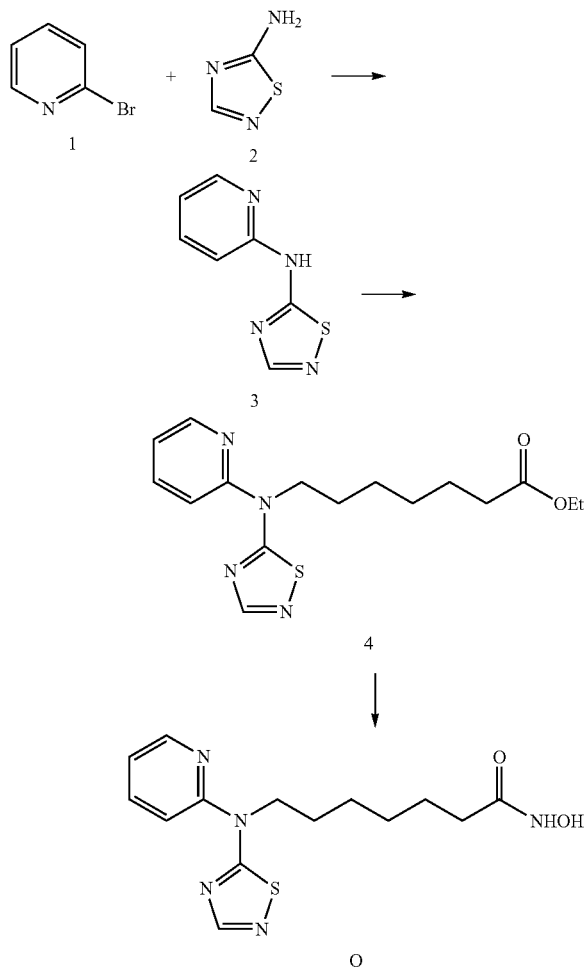

2-Bromopyridine (1) (1.0 g, 6.3 mmol), 1,2,4-thiadiazol-5-amine (2) (0.830 g, 8.22 mmol), Xantphos (0.366 g, 0.63 mmol), and Cs₂CO₃ (3.09 g, 9.4 mmol) were combined in dry 1,4-dioxane (15 mL). The reaction mixture was degassed with N₂(g) and placed under vacuum for 10 min. Pd₂(dba)₃ (0.289 g, 0.31 mmol) was then added and the resulting reaction mixture was heated at 90° C. for 30 h. It was then poured onto demineralized water (200 mL), and extracted with EtOAc (3×100 mL). The organic phases were combined, dried over Na₂SO₄, filtered and subsequently evaporated under vacuum. The resulting residue was purified by flash chromatography, eluting with EtOAc/Hexane (1:1) to provide N-(pyridin-2-yl)1,2,4-thiadiazol-5-amine (3) as a yellow solid (0.188 g, 16%).

LCMS (ES): Found 179.0 [MH]⁺

NaH (60%) (43.6 mg, 1.09 mmol) was added portionwise to N-(pyridin-2-yl)1,2,4-thiadiazol-5-amine (3) (185 mg, 1.03 mmol) in DMF (5 mL) at 5° C. under Ar(g). The reaction mixture was then stirred for 20 min, and ethyl-7-iodoheptanoate (383 mg, 1.3 mmol) was added. The reaction mixture was stirred at 70° C. under Ar(g) for 1 h in the dark, then poured onto demineralized water (100 mL), and extracted with EtOAc (3×50 mL). The organic phases were combined, dried over Na₂SO₄, filtered and subsequently evaporated under vacuum. The resulting residue was purified by flash chromatography, eluting with EtOAc/Hexane (3:7) to furnish ethyl 7-(pyridin-2-yl(1,2,4-thiadiazol-5-yl)amino)heptanoate as a yellow solid (139 mg, 39%).

LCMS (ES): Found 335.1 [MH]⁺

A fresh solution of NH₂OH in MeOH was prepared: [KOH (1.16 g, 20.8 mmol) in MeOH (15 mL) was added to NH₂OH.HCl (1.4 g, 20.8 mmol) in MeOH (15 mL) at 0° C.]. The mixture was stirred for 20 min at 0° C., then filtered to remove salts; the filtrate was then added to ethyl 7-(pyridin-2-yl(1,2,4-thiadiazol-5-yl)amino)heptanoate (4) (139 mg, 0.41 mmol) followed by KOH (233 mg, 4.1 mmol) solubilized in MeOH (5 mL). The reaction mixture was stirred at it for 21 h, then concentrated in vacuo, poured onto brine/H₂O (30 mL/70 mL), and extracted with CH₂Cl₂ (3×50 mL). The organic phases were combined, dried over Na₂SO₄, filtered and subsequently evaporated under vacuum. The resulting residue was purified by flash chromatography, eluting with MeOH/CH₂Cl₂ (1:9) to provide N-hydroxy-7-(pyridin-2-yl(1,2,4-thiadiazol-5-yl)amino)heptanamide, Example O, as an off-white liquid (13 mg, 10%).

¹H NMR (400 MHz, METHANOL-d₄) δ: 8.46-8.53 (m, 1H), 8.27 (s, 1H), 7.88-7.97 (m, 1H), 7.39 (d, J=8.5 Hz, 1H), 7.13 (dd, J=7.1, 5.0 Hz, 1H), 4.39-4.50 (m, 2H), 2.10 (t, J=7.3 Hz, 2H), 1.79 (dt, J=14.8, 7.5 Hz, 2H), 1.63 (quin, J=7.2 Hz, 2H), 1.36-1.52 (m, 4H).

LCMS (ES): Found 322.2 [MH]+.

Example P

N-Hydroxy-8-(pyridin-2-yl(1,2,4-thiadiazol-5-yl)amino)octanamide

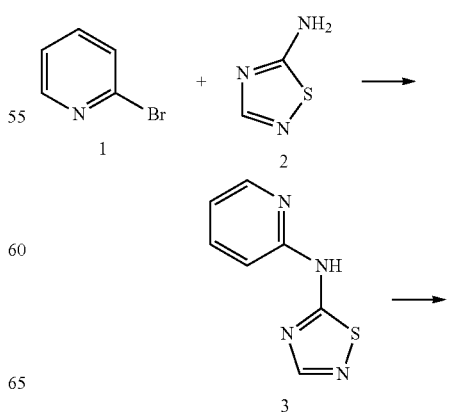

39
-continued

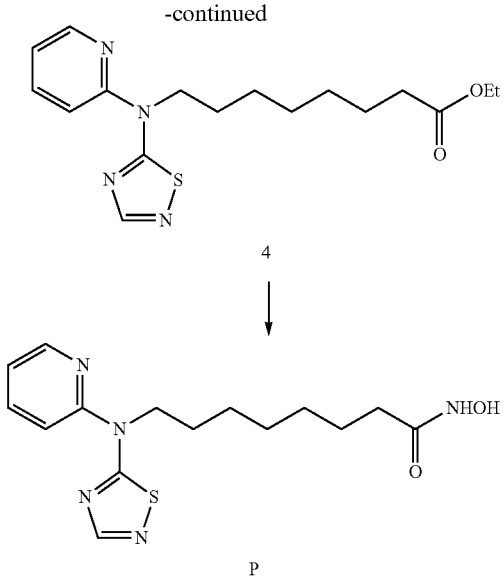

NaH (60%) (49 mg, 1.2 mmol) was added portion-wise to N-(pyridin-2-yl)1,2,4-thiadiazol-5-amine (3) (as per Example O above) (210 mg, 1.1 mmol) in DMF (8 mL) at 5° C. under Ar(g). The reaction mixture was then stirred for 20 min, and ethyl-8-iodooctanoate (561 mg, 1.5 mmol) was added. The reaction mixture was stirred at 70° C. under Ar(g) for 1 h in the dark, then poured onto demineralized water (100 mL), and extracted with EtOAc (3×50 mL). The organic phases were combined, dried over $Na_2SO_4$, filtered and subsequently evaporated under vacuum. The resulting residue was purified by flash chromatography, eluting with EtOAc/Hexane (3:7) to furnish ethyl 8-(pyridin-2-yl(1,2,4-thiadiazol-5-yl)amino)octanoate (4) as a yellow solid (140 mg, 34%).

LCMS (ES): Found 349.1 [MH]+.

A fresh solution of $NH_2OH$ in MeOH was prepared: [KOH (1.12 mg, 20.0 mmol) in MeOH (15 mL) was added to $NH_2OH.HCl$ (1.38 g, 20.0 mmol) in MeOH (15 mL) at 0° C.]. The mixture was stirred for 20 min at 0° C., then filtered to remove salts; the filtrate was then added to ethyl 8-(pyridin-2-yl(1,2,4-thiadiazol-5-yl)amino)octanoate (4) (140 mg, 0.4 mmol) followed by KOH (224 mg, 4.0 mmol) solubilized in MeOH (5 mL). The reaction mixture was stirred at it for 21 h, then concentrated in vacuo, poured onto brine/$H_2O$ (30 mL/70 mL), and extracted with $CH_2Cl_2$ (3×50 mL). The organic phases were combined, dried over $Na_2SO_4$, filtered and subsequently evaporated under vacuum. The resulting residue was purified by flash chromatography, eluting with $MeOH/CH_2Cl_2$ (1:9) to provide N-hydroxy-8-(pyridin-2-yl(1,2,4-thiadiazol-5-yl)amino)octanamide, Example P, as a light brown solid (55 mg, 41%).

$^1$H NMR (400 MHz, DMSO-$d_5$) δ: 10.34 (br. s., 1H), 8.67 (br. s., 1H), 8.54 (s, 1H), 8.31-8.43 (m, 1H), 7.90-8.06 (m, 1H), 7.45-7.59 (m, 1H), 7.14-7.27 (m, 1H), 4.44 (d, J=6.6 Hz, 2H), 3.12-3.20 (m, 2H), 1.87-2.00 (m, 2H), 1.63-1.77 (m, 2H), 1.27-1.57 (m, 6H).

LCMS (ES): Found 336.4 [MH]+

40

Example Q 7-((5-Fluoropyridin-2-yl)(3-methyl-1,2,4-oxadiazol-5-yl)amino)-N-hydroxyheptanamide

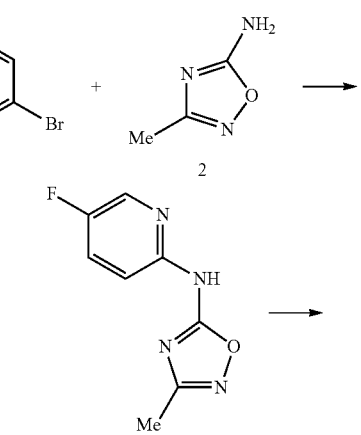

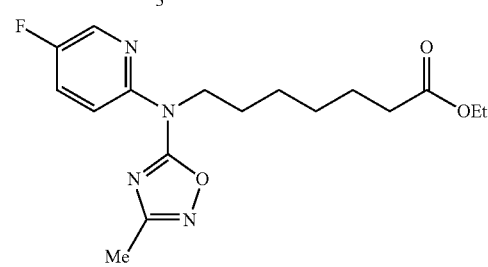

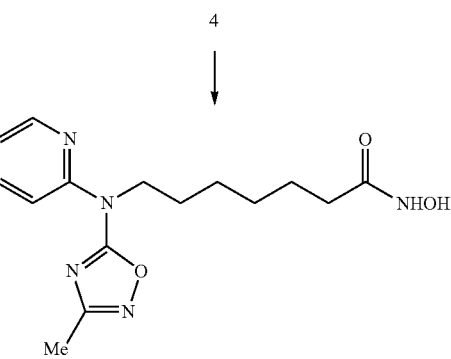

2-Bromo-5-fluoropyridine (1) (1.0 g, 5.71 mmol), 3-methyl-1,2,4-oxadiazol-5-amine (2) (566 mg, 5.71 mmol), Xantphos (0.33 g, 0.57 mmol), and $Cs_2CO_3$ (2.79 g, 8.56 mmol) were combined in dry 1,4-dioxane (15 mL). The reaction mixture was degassed with $N_2$(g) and placed under vacuum for 10 min. $Pd_2(dba)_3$ (0.26 g, 0.28 mmol) was then added and the resulting reaction mixture was heated at 90° C. for 30 h. It was then poured onto demineralized water (200 mL), and extracted with EtOAc (3×100 mL). The organic phases were combined, dried over $Na_2SO_4$, filtered and subsequently evaporated under vacuum. The resulting residue was purified by flash chromatography, eluting with EtOAc/Hexane (1:1) to provide N-(5-fluoropyridin-2-yl)-3-methyl-1,2,4-oxadiazol-5-amine (3) as a yellow solid (0.70 g, 63%).

LCMS (ES): Found 195.0 [MH]+.

NaH (60%) (43 mg, 1.08 mmol) was added portion-wise to N-(5-fluoropyridin-2-yl)-3-methyl-1,2,4-oxadiazol-5- amine (3) (200 mg, 1.03 mmol) in DMF (7 mL) at 5° C. under Ar(g). The reaction mixture was then stirred for 20 min, and ethyl-7-iodoheptanoate (380 mg, 1.3 mmol) was added. The reaction mixture was stirred at 70° C. under Ar(g) for 1 h in the dark, then poured onto demineralized water (100 mL), and extracted with EtOAc (3×50 mL). The organic phases were combined, dried over Na₂SO₄, filtered and subsequently evaporated under vacuum. The resulting residue was purified by flash chromatography, eluting with EtOAc/Hexane (3:70) to furnish ethyl 7-((5-fluoropyridin-2-yl)(3-methyl-1,2,4-oxadiazol-5-yl)amino)heptanoate (4) as a yellow solid (250 mg, 69%).

LCMS (ES): Found 351.1 [MH]⁺.

A fresh solution of NH₂OH in MeOH was prepared: [KOH (2.0 g, 35.7 mmol) in MeOH (15 mL) was added to NH₂OH.HCl (2.48 g, 35.7 mmol) in MeOH (15 mL) at 0° C.]. The mixture was stirred for 20 min at 0° C., then filtered to remove salts; the filtrate was then added to ethyl 7-((5-fluoropyridin-2-yl)(3-methyl-1,2,4-oxadiazol-5-yl)amino)heptanoate (4) (250 mg, 0.71 mmol) followed by KOH (400 mg, 7.1 mmol) solubilized in MeOH (5 mL). The reaction mixture was stirred at it for 21 h, then concentrated in vacuo, poured onto brine/H₂O (30 mL/70 mL), and extracted with CH₂Cl₂ (3×50 mL). The organic phases were combined, dried over Na₂SO₄, filtered and subsequently evaporated under vacuum. The resulting residue was purified by flash chromatography, eluting with MeOH/CH₂Cl₂ (1:9) to provide 7-((5-fluoropyridin-2-yl)(3-methyl-1,2,4-oxadiazol-5-yl)amino)-N-hydroxyheptanamide, Example Q, as an off-white solid (45 mg, 18.3%).

$^1$H NMR (400 MHz, DMSO-d₅) δ: 10.32 (br. s, 1H), 8.65 (br. s, 1H), 8.47 (d, J=3.0 Hz, 1H), 7.96 (dd, J=9.2, 3.9 Hz, 1H), 7.86 (ddd, J=9.2, 8.1, 3.1 Hz, 1H), 4.06-4.13 (m, 2H), 2.22 (s, 3H), 1.91 (t, J=7.3 Hz, 2H), 1.62 (quin, J=7.2 Hz, 2H), 1.45 (quin, J=7.2 Hz, 2H), 1.18-1.32 (m, 4H).

LCMS (ES): Found 338.5 [MH]+.

Example R 8-((5-Fluoropyridin-2-yl)(3-methyl-1,2,4-oxadiazol-5-yl)amino)-N-hydroxyoctanamide

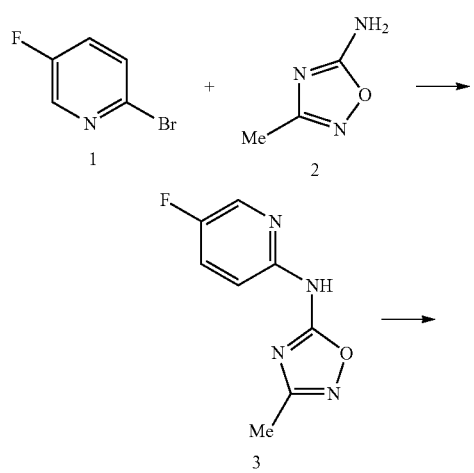

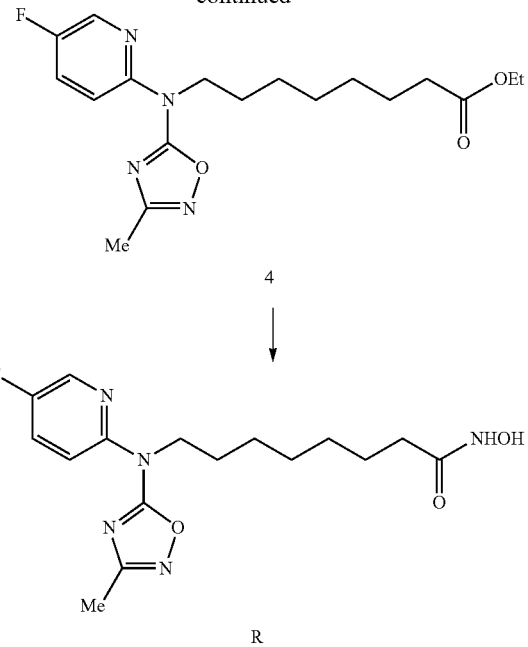

NaH (60%) (43 mg, 1.08 mmol) was added portion-wise to N-(5-fluoropyridin-2-yl)-3-methyl-1,2,4-oxadiazol-5-amine (3) (as per Example Q above) (200 mg, 1.03 mmol) in DMF (7 mL) at 5° C. under Ar(g). The reaction mixture was then stirred for 20 min, and ethyl-8-iodooctanoate (399 mg, 1.34 mmol) was added. The reaction mixture was stirred at 70° C. under Ar(g) for 1 h in the dark, then poured onto demineralized water (100 mL), and extracted with EtOAc (3×50 mL). The organic phases were combined, dried over Na₂SO₄, filtered and subsequently evaporated under vacuum. The resulting residue was purified by flash chromatography, eluting with EtOAc/Hexane (3:7) to furnish ethyl 8-((5-fluoropyridin-2-yl)(3-methyl-1,2,4-oxadiazol-5-yl)amino)octanoate (4) as a yellow solid (250 mg, 66%).

LCMS (ES): Found 365.1 [MH]+.

A fresh solution of NH₂OH in MeOH was prepared: [KOH (1.92 g, 34.3 mmol) in MeOH (15 mL) was added to NH₂OH.HCl (2.38 g, 34.3 mmol) in MeOH (15 mL) at 0° C.]. The mixture was stirred for 20 min at 0° C., then filtered to remove salts; the filtrate was then added to ethyl 8-((5-fluoropyridin-2-yl)(3-methyl-1,2,4-oxadiazol-5-yl)amino)octanoate (4) (250 mg, 0.68 mmol) followed by KOH (384 mg, 6.8 mmol) solubilized in MeOH (8 mL). The reaction mixture was stirred at it for 21 h, then concentrated in vacuo, poured onto brine/H₂O (30 mL/70 mL), and extracted with CH₂Cl₂ (3×50 mL). The organic phases were combined, dried over Na₂SO₄, filtered and subsequently evaporated under vacuum. The resulting residue was purified by flash chromatography, eluting with MeOH/CH₂Cl₂ (1:9) to provide 8-((5-fluoropyridin-2-yl)(3-methyl-1,2,4-oxadiazol-5-yl)amino)-N-hydroxyoctanamide, Example R, as a light brown solid (50 mg, 20%).

$^1$H NMR (400 MHz, DMSO-d₅) δ: 10.31 (br. s., 1H), 8.64 (br. s, 1H), 8.47 (d, J=3.0 Hz, 1H), 7.96 (dd, J=9.1, 3.9 Hz, 1H), 7.86 (ddd, J=9.1, 8.0, 3.1 Hz, 1H), 4.03-4.16 (m, 3H), 2.22 (s, 3H), 1.91 (t, J=7.4 Hz, 2H), 1.55-1.69 (m, 2H), 1.37-1.50 (m, 2H), 1.14-1.32 (m, 5H).

LCMS (ES): Found 352.7 [MH]+.

Example S 7-((5-Fluoropyridin-2-yl)(1-methyl-1H-benzo[d]imidazol-2-yl)amino)-N-hydroxyheptanamide

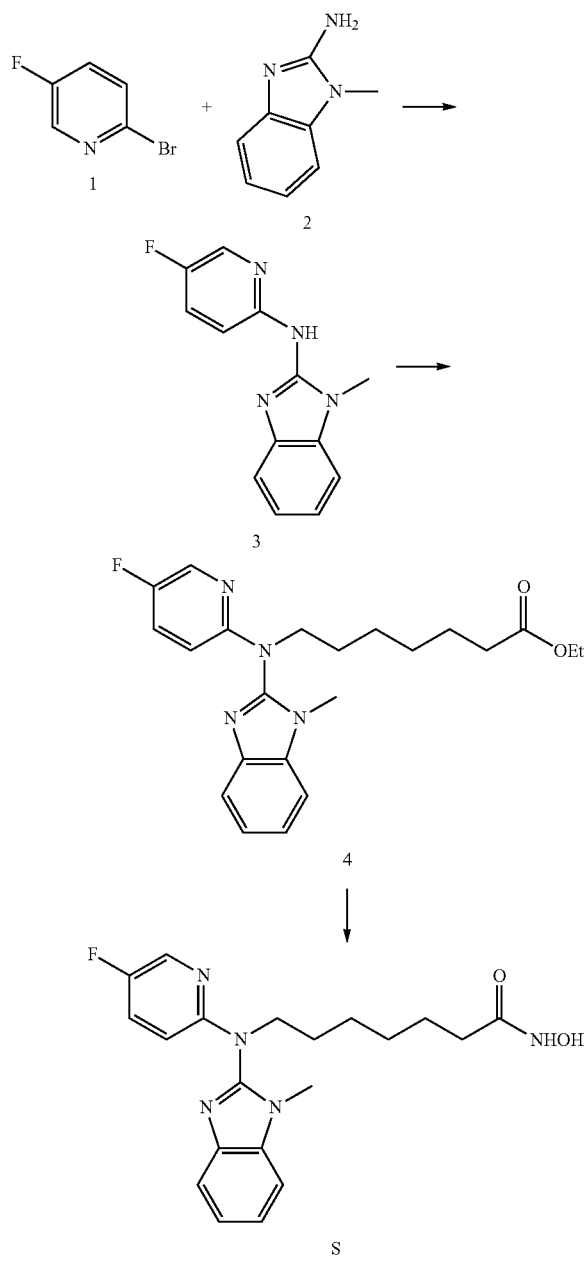

2-Bromo-5-fluoropyridine (1) (1.0 g, 5.71 mmol), 2-amino-1-methylbenzimidazole (2) (840 mg, 5.71 mmol), Xantphos (0.330 g, 0.57 mmol), and $Cs_2CO_3$ (2.79 g, 8.56 mmol) were combined in dry 1,4-dioxane (15 mL). The reaction mixture was degassed with $N_2(g)$ and placed under vacuum for 10 min. $Pd_2(dba)_3$ (0.26 g, 0.28 mmol) was then added and the resulting reaction mixture was heated at 90° C. for 30 h. It was then poured onto demineralized water (200 mL), and extracted with EtOAc (3×100 mL). The organic phases were combined, dried over $Na_2SO_4$, filtered and subsequently evaporated under vacuum. The resulting residue was purified by flash chromatography, eluting with EtOAc/Hexane (1:1) to provide N-(5-fluoropyridin-2-yl)-1-methyl-1H-benzo[d]imidazol-2-amine (3) as a yellow solid (0.56 g, 41%).

LCMS (ES): Found 243.1 $[MH]^+$

NaH (60%) (36 mg, 0.88 mmol) was added portion-wise to N-(5-fluoropyridin-2-yl)-1-methyl-1H-benzo[d]imidazol-2-amine (3) (205 mg, 0.84 mmol) in DMF (7 mL) at 5° C. under Ar(g). The reaction mixture was then stirred for 20 min, and ethyl-7-iodoheptanoate (312 mg, 1.1 mmol) was added. The reaction mixture was stirred at 70° C. under Ar(g) for 1 h in the dark, then poured onto demineralized water (100 mL), and extracted with EtOAc (3×50 mL). The organic phases were combined, dried over $Na_2SO_4$, filtered and subsequently evaporated under vacuum. The resulting residue was purified by flash chromatography, eluting with EtOAc/Hexane (3:7) to furnish ethyl 7-((5-fluoropyridin-2-yl)(1-methyl-1H-benzo[d]imidazol-2-yl)amino)heptanoate (4) as a yellow solid (124 mg, 36%).

LCMS (ES): Found 399.2 [MH]+.

A fresh solution of $NH_2OH$ in MeOH was prepared: [KOH (0.877 g, 15.5 mmol) in MeOH (15 mL) was added to $NH_2OH \cdot HCl$ (1.08 g, 15.5 mmol) in MeOH (15 mL) at 0° C.]. The mixture was stirred for 20 min at 0° C., then filtered to remove salts; the filtrate was then added to ethyl 7-((5-fluoropyridin-2-yl)(1-methyl-1H-benzo[d]imidazol-2-yl)amino)heptanoate (4) (124 mg, 0.31 mmol) followed by KOH (174 mg, 3.1 mmol) solubilized in MeOH (5 mL). The reaction mixture was stirred at it for 21 h, then concentrated in vacuo, poured onto brine/$H_2O$ (30 mL/70 mL), and extracted with $CH_2Cl_2$ (3×50 mL). The organic phases were combined, dried over $Na_2SO_4$, filtered and subsequently evaporated under vacuum. The resulting residue was purified by flash chromatography, eluting with MeOH/$CH_2Cl_2$ (1:9) to provide 7-((5-fluoropyridin-2-yl)(1-methyl-1H-benzo[d]imidazol-2-yl)amino)-N-hydroxyheptanamide (S) as a light brown solid (23 mg, 19%).

$^1$H NMR (400 MHz, DMSO-$d_5$) δ: 10.31 (br. s, 1H), 8.64 (s, 1H), 8.19 (d, J=3.1 Hz, 1H), 7.55-7.62 (m, 2H), 7.49 (d, J=7.2 Hz, 1H), 7.17-7.27 (m, 2H), 6.66 (dd, J=9.2, 3.4 Hz, 1H), 3.89-3.99 (m, 2H), 3.42 (s, 3H), 1.90 (t, J=7.4 Hz, 2H), 1.58-1.70 (m, 2H), 1.38-1.50 (m, 2H), 1.17-1.35 (m, 4H).

LCMS (ES): Found 386.2 [MH]+.

Example T 8-((5-Fluoropyridin-2-yl)(1-methyl-1H-benzo[d]imidazol-2-yl)amino)-N-hydroxyoctanamide

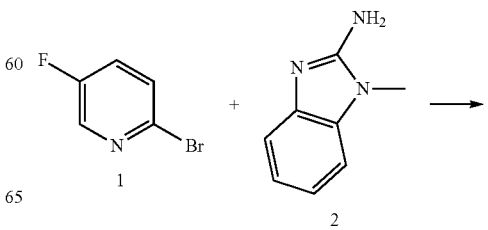

45

-continued

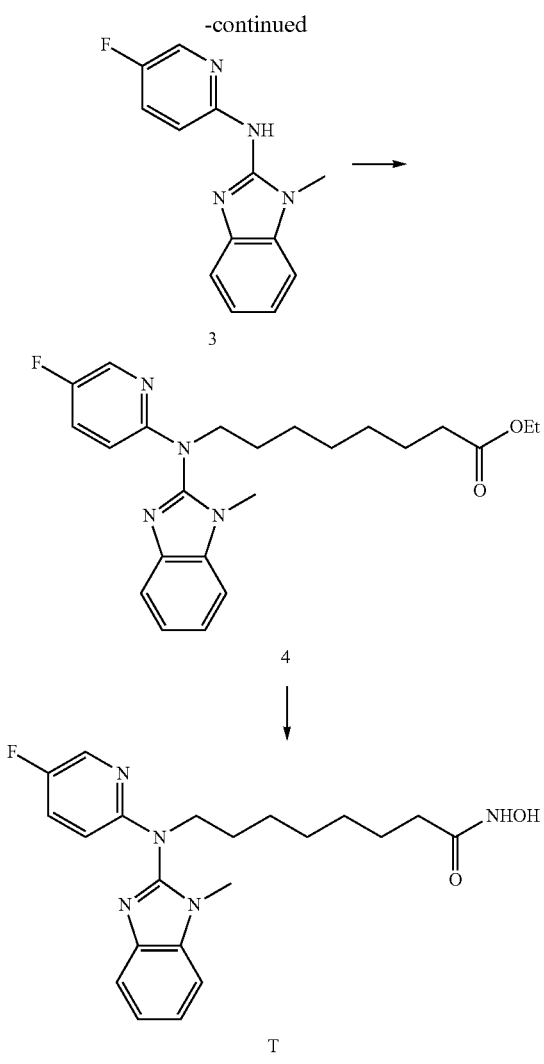

extracted with CH$_2$Cl$_2$ (3×50 mL). The organic phases were combined, dried over Na$_2$SO$_4$, filtered and subsequently evaporated under vacuum. The resulting residue was purified by flash chromatography, eluting with MeOH/CH$_2$Cl$_2$ (1:9) to provide 8-((5-fluoropyridin-2-yl)(1-methyl-1H-benzo[d]imidazol-2-yl)amino)-N-hydroxyoctanamide, Example T, as a light yellow solid (20 mg, 16%).

$^1$H NMR (400 MHz, DMSO-d$_5$) δ: 10.30 (s, 1H), 8.64 (s, 1H), 8.18 (d, J=3.1 Hz, 1H), 7.55-7.62 (m, 1H), 7.49 (d, J=7.4 Hz, 1H), 7.22 (dtd, J=17.6, 7.4, 1.3 Hz, 1H), 6.66 (dd, J=9.2, 3.4 Hz, 1H), 3.88-4.00 (m, 2H), 3.42 (s, 2H), 1.89 (t, J=7.3 Hz, 1H), 1.65 (br. s., 2H), 1.44 (dt, J=14.5, 7.4 Hz, 2H), 1.12-1.34 (m, 6H).

LCMS (ES): Found 400.2 [MH]+.

Example U 7-((5-Fluoropyridin-2-yl)(1-methyl-1H-pyrazol-3-yl)amino)-N-hydroxyheptanamide

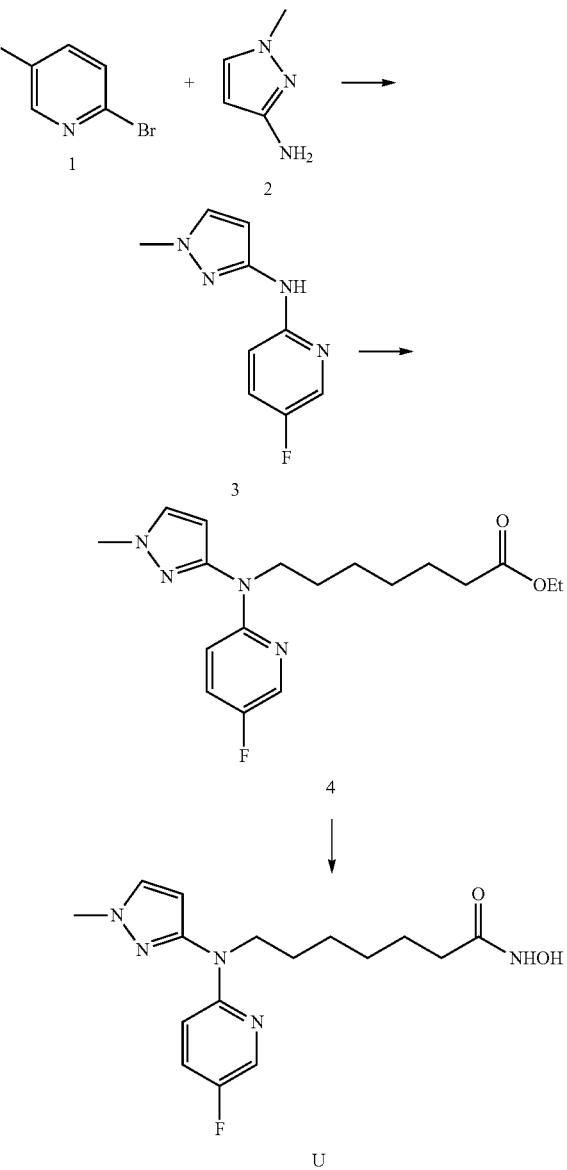

NaH (60%) (36 mg, 0.88 mmol) was added portion-wise to N-(5-fluoropyridin-2-yl)-1-methyl-1H-benzo[d]imidazol-2-amine (3) (as per Example S above) (205 mg, 0.84 mmol) in DMF (8 mL) at 5° C. under Ar(g). The reaction mixture was then stirred for 20 min, and ethyl-8-iodooctanoate (Intermediate B) (328 mg, 1.1 mmol) was added. The reaction mixture was stirred at 70° C. under Ar(g) for 1 h in the dark, then poured onto demineralized water (100 mL), and extracted with EtOAc (3×50 mL). The organic phases were combined, dried over Na$_2$SO$_4$, filtered and subsequently evaporated under vacuum. The resulting residue was purified by flash chromatography, eluting with EtOAc/Hexane (3:7) to furnish ethyl 8-((5-fluoropyridin-2-yl)(1-methyl-1H-benzo[d]imidazol-2-yl)amino)octanoate (4) as a yellow solid (130 mg, 37%).

LCMS (ES): Found 413.2 [MH]+.

A fresh solution of NH$_2$OH in MeOH was prepared: [KOH (0.88 g, 15.7 mmol) in MeOH (10 mL) was added to NH$_2$OH.HCl (1.09 g, 15.7 mmol) in MeOH (10 mL) at 0° C.]. The mixture was stirred for 20 min at 0° C., then filtered to remove salts; the filtrate was then added to ethyl 8-((5-fluoropyridin-2-yl)(1-methyl-1H-benzo[d]imidazol-2-yl)amino)octanoate (4) (130 mg, 0.31 mmol) followed by KOH (176 mg, 3.1 mmol) solubilized in MeOH (5 mL). The reaction mixture was stirred at it for 21 h, then concentrated in vacuo, poured onto brine/H$_2$O (30 mL/70 mL), and 2-Bromo-5-fluoropyridine (1) (1.0 g, 5.71 mmol), 1-methyl-1H-pyrazol-3-amine (2) (554 mg, 5.71 mmol), Xantphos (0.33 g, 0.57 mmol), and $Cs_2CO_3$ (2.79 g, 8.56 mmol) were combined in dry 1,4-dioxane (15 mL). The reaction mixture was degassed with $N_2(g)$ and placed under vacuum for 10 min. $Pd_2(dba)_3$ (0.26 g, 0.28 mmol) was then added and the resulting reaction mixture was heated at 90° C. for 30 h. It was then poured onto demineralized water (200 mL), and extracted with EtOAc (3×100 mL). The organic phases were combined, dried over $Na_2SO_4$, filtered and subsequently evaporated under vacuum. The resulting residue was purified by flash chromatography, eluting with EtOAc/Hexane (1:1) to provide 5-fluoro-N-(1-methyl-1H-pyrazol-3-yl)pyridin-2-amine (3) as a yellow solid (0.65 g, 61%).

LCMS (ES): Found 193.0 [MH]+.

NaH (60%) (44 mg, 11.2 mmol) was added portion-wise to 5-fluoro-N-(1-methyl-1H-pyrazol-3-yl)pyridin-2-amine (3) (205 mg, 1.06 mmol) in DMF (7 mL) at 5° C. under Ar(g). The reaction mixture was then stirred for 20 min, and ethyl-7-iodoheptanoate (391 mg, 1.3 mmol) was added. The reaction mixture was stirred at 70° C. under Ar(g) for 1 h in the dark, then poured onto demineralized water (100 mL), and extracted with EtOAc (3×50 mL). The organic phases were combined, dried over $Na_2SO_4$, filtered and subsequently evaporated under vacuum. The resulting residue was purified by flash chromatography, eluting with EtOAc/Hexane (3:7) to furnish ethyl 7-((5-fluoropyridin-2-yl)(1-methyl-1H-pyrazol-3-yl)amino)heptanoate (4) as a yellow solid (240 mg, 64%).

LCMS (ES): Found 349.2 [MH]+.

A fresh solution of $NH_2OH$ in MeOH was prepared: [KOH (2.0 g, 35.7 mmol) in MeOH (15 mL) was added to $NH_2OH.HCl$ (2.4 g, 35.7 mmol) in MeOH (15 mL) at 0° C.]. The mixture was stirred for 20 min at 0° C., then filtered to remove salts; the filtrate was then added to ethyl 7-((5-fluoropyridin-2-yl)(1-methyl-1H-pyrazol-3-yl)amino)heptanoate (4) (240 mg, 0.70 mmol) followed by KOH (400 mg, 7.0 mmol) solubilized in MeOH (5 mL). The reaction mixture was stirred at it for 21 h, then concentrated in vacuo, poured onto brine/$H_2O$ (30 mL/70 mL), and extracted with $CH_2Cl_2$ (3×50 mL). The organic phases were combined, dried over $Na_2SO_4$, filtered and subsequently evaporated under vacuum. The resulting residue was purified by flash chromatography, eluting with MeOH/$CH_2Cl_2$ (1:9) to provide 7-((5-fluoropyridin-2-yl)(1-methyl-1H-pyrazol-3-yl)amino)-N-hydroxyheptanamide, Example U, as an off-white solid (45 mg, 19%).

$^1$H NMR (400 MHz, DMSO-$d_5$) δ: 10.32 (s, 1H), 8.65 (s, 1H), 8.12 (d, J=3.1 Hz, 1H), 7.67 (d, J=2.1 Hz, 1H), 7.42 (ddd, J=9.2, 8.4, 3.1 Hz, 1H), 6.89 (dd, J=9.3, 3.6 Hz, 1H), 6.10 (d, J=2.3 Hz, 1H), 3.80-3.88 (m, 2H), 3.78 (s, 3H), 1.91 (t, J=7.4 Hz, 2H), 1.49-1.60 (m, 2H), 1.45 (quin, J=7.0 Hz, 2H), 1.17-1.31 (m, 4H).

LCMS (ES): Found 336.1 [MH]+.

Example V 8-((5-Fluoropyridin-2-yl)(1-methyl-1H-pyrazol-3-yl)amino)-N-hydroxyoctanamide

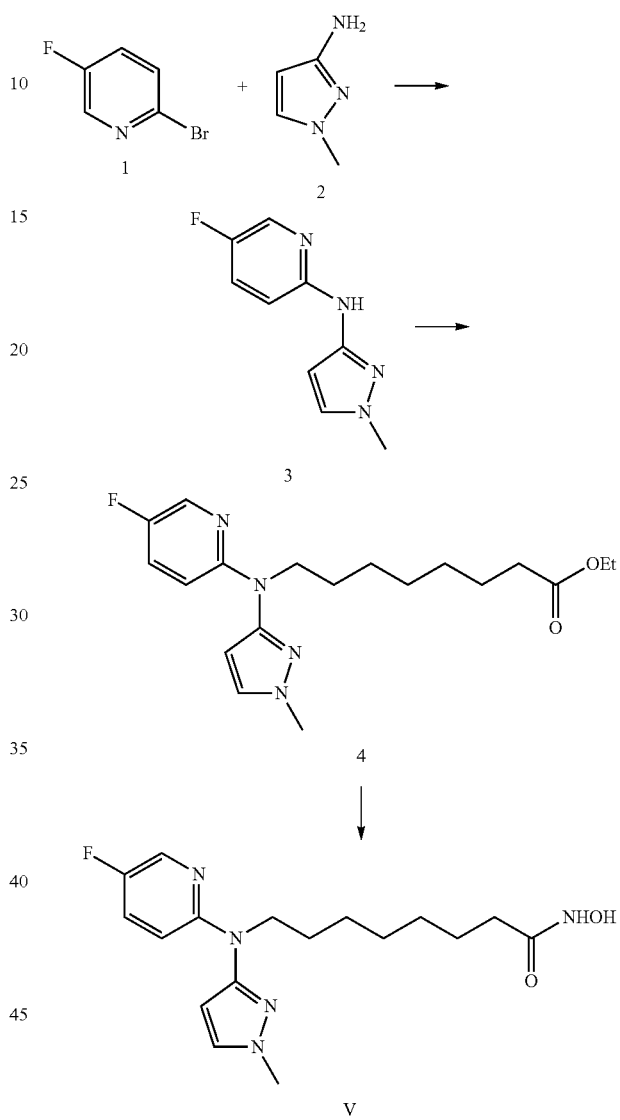

NaH (60%) (44 mg, 1.12 mmol) was added portion-wise to 5-fluoro-N-(1-methyl-1H-pyrazol-3-yl)pyridin-2-amine (3) (as per Example U above) (205 mg, 1.06 mmol) in DMF (7 mL) at 5° C. under Ar(g). The reaction mixture was then stirred for 20 min, and ethyl-8-iodooctanoate (399 mg, 1.34 mmol) was added. The reaction mixture was stirred at 70° C. under Ar(g) for 1 h in the dark, then poured onto demineralized water (100 mL), and extracted with EtOAc (3×50 mL). The organic phases were combined, dried over $Na_2SO_4$, filtered and subsequently evaporated under vacuum. The resulting residue was purified by flash chromatography, eluting with EtOAc/Hexane (3:7) to furnish ethyl 8-((5-fluoropyridin-2-yl)(1-methyl-1H-pyrazol-3-yl)amino)octanoate (4) as a yellow solid (265 mg, 68%).

LCMS (ES): Found 363.4 [MH]+.

A fresh solution of $NH_2OH$ in MeOH was prepared: [KOH (2.05 g, 36.6 mmol) in MeOH (15 mL) was added to NH$_2$OH.HCl (2.54 g, 36.6 mmol) in MeOH (15 mL) at 0° C.]. The mixture was stirred for 20 min at 0° C., then filtered to remove salts; the filtrate was then added to ethyl 8-((5-fluoropyridin-2-yl)(1-methyl-1H-pyrazol-3-yl)amino)octanoate (4) (265 mg, 0.73 mmol) followed by KOH (410 mg, 7.3 mmol) solubilized in MeOH (8 mL). The reaction mixture was stirred at it for 21 h, then concentrated in vacuo, poured onto brine/H$_2$O (30 mL/70 mL), and extracted with CH$_2$Cl$_2$ (3×50 mL). The organic phases were combined, dried over Na$_2$SO$_4$, filtered and subsequently evaporated under vacuum. The resulting residue was purified by flash chromatography, eluting with MeOH/CH$_2$Cl$_2$ (1:9) to provide 8-((5-fluoropyridin-2-yl)(1-methyl-1H-pyrazol-3-yl)amino)-N-hydroxyoctanamide, Example V, as a light brown solid (75 mg, 29%).

$^1$H NMR (400 MHz, DMSO-d$_5$) δ: 10.31 (s, 1H), 8.65 (s, 1H), 8.12 (d, J=3.1 Hz, 1H), 7.67 (d, J=2.1 Hz, 1H), 7.42 (ddd, J=9.3, 8.3, 3.1 Hz, 1H), 6.89 (dd, J=9.4, 3.6 Hz, 1H), 6.10 (d, J=2.3 Hz, 1H), 5.76 (s, 1H), 3.80-3.89 (m, 2H), 3.78 (s, 3H), 1.91 (t, J=7.4 Hz, 2H), 1.55 (br. s., 2H), 1.45 (quin, J=7.1 Hz, 2H), 1.12-1.30 (m, 6H).

LCMS (ES): Found 350.1 [MH]+.

Example W 7-(Benzo[d]oxazol-2-yl(5-fluoropyridin-2-yl)amino)-N-hydroxyheptanamide

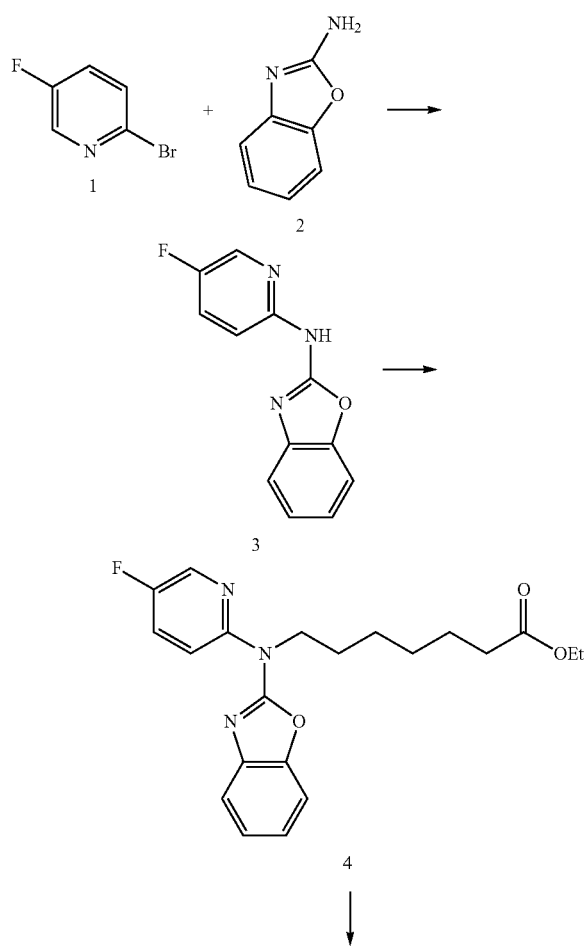

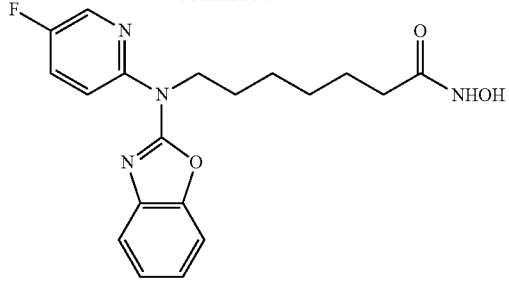

2-Bromo-5-fluoropyridine (1) (1.0 g, 5.71 mmol), benzo[d]oxazol-2-amine (2) (766 mg, 5.71 mmol), Xantphos (0.330 g, 0.57 mmol), and Cs$_2$CO$_3$ (2.79 g, 8.56 mmol) were combined in dry 1,4-dioxane (15 mL). The reaction mixture was degassed with N$_2$(g) and placed under vacuum for 10 min. Pd$_2$(dba)$_3$ (0.261 g, 0.28 mmol) was then added and the resulting reaction mixture was heated at 90° C. for 30 h. It was then poured onto demineralized water (200 mL), and extracted with EtOAc (3×100 mL). The organic phases were combined, dried over Na$_2$SO$_4$, filtered and subsequently evaporated under vacuum. The resulting residue was purified by flash chromatography, eluting with EtOAc/Hexane (1:1) to provide N-(5-fluoropyridin-2-yl)benzo[d]oxazol-2-amine (3) as a yellow solid (0.6 g, 46%).

LCMS (ES): Found 230.1 [MH]+.

NaH (60%) (36 mg, 0.91 mmol) was added portion-wise to N-(5-fluoropyridin-2-yl)benzo[d]oxazol-2-amine (3) (200 mg, 0.87 mmol) in DMF (7 mL) at 5° C. under Ar(g). The reaction mixture was then stirred for 20 min, and ethyl-7-iodoheptanoate (322 mg, 1.13 mmol) was added. The reaction mixture was stirred at 70° C. under Ar(g) for 1 h in the dark, then poured onto demineralized water (100 mL), and extracted with EtOAc (3×50 mL). The organic phases were combined, dried over Na$_2$SO$_4$, filtered and subsequently evaporated under vacuum. The resulting residue was purified by flash chromatography, eluting with EtOAc/Hexane (3:7) to furnish ethyl 7-(benzo[d]oxazol-2-yl(5-fluoropyridin-2-yl)amino)heptanoate (4) as a yellow solid (196 mg, 57%).

LCMS (ES): Found 386.1 [MH]+.

A fresh solution of NH$_2$OH in MeOH was prepared: [KOH (1.43 g, 25.5 mmol) in MeOH (15 mL) was added to NH$_2$OH.HCl (1.78 g, 25.5 mmol) in MeOH (15 mL) at 0° C.]. The mixture was stirred for 20 min at 0° C., then filtered to remove salts; the filtrate was then added to ethyl 7-(benzo[d]oxazol-2-yl(5-fluoropyridin-2-yl)amino)heptanoate (4) (196 mg, 0.51 mmol) followed by KOH (287 mg, 5.1 mmol) solubilized in MeOH (5 mL). The reaction mixture was stirred at it for 21 h, then concentrated in vacuo, poured onto brine/H$_2$O (30 mL/70 mL), and extracted with CH$_2$Cl$_2$ (3×50 mL). The organic phases were combined, dried over Na$_2$SO$_4$, filtered and subsequently evaporated under vacuum. The resulting residue was purified by flash chromatography, eluting with MeOH/CH$_2$Cl$_2$ (1:9) to provide 7-(benzo[d]oxazol-2-yl(5-fluoropyridin-2-yl)amino)-N-hydroxyheptanamide, Example W, as an orange solid (70 mg, 37%).

$^1$H NMR (400 MHz, DMSO-d$_5$) δ: 10.33 (s, 1H), 8.67 (s, 1H), 8.47 (d, J=3.1 Hz, 1H), 8.09 (dd, J=9.2, 3.9 Hz, 1H), 7.86 (ddd, J=9.1, 8.2, 3.1 Hz, 1H), 7.46-7.56 (m, 2H), 7.25 (td, J=7.7, 1.1 Hz, 1H), 7.13-7.18 (m, 1H), 4.21 (t, J=7.4 Hz, 2H), 1.91 (t, J=7.3 Hz, 2H), 1.63-1.76 (m, 2H), 1.46 (dt, J=14.1, 7.2 Hz, 2H), 1.23-1.37 (m, 4H).

LCMS (ES): Found 373.1 [MH]+.

Example X 8-(Benzo[d]oxazol-2-yl(5-fluoropyridin-2-yl)amino)-N-hydroxyoctanamide

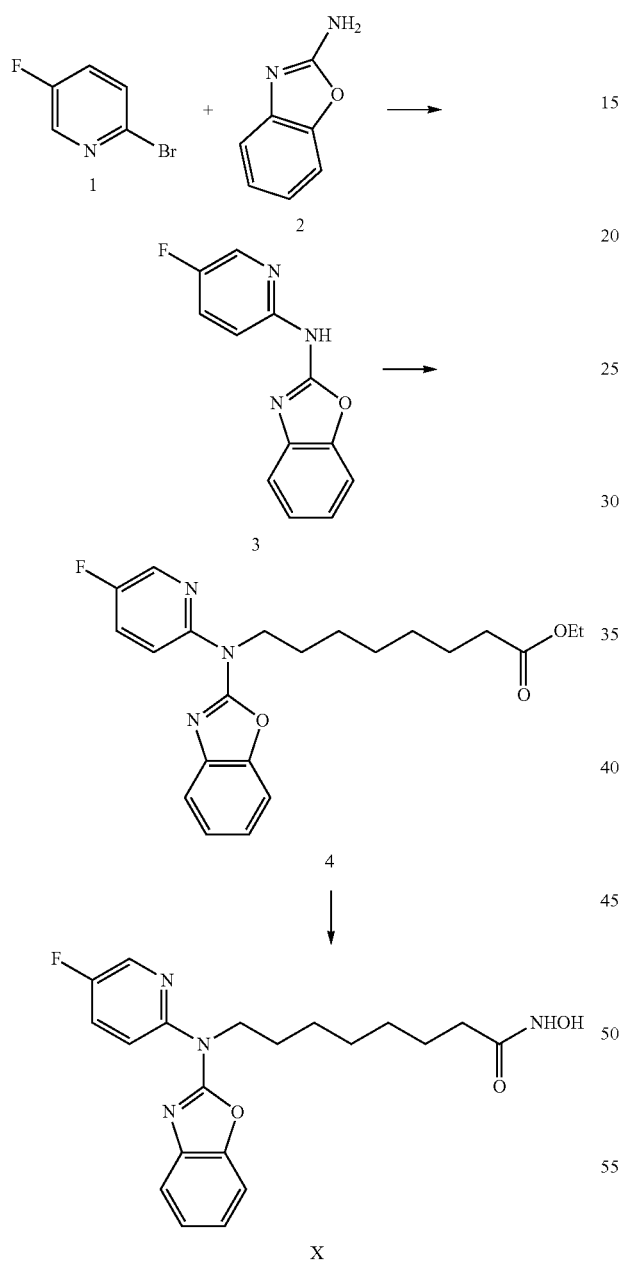

NaH (60%) (92 mg, 2.29 mmol) was added portion-wise to N-(5-fluoropyridin-2-yl)benzo[d]oxazol-2-amine (3) (as per Example W above) (500 mg, 1.06 mmol) in DMF (10 mL) at 5° C. under Ar(g). The reaction mixture was then stirred for 20 min, and ethyl-8-iodooctanoate (845 mg, 2.8 mmol) was added. The reaction mixture was stirred at 70° C. under Ar(g) for 1 h in the dark, then poured onto demineralized water (100 mL), and extracted with EtOAc (3×50 mL). The organic phases were combined, dried over Na₂SO₄, filtered and subsequently evaporated under vacuum. The resulting residue was purified by flash chromatography, eluting with EtOAc/Hexane (3:7) to furnish ethyl 8-(benzo[d]oxazol-2-yl(5-fluoropyridin-2-yl)amino)octanoate (4) as a yellow solid (510 mg, 58%).

LCMS (ES): Found 400.2 [MH]⁺

A fresh solution of NH₂OH in MeOH was prepared: [KOH (3.58 g, 63.9 mmol) in MeOH (20 mL) was added to NH₂OH.HCl (4.44 g, 63.9 mmol) in MeOH (20 mL) at 0° C.]. The mixture was stirred for 20 min at 0° C., then filtered to remove salts; the filtrate was then added to ethyl 8-(benzo[d]oxazol-2-yl(5-fluoropyridin-2-yl)amino)octanoate (4) (510 mg, 1.27 mmol) followed by KOH (712 mg, 12.7 mmol) solubilized in MeOH (10 mL). The reaction mixture was stirred at it for 21 h, then concentrated in vacuo, poured onto brine/H₂O (30 mL/70 mL), and extracted with CH₂Cl₂ (3×50 mL). The organic phases were combined, dried over Na₂SO₄, filtered and subsequently evaporated under vacuum. The resulting residue was purified by flash chromatography, eluting with MeOH/CH₂Cl₂ (1:9) to provide 8-(benzo[d]oxazol-2-yl(5-fluoropyridin-2-yl)amino)-N-hydroxyoctanamide (X) as a light yellow solid (45 mg, 9%).

¹H NMR (400 MHz, DMSO-d₆) δ: 10.32 (br. s., 1H), 8.65 (br. s., 1H), 8.47 (d, J=3.1 Hz, 1H), 8.08 (dd, J=9.1, 3.9 Hz, 1H), 7.85 (ddd, J=9.1, 8.2, 3.1 Hz, 1H), 7.50 (dd, J=19.7, 7.4 Hz, 2H), 7.25 (td, J=7.6, 1.1 Hz, 1H), 7.12-7.18 (m, 1H), 4.18-4.25 (m, 2H), 1.91 (t, J=7.4 Hz, 2H), 1.64-1.75 (m, 2H), 1.45 (dt, J=14.7, 7.5 Hz, 2H), 1.15-1.37 (m, 6H).

LCMS (ES): Found 387.1 [MH]+.

Example Y 7-((4-(4-Fluorophenyl)pyridin-2-yl)(1-methyl-1H-pyrazol-3-yl)amino)-N-hydroxyheptanamide

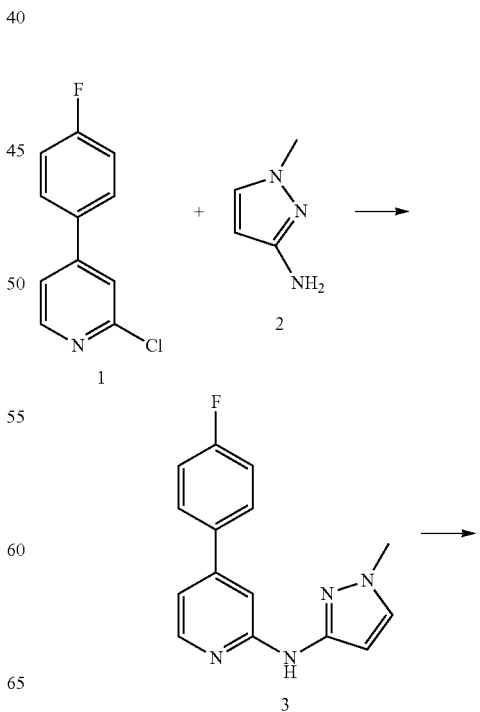

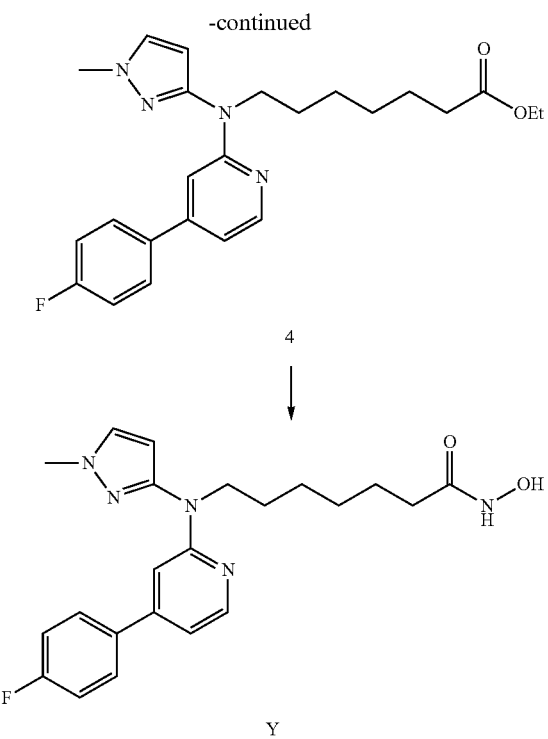

amino)heptanoate (4) (296 mg, 0.69 mmol) followed by KOH (391 mg, 6.9 mmol) solubilized in MeOH (8 mL). The reaction mixture was stirred at it for 21 h, then concentrated in vacuo, poured onto brine/$H_2O$ (30 mL/70 mL), and extracted with $CH_2Cl_2$ (3×50 mL). The organic phases were combined, dried over $Na_2SO_4$, filtered and subsequently evaporated under vacuum. The resulting residue was purified by flash chromatography, eluting with MeOH/$CH_2Cl_2$ (1:9) to provide 7-((4-(4-fluorophenyl)pyridin-2-yl)(1-methyl-1H-pyrazol-3-yl)amino)-N-hydroxyheptanamide, Example Y, as light yellow solid (31 mg, 10%).

$^1$H NMR (400 MHz, DMSO-$d_5$) δ: 10.33 (br. s., 1H), 8.66 (br. s., 1H), 8.21 (d, J=5.0 Hz, 1H), 7.69 (s, 1H), 7.56-7.65 (m, 2H), 7.29 (t, J=8.8 Hz, 2H), 6.99 (s, 1H), 6.94 (d, J=5.0 Hz, 1H), 6.20 (s, 1H), 3.92 (t, J=7.3 Hz, 2H), 3.80 (s, 3H), 1.92 (t, J=7.4 Hz, 2H), 1.52-1.66 (m, 2H), 1.39-1.51 (m, 2H), 1.18-1.34 (m, 4H).

LCMS (ES): Found 412.2 [MH]+.

Example Z 8-((4-(4-Fluorophenyl)pyridin-2-yl)(1-methyl-1H-pyrazol-3-yl)amino)-N-hydroxyoctanamide 2-Chloro-4-(4-fluorophenyl)pyridine (1) (1.0 g, 4.8 mmol), 1-methyl-1H-pyrazol-3-amine (2) (469 mg, 4.8 mmol), Xantphos (0.28 g, 0.48 mmol), and $Cs_2CO_3$ (2.35 g, 7.24 mmol) were combined in dry 1,4-dioxane (15 mL). The reaction mixture was degassed with $N_2$(g) and placed under vacuum for 10 min. $Pd_2(dba)_3$ (0.22 g, 0.24 mmol) was then added and the resulting reaction mixture was heated at 90° C. for 30 h. It was then poured onto demineralized water (200 mL), and extracted with EtOAc (3×100 mL). The organic phases were combined, dried over $Na_2SO_4$, filtered and subsequently evaporated under vacuum. The resulting residue was purified by flash chromatography, eluting with EtOAc/Hexane (1:1) to provide 4-(4-fluorophenyl)-N-(1-methyl-1H-pyrazol-3-yl)pyridin-2-amine (3) as a yellow solid (1.0 g, 71%).

LCMS (ES): Found 269.1 [MH]+.

NaH (60%) (37 mg, 0.93 mmol) was added portion-wise to 4-(4-fluorophenyl)-N-(1-methyl-1H-pyrazol-3-yl)pyridin-2-amine (3) (250 mg, 0.93 mmol) in DMF (10 mL) at 5° C. under Ar(g). The reaction mixture was then stirred for 20 min, and ethyl-7-iodoheptanoate (344 mg, 1.21 mmol) was added. The reaction mixture was stirred at 70° C. under Ar(g) for 1 h in the dark, then poured onto demineralized water (100 mL), extracted with EtOAc (3×50 mL). The organic phases were combined, dried over $Na_2SO_4$, filtered and subsequently evaporated under vacuum. The resulting residue was purified by flash chromatography, eluting with EtOAc/Hexane (3:7) to furnish ethyl 7-((4-(4-fluorophenyl)pyridin-2-yl)(1-methyl-1H-pyrazol-3-yl)amino)heptanoate (4) as a yellow solid (296 mg, 63%).

LCMS (ES): Found 425.4 [MH]+.

A fresh solution of $NH_2OH$ in MeOH was prepared: [KOH (1.95 g, 34.8 mmol) in MeOH (15 mL) was added to $NH_2OH·HCl$ (2.42 g, 34.8 mmol) in MeOH (15 mL) at 0° C.]. The mixture was stirred for 20 min at 0° C., then filtered to remove salts; the filtrate was then added to ethyl 7-((4-(4-fluorophenyl)pyridin-2-yl)(1-methyl-1H-pyrazol-3-yl)

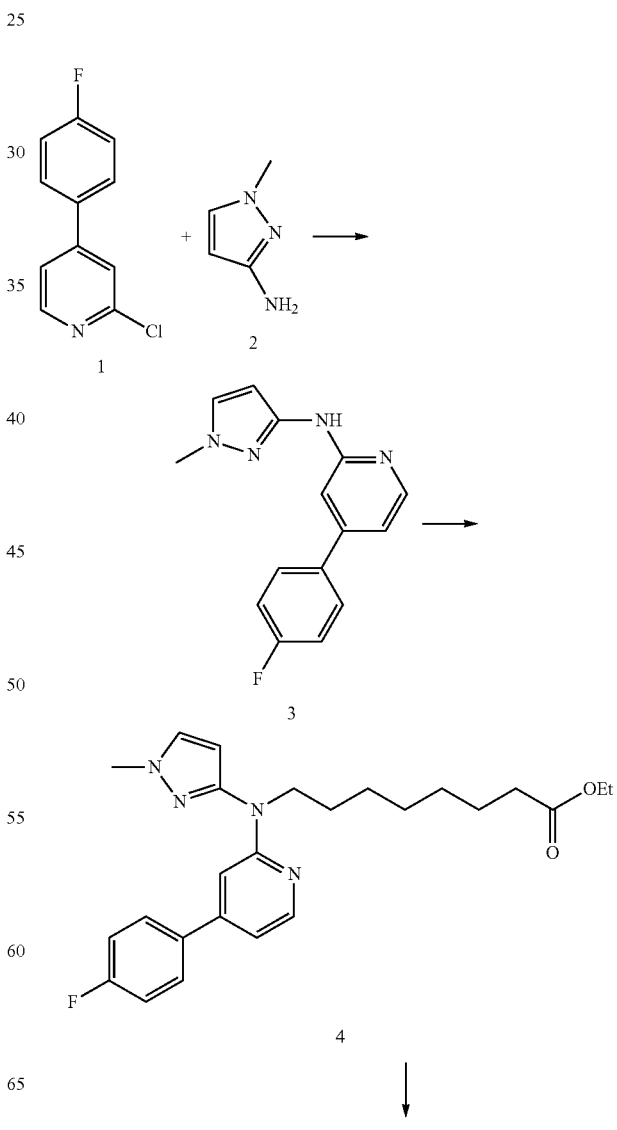

55
-continued

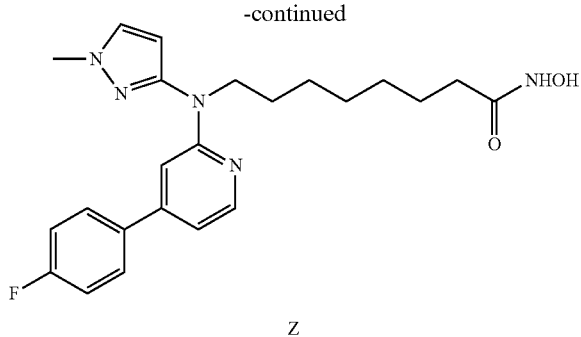

Z

NaH (60%) (37 mg, 0.93 mmol) was added portion-wise to 4-(4-fluorophenyl)-N-(1-methyl-1H-pyrazol-3-yl)pyridin-2-amine (3) (as per Example Y above) (250 mg, 1.05 mmol) in DMF (8 mL) at 5° C. under Ar(g). The reaction mixture was then stirred for 20 min, and ethyl-8-iodooctanoate (360 mg, 1.21 mmol) was added. The reaction mixture was stirred at 70° C. under Ar(g) for 1 h in the dark, then poured onto demineralized water (100 mL), and extracted with EtOAc (3×50 mL). The organic phases were combined, dried over $Na_2SO_4$, filtered and subsequently evaporated under vacuum. The resulting residue was purified by flash chromatography, eluting with EtOAc/Hexane (3:7) to furnish ethyl 8-((4-(4-fluorophenyl)pyridin-2-yl)(1-methyl-1H-pyrazol-3-yl)amino)octanoate (4) as a light yellow solid (288 mg, 70%).

LCMS (ES): Found 439.3 [MH]+.

A fresh solution of $NH_2OH$ in MeOH was prepared: [KOH (1.84 g, 32.8 mmol) in MeOH (15 mL) was added to $NH_2OH \cdot HCl$ (2.28 g, 32.8 mmol) in MeOH (15 mL) at 0° C.]. The mixture was stirred for 20 min at 0° C., then filtered to remove salts; the filtrate was then added to ethyl 8-((4-(4-fluorophenyl)pyridin-2-yl)(1-methyl-1H-pyrazol-3-yl)amino)octanoate (4) (288 mg, 0.65 mmol) followed by KOH (368 mg, 6.5 mmol) solubilized in MeOH (10 mL). The reaction mixture was stirred at it for 21 h, then concentrated in vacuo, poured onto brine/$H_2O$ (30 mL/70 mL), and extracted with $CH_2Cl_2$ (3×50 mL). The organic phases were combined, dried over $Na_2SO_4$, filtered and subsequently evaporated under vacuum. The resulting residue was purified by flash chromatography, eluting with MeOH/$CH_2Cl_2$ (1:9) to provide 8-((4-(4-fluorophenyl)pyridin-2-yl)(1-methyl-1H-pyrazol-3-yl)amino)-N-hydroxyoctanamide, Example Z, as a light brown solid (100 mg, 35%).

$^1$H NMR (400 MHz, DMSO-$d_5$) δ: 10.33 (br. s, 1H), 8.66 (br. s., 1H), 8.21 (d, J=5.3 Hz, 1H), 7.69 (d, J=2.2 Hz, 1H), 7.58-7.64 (m, 2H), 7.26-7.33 (m, 2H), 6.98-7.01 (m, 1H), 6.94 (dd, J=5.3, 1.5 Hz, 1H), 6.21 (d, J=2.3 Hz, 1H), 3.87-3.98 (m, 2H), 3.80 (s, 3H), 1.91 (t, J=7.4 Hz, 2H), 1.53-1.65 (m, 2H), 1.45 (quin, J=7.2 Hz, 2H), 1.14-1.33 (m, 6H).

LCMS (ES): Found 426.2 [MH]+.

56
Example AA 7-((5-Fluoropyridin-2-yl)(3-(trifluoromethyl)1,2,4-thiadiazol-5-yl)amino)-N-hydroxyheptanamide

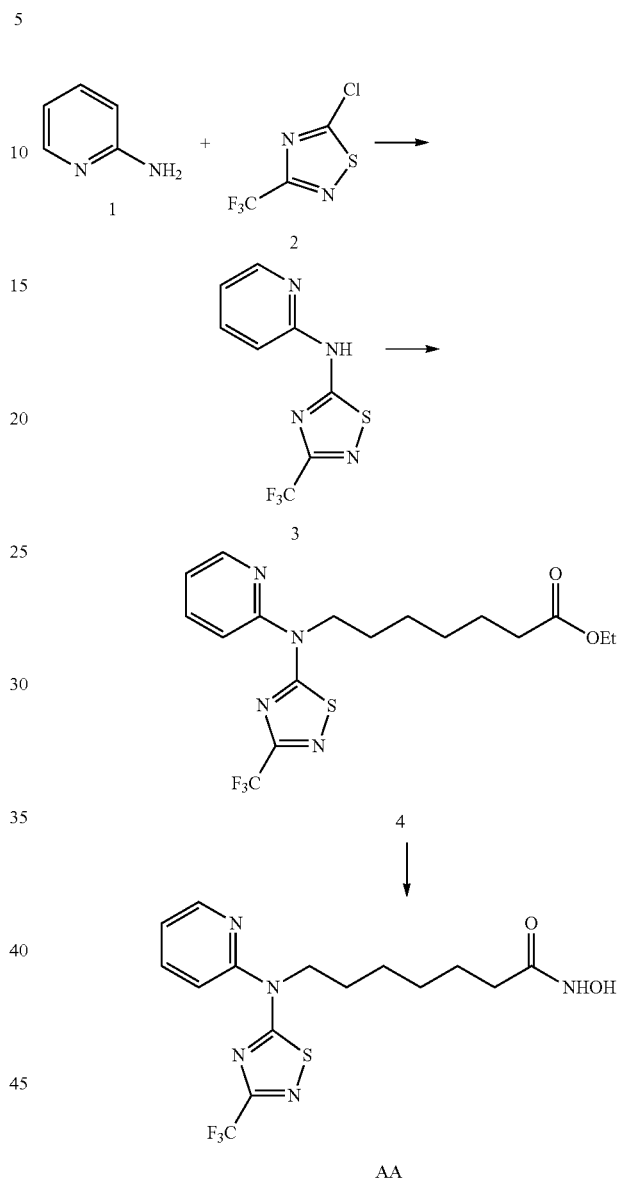

AA

Pyridin-2-amine (1) (1.0 g, 10.6 mmol), 5-chloro-3-(trifluoromethyl)1,2,4-thiadiazole (2) (1.82 g, 10.6 mmol), Xantphos (0.62 g, 1.06 mmol), and $Cs_2CO_3$ (5.18 g, 15.9 mmol) were combined in dry 1,4-dioxane (15 mL). The reaction mixture was degassed with $N_2$(g) and placed under vacuum for 10 min. $Pd_2(dba)_3$ (0.47 g, 0.53 mmol) was then added and the resulting reaction mixture was heated at 90° C. for 30 h. It was then poured onto demineralized water (200 mL), and extracted with EtOAc (3×100 mL). The organic phases were combined, dried over $Na_2SO_4$, filtered and subsequently evaporated under vacuum. The resulting residue was purified by flash chromatography, eluting with EtOAc/Hexane (1:1) to provide N-(pyridin-2-yl)-3-(trifluoromethyl)1,2,4-thiadiazol-5-amine (3) as a yellow solid (1.4 g, 57%).

LCMS (ES): Found 247.2 [MH]+.

NaH (60%) (49 mg, 1.21 mmol) was added portion-wise to N-(pyridin-2-yl)-3-(trifluoromethyl)1,2,4-thiadiazol-5- amine (3) (300 mg, 1.21 mmol) in DMF (7 mL) at 5° C. under Ar(g). The reaction mixture was then stirred for 20 min, and ethyl-7-iodoheptanoate (450 mg, 1.58 mmol) was added. The reaction mixture was stirred at 70° C. under Ar(g) for 1 h in the dark, then poured onto demineralized water (100 mL), and extracted with EtOAc (3×50 mL). The organic phases were combined, dried over Na₂SO₄, filtered and subsequently evaporated under vacuum. The resulting residue was purified by flash chromatography, eluting with EtOAc/Hexane (3:7), to furnish ethyl 7-(pyridin-2-yl(3-(trifluoromethyl)1,2,4-thiadiazol-5-yl)amino)heptanoate (4) as a yellow solid (440 mg, 89%).

LCMS (ES): Found 403.4 [MH]+.

A fresh solution of NH₂OH in MeOH was prepared: [KOH (3.69 g, 54.7 mmol) in MeOH (20 mL) was added to NH₂OH.HCl (3.80 g, 37.4 mmol) in MeOH (20 mL) at 0° C.]. The mixture was stirred for 20 min at 0° C., then filtered to remove salts; the filtrate was then added to ethyl 7-(pyridin-2-yl(3-(trifluoromethyl)1,2,4-thiadiazol-5-yl)amino)heptanoate (4) (440 mg, 1.1 mmol) followed by KOH (610 mg, 10.9 mmol) solubilized in MeOH (8 mL). The reaction mixture was stirred at rt for 21 h, then concentrated in vacuo, poured onto brine/H₂O (30 mL/70 mL), and extracted with CH₂Cl₂ (3×50 mL). The organic phases were combined, dried over Na₂SO₄, filtered and subsequently evaporated under vacuum. The resulting residue was purified by flash chromatography, eluting with MeOH/CH₂Cl₂ (1:9) to provide 7-((5-fluoropyridin-2-yl)(3-(trifluoromethyl)1,2,4-thiadiazol-5-yl)amino)-N-hydroxyheptanamide, Example AA, as an off-white solid (50 mg, 11%).

¹H NMR (400 MHz, DMSO-d₅) δ: 10.33 (br. s., 1H), 8.49-8.77 (m, 2H), 7.96-8.14 (m, 1H), 7.63 (d, J=8.6 Hz, 1H), 7.28 (dd, J=7.1, 5.1 Hz, 1H), 4.44 (t, J=7.3 Hz, 2H), 1.92 (t, J=7.3 Hz, 2H), 1.63-1.80 (m, 2H), 1.47 (dt, J=14.2, 7.2 Hz, 2H), 1.25-1.41 (m, 4H).

LCMS (ES): Found 389.94 [MH]+.

Example BB 8-((5-Fluoropyridin-2-yl)(3-(trifluoromethyl)1,2,4-thiadiazol-5-yl)amino)-N-hydroxyoctanamide

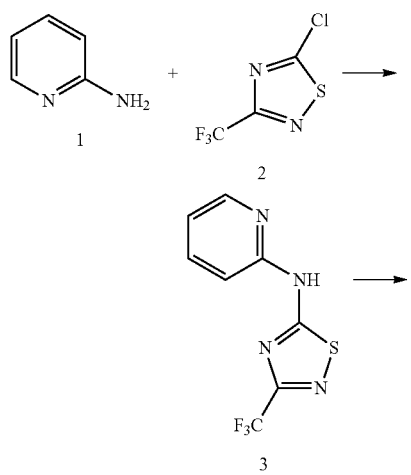

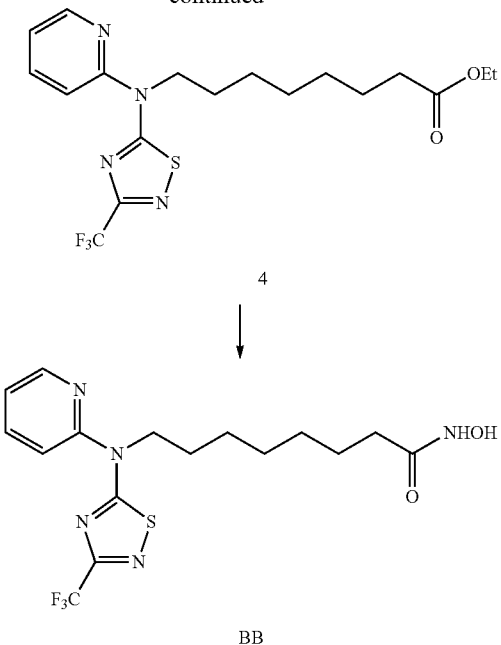

NaH (60%) (49 mg, 1.21 mmol) was added portion-wise to N-(pyridin-2-yl)-3-(trifluoromethyl)1,2,4-thiadiazol-5-amine (3) (as per Example AA above) (300 mg, 1.21 mmol) in DMF (8 mL) at 5° C. under Ar(g). The reaction mixture was then stirred for 20 min, and ethyl-8-iodooctanoate (473 mg, 1.58 mmol) was added. The reaction mixture was stirred at 70° C. under Ar(g) for 1 h in the dark, then poured onto demineralized water (100 mL), and extracted with EtOAc (3×50 mL). The organic phases were combined, dried over Na₂SO₄, filtered and subsequently evaporated under vacuum. The resulting residue was purified by flash chromatography, eluting with EtOAc/Hexane (3:7) to furnish ethyl 8-(pyridin-2-yl(3-(trifluoromethyl)1,2,4-thiadiazol-5-yl)amino)octanoate (4) as a yellow solid (440 mg, 86%).

LCMS (ES): Found 417.4 [MH]+.

A fresh solution of NH₂OH in MeOH was prepared: [KOH (2.96 g, 52.8 mmol) in MeOH (20 mL) was added to NH₂OH.HCl (3.67 g, 52.8 mmol) in MeOH (20 mL) at 0° C.]. The mixture was stirred for 20 min at 0° C., then filtered to remove salts; the filtrate was then added to ethyl 8-(pyridin-2-yl(3-(trifluoromethyl)1,2,4-thiadiazol-5-yl)amino)octanoate (4) (580 mg, 1.3 mmol) followed by KOH (589 mg, 10.5 mmol) solubilized in MeOH (10 mL). The reaction mixture was stirred at rt for 21 h, then concentrated in vacuo, poured onto brine/H₂O (30 mL/70 mL), and extracted with CH₂Cl₂ (3×50 mL). The organic phases were combined, dried over Na₂SO₄, filtered and subsequently evaporated under vacuum. The resulting residue was purified by flash chromatography, eluting with MeOH/CH₂Cl₂ (1:9) to provide 8-((5-fluoropyridin-2-yl)(3-(trifluoromethyl)1,2,4-thiadiazol-5-yl)amino)-N-hydroxyoctanamide, Example BB, as an off-white solid (60 mg, 14%).

¹H NMR (400 MHz, DMSO-d₅) δ: 10.34 (br. s., 1H), 8.67 (br. s., 1H), 8.61 (d, J=4.1 Hz, 1H), 8.01-8.10 (m, 1H), 7.63 (d, J=8.5 Hz, 1H), 7.28 (dd, J=7.1, 5.1 Hz, 1H), 4.44 (t, J=7.4 Hz, 2H), 1.91 (t, J=7.4 Hz, 2H), 1.72 (dt, J=13.4, 6.8 Hz, 2H), 1.46 (quin, J=7.3 Hz, 2H), 1.27-1.40 (m, 2H), 1.16-1.26 (m, 2H).

LCMS (ES): Found 404.4 [MH]+.

Example CC 7-((5-Fluoropyridin-2-yl)(3-methyl-1,2,4-thiadiazol-5-yl)amino)-N-hydroxyheptanamide

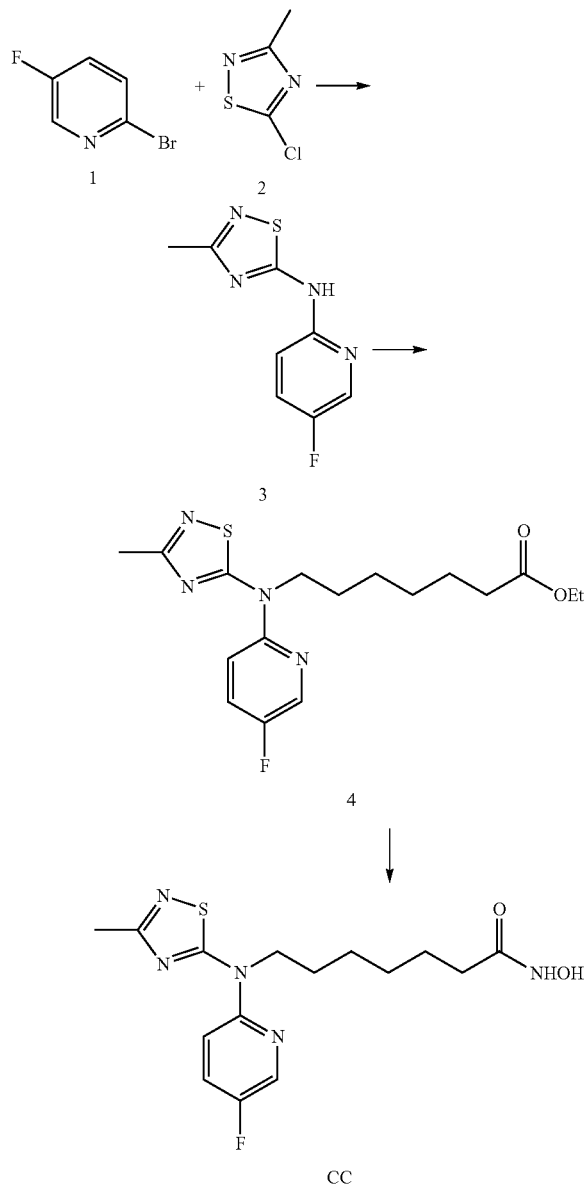

5-Fluoropyridin-2-amine (1) (1.0 g, 8.9 mmol), 5-chloro-3-methyl-1,2,4-thiadiazole (2) (1.19 g, 8.9 mmol), Xantphos (0.516 g, 0.89 mmol), and Cs₂CO₃ (4.35 g, 13.3 mmol) were combined in dry 1,4-dioxane (15 mL). The reaction mixture was degassed with N₂(g) and placed under vacuum for 10 min. Pd₂(dba)₃ (0.41 g, 0.44 mmol) was then added and the resulting reaction mixture was heated at 90° C. for 30 h. It was then poured onto demineralized water (200 mL), and extracted with EtOAc (3×100 mL). The organic phases were combined, dried over Na₂SO₄, filtered and subsequently evaporated under vacuum. The resulting residue was purified by flash chromatography, eluting with EtOAc/Hexane (3:7) to provide N-(5-fluoropyridin-2-yl)-3-methyl-1,2,4-thiadiazol-5-amine (3) as a yellow solid (1.2 g, 67%).

LCMS (ES): Found 211.1 [MH]+.

NaH (60%) (59 mg, 1.49 mmol) was added portion-wise to N-(5-fluoropyridin-2-yl)-3-methyl-1,2,4-thiadiazol-5-amine (3) (300 mg, 1.42 mmol) in DMF (7 mL) at 5° C. under Ar(g). The reaction mixture was then stirred for 20 min, and ethyl-7-iodoheptanoate (527 mg, 1.80 mmol) was added. The reaction mixture was stirred at 70° C. under Ar(g) for 1 h in the dark, then poured onto demineralized water (100 mL), extracted with EtOAc (3×50 mL). The organic phases were combined, dried over Na₂SO₄, filtered and subsequently evaporated under vacuum. The resulting residue was purified by flash chromatography, eluting with EtOAc/Hexane (3:7) to furnish ethyl 7-((5-fluoropyridin-2-yl)(3-methyl-1,2,4-thiadiazol-5-yl)amino)heptanoate (4) as a yellow solid (0.22 g, 42%).

LCMS (ES): Found 368.7 [MH]+.

A fresh solution of NH₂OH in MeOH was prepared: [KOH (2.08 g, 30.05 mmol) in MeOH (15 mL) was added to NH₂OH.HCl (1.69 g, 30.05 mmol) in MeOH (15 mL) at 0° C.]. The mixture was stirred for 20 min at 0° C., then filtered to remove salts; the filtrate was then added to ethyl 7-((5-fluoropyridin-2-yl)(3-methyl-1,2,4-thiadiazol-5-yl)amino)heptanoate (4) (220 mg, 0.60 mmol) followed by KOH (337 mg, 6.5 mmol) solubilized in MeOH (5 mL). The reaction mixture was stirred at it for 21 h, then concentrated in vacuo, poured onto brine/H₂O (15 mL/35 mL), and extracted with CH₂Cl₂ (3×50 mL). The organic phases were combined, dried over Na₂SO₄, filtered and subsequently evaporated under vacuum. The resulting residue was purified by flash chromatography, eluting with MeOH/CH₂Cl₂ (1:9) to provide 7-((5-fluoropyridin-2-yl)(3-methyl-1,2,4-thiadiazol-5-yl)amino)-N-hydroxy heptanamide, Example CC, as an off-white solid (44 mg, 21%).

¹H NMR (400 MHz, DMSO-d₆) δ: 10.35 (br. s., 1H), 8.67 (s, 1H), 8.55 (d, J=3.0 Hz, 1H), 7.94 (ddd, J=9.2, 8.3, 3.0 Hz, 1H), 7.54 (dd, J=9.3, 3.3 Hz, 1H), 4.26-4.50 (m, 2H), 2.42 (s, 3H), 1.93 (t, J=7.3 Hz, 2H), 1.60-1.73 (m, 2H), 1.48 (dt, J=14.4, 7.4 Hz, 2H), 1.25-1.42 (m, 4H).

LCMS (ES): Found 354.0 [MH]+.

Example DD 8-((5-Fluoropyridin-2-yl)(3-methyl-1,2,4-thiadiazol-5-yl)amino)-N-hydroxyoctanamide

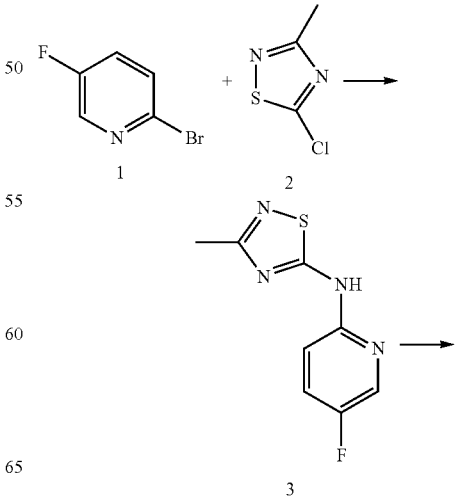

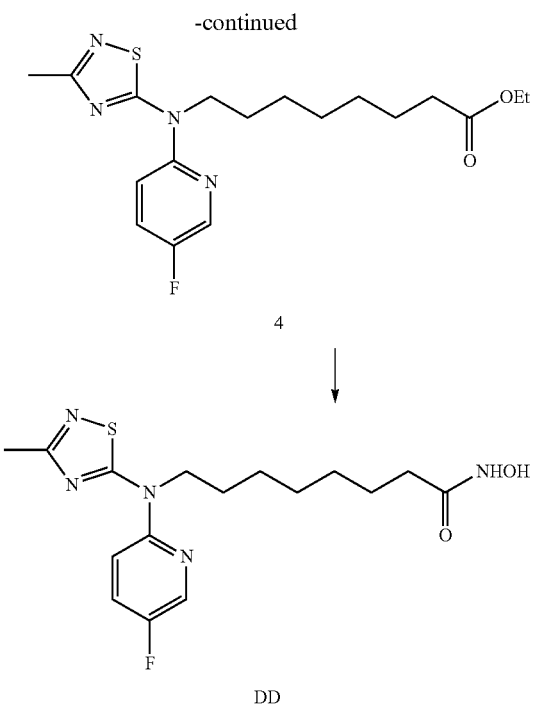

reaction mixture was stirred at it for 21 h, then concentrated in vacuo, poured onto brine/$H_2O$ (15 mL/35 mL), and extracted with $CH_2Cl_2$ (3×50 mL). The organic phases were combined, dried over $Na_2SO_4$, filtered and subsequently evaporated under vacuum. The resulting residue was purified by flash chromatography, eluting with MeOH/$CH_2Cl_2$ (1:9) to provide 8-((5-fluoropyridin-2-yl)(3-methyl-1,2,4-thiadiazol-5-yl)amino)-N-hydroxyoctanamide, Example DD, as a light brown solid (47 mg, 24%).

$^1$H NMR (400 MHz, DMSO-$d_6$) δ: 10.32 (s, 1H), 8.66 (s, 1H), 8.55 (d, J=2.9 Hz, 1H), 7.89-8.00 (m, 1H), 7.53 (dd, J=9.3, 3.3 Hz, 1H), 4.33-4.45 (m, 2H), 2.42 (s, 3H), 1.92 (t, J=7.2 Hz, 2H), 1.61-1.75 (m, 2H), 1.47 (dt, J=14.6, 7.3 Hz, 2H), 1.16-1.40 (m, 6H).

LCMS (ES): Found 368.0 [MH]+.

Example EE 7-((4-(4-Fluorophenyl)pyridin-2-yl)(3-methyl-1,2,4-thiadiazol-5-yl)amino)-N-hydroxyheptanamide

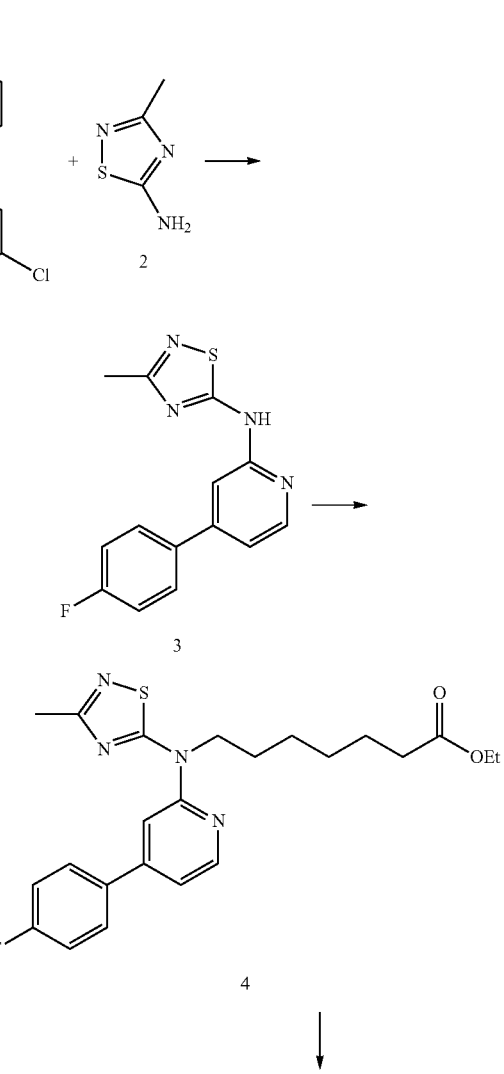

5-Fluoropyridin-2-amine (1) (1.0 g, 8.9 mmol), 5-chloro-3-methyl-1,2,4-thiadiazole (2) (1.19 g, 8.9 mmol), Xantphos (0.52 g, 0.89 mmol), and $Cs_2CO_3$ (4.35 g, 13.3 mmol) were combined in dry 1,4-dioxane (15 mL). The reaction mixture was degassed with $N_2$(g) and placed under vacuum for 10 min. $Pd_2(dba)_3$ (0.41 g, 0.44 mmol) was then added and the resulting reaction mixture was heated at 90° C. for 30 h. The reaction mixture was then poured onto demineralized water (200 mL), and extracted with EtOAc (3×100 mL). The organic phases were combined, dried over $Na_2SO_4$, filtered and subsequently evaporated under vacuum. The resulting residue was purified by flash chromatography eluting with EtOAc/Hexane (3:7) to provide N-(5-fluoropyridin-2-yl)-3-methyl-1,2,4-thiadiazol-5-amine (3) as a yellow solid (1.2 g, 67%).

LCMS (ES): Found 211.1 [MH]$^+$

NaH (60%) (59 mg, 1.49 mmol) was added portion-wise to N-(5-fluoropyridin-2-yl)-3-methyl-1,2,4-thiadiazol-5-amine (3) (300 mg, 1.42 mmol) in DMF (7 mL) at 5° C. under Ar(g). The reaction mixture was then stirred for 20 min, and ethyl-8-iodooctanoate (559 mg, 1.85 mmol) was added. The reaction mixture was stirred at 70° C. under Ar(g) for 1 h in the dark, then poured onto demineralized water (100 mL), extracted with EtOAc (3×50 mL). The organic phases were combined, dried over $Na_2SO_4$, filtered and subsequently evaporated under vacuum. The resulting residue was purified by flash chromatography, eluting with EtOAc/Hexane (3:7) to furnish ethyl 8-((5-fluoropyridin-2-yl)(3-methyl-1,2,4-thiadiazol-5-yl)amino)octanoate (4) as a yellow solid (200 mg, 37%).

LCMS (ES): Found 381.4 [MH]+.

A fresh solution of $NH_2OH$ in MeOH was prepared: [KOH (1.87 g, 27.32 mmol) in MeOH (12 mL) was added to $NH_2OH\cdot HCl$ (1.36 g, 19.50 mmol) in MeOH (12 mL) at 0° C.]. The mixture was stirred for 20 min at 0° C., then filtered to remove salts; the filtrate was then added to ethyl 8-((5-fluoropyridin-2-yl)(3-methyl-1,2,4-thiadiazol-5-yl)amino)octanoate (4) (200 mg, 0.54 mmol) followed by KOH (306 mg, 5.46 mmol) solubilized in MeOH (5 mL). The

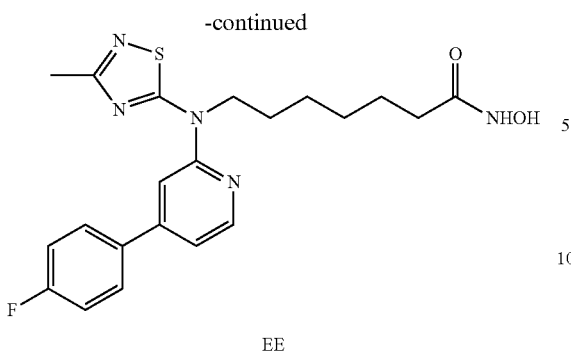

EE

2-Chloro-4-(4-fluorophenyl)pyridine (1) (1.0 g, 4.8 mmol), 3-methyl-1,2,4-thiadiazol-5-amine (2) (556 mg, 4.8 mmol), Xantphos (279 mg, 0.48 mmol), and Cs$_2$CO$_3$ (2.35 g, 7.24 mmol) were combined in dry 1,4-dioxane (15 mL). The reaction mixture was degassed with N$_2$(g) and placed under vacuum for 10 min. Pd$_2$(dba)$_3$ (0.22 g, 0.24 mmol) was then added and the resulting reaction mixture was heated at 90° C. for 30 h. It was then poured onto demineralized water (200 mL), and extracted with EtOAc (3×100 mL). The organic phases were combined, dried over Na$_2$SO$_4$, filtered and subsequently evaporated under vacuum. The resulting residue was purified by flash chromatography, eluting with EtOAc/Hexane (1:1) to provide N-(4-(4-fluorophenyl)pyridin-2-yl)-3-methyl-1,2,4-thiadiazol-5-amine, (3) as a yellow solid (1.1 g, 80%).

LCMS (ES): Found 287.1 [MH]+.

NaH (60%) (42 mg, 1.04 mmol) was added portion-wise to N-(4-(4-fluorophenyl)pyridin-2-yl)-3-methyl-1,2,4-thiadiazol-5-amine (3) (300 mg, 1.04 mmol) in DMF (7 mL) at 5° C. under Ar(g). The reaction mixture was then stirred for 20 min, and ethyl-7-iodoheptanoate (387 mg, 1.36 mmol) was added. The reaction mixture was stirred at 70° C. under Ar(g) for 1 h in the dark, then poured onto demineralized water (100 mL), and extracted with EtOAc (3×50 mL). The organic phases were combined, dried over Na$_2$SO$_4$, filtered and subsequently evaporated under vacuum. The resulting residue was purified by flash chromatography, eluting with EtOAc/Hexane (3:7) to furnish ethyl 7-((4-(4-fluorophenyl)pyridin-2-yl)(3-methyl-1,2,4-thiadiazol-5-yl)amino)heptanoate (4) as a yellow solid (237 mg, 54%).

LCMS (ES): Found 443.2 [MH]+.

A fresh solution of NH$_2$OH in MeOH was prepared: [KOH (1.50 g, 26.8 mmol) in MeOH (10 mL) was added to NH$_2$OH.HCl (1.86 g, 26.8 mmol) in MeOH (10 mL) at 0° C.]. The mixture was stirred for 20 min at 0° C., then filtered to remove salts; the filtrate was then added to ethyl 7-((4-(4-fluorophenyl)pyridin-2-yl)(3-methyl-1,2,4-thiadiazol-5-yl)amino)heptanoate (4) (237 mg, 0.57 mmol) followed by KOH (300 mg, 5.36 mmol) solubilized in MeOH (8 mL). The reaction mixture was stirred at rt for 21 h, then concentrated in vacuo, poured onto brine/H$_2$O (30 mL/70 mL), and extracted with CH$_2$Cl$_2$ (3×50 mL). The organic phases were combined, dried over Na$_2$SO$_4$, filtered and subsequently evaporated under vacuum. The resulting residue was purified by flash chromatography, eluting with MeOH/CH$_2$Cl$_2$ (1:9) to provide 7-((4-(4-fluorophenyl)pyridin-2-yl)(3-methyl-1,2,4-thiadiazol-5-yl)amino)-N-hydroxyheptanamide, Example EE, as light yellow solid (51 mg, 22%).

$^1$H NMR (400 MHz, DMSO-d$_5$) δ: 10.35 (br. s, 1H), 8.66 (s, 1H), 8.55 (d, J=5.3 Hz, 1H), 7.96 (dd, J=8.5, 5.5 Hz, 2H), 7.61 (s, 1H), 7.35-7.50 (m, 3H), 4.53 (t, J=7.0 Hz, 2H), 2.43 (s, 3H), 1.93 (t, J=7.3 Hz, 2H), 1.66-1.80 (m, 2H), 1.44-1.56 (m, 2H), 1.26-1.43 (m, 4H).

LCMS (ES): Found 430.2 [MH]+.

Example FF 8-((4-(4-Fluorophenyl)-pyridin-2-yl)(3-methyl-1,2,4-thiadiazol-5-yl)amino)-N-hydroxyoctanamide

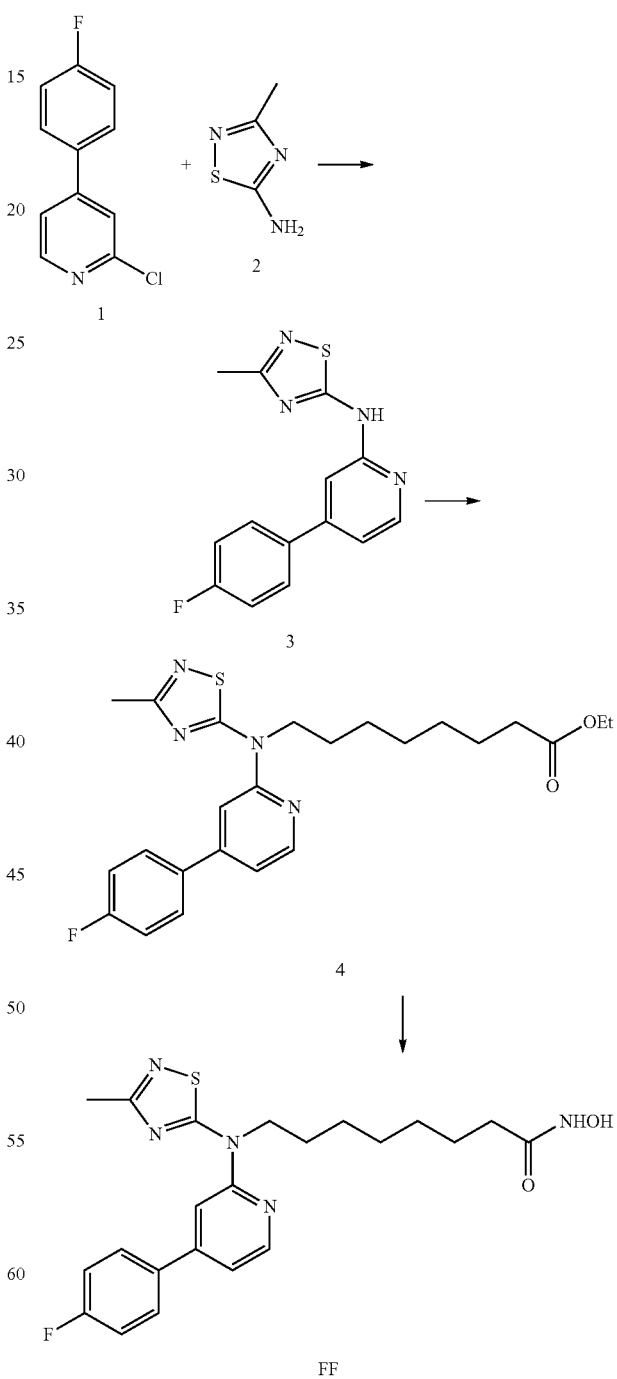

FF

NaH (60%) (42 mg, 1.05 mmol) was added portion-wise to N-(4-(4-fluorophenyl)pyridin-2-yl)-3-methyl-1,2,4-thiadiazol-5-amine (3) (as per Example EE above) (300 mg, 1.05 mmol) in DMF (8 mL) at 5° C. under Ar(g). The reaction mixture was then stirred for 20 min, and ethyl-8-iodooctanoate (406 mg, 1.36 mmol) was added. The reaction mixture was stirred at 70° C. under Ar(g) for 1 h in the dark, then poured onto demineralized water (100 mL), and extracted with EtOAc (3×50 mL). The organic phases were combined, dried over $Na_2SO_4$, filtered and subsequently evaporated under vacuum. The resulting residue was purified by flash chromatography, eluting with EtOAc/Hexane (3:7) to furnish ethyl 8-((4-(4-fluorophenyl)pyridin-2-yl)(3-methyl-1,2,4-thiadiazol-5-yl)amino)octanoate (4) as a light yellow solid (205 mg, 43%).

LCMS (ES): Found 457.2 [MH]+.

A fresh solution of $NH_2OH$ in MeOH was prepared: [KOH (1.25 g, 22.4 mmol) in MeOH (10 mL) was added to $NH_2OH \cdot HCl$ (1.55 g 22.4 mmol) in MeOH (10 mL) at 0° C.]. The mixture was stirred for 20 min at 0° C., then filtered to remove salts; the filtrate was then added to ethyl 8-((4-(4-fluorophenyl)pyridin-2-yl)(3-methyl-1,2,4-thiadiazol-5-yl)amino)octanoate (4) (205 mg, 0.44 mmol) followed by KOH (246 mg, 4.4 mmol) solubilized in MeOH (10 mL). The reaction mixture was stirred at it for 21 h, then concentrated in vacuo, poured onto brine/$H_2O$ (30 mL/70 mL), and extracted with $CH_2Cl_2$ (3×50 mL). The organic phases were combined, dried over $Na_2SO_4$, filtered and subsequently evaporated under vacuum. The resulting residue was purified by flash chromatography, eluting with MeOH/$CH_2Cl_2$ (1:9) to provide 8-((4-(4-fluorophenyl)pyridin-2-yl)(3-methyl-1,2,4-thiadiazol-5-yl)amino)-N-hydroxyoctanamide, Example FF, as a light yellow solid (45 mg, 22%).

$^1$H NMR (400 MHz, DMSO-$d_5$) δ: 10.32 (br. s, 1H), 8.65 (br. s, 1H), 8.55 (d, J=5.3 Hz, 1H), 7.96 (dd, J=8.9, 5.4 Hz, 2H), 7.61 (s, 1H), 7.46 (dd, J=5.4, 1.0 Hz, 1H), 7.41 (t, J=8.9 Hz, 2H), 4.54 (t, J=7.5 Hz, 2H), 2.43 (s, 3H), 1.91 (t, J=7.4 Hz, 2H), 1.67-1.80 (m, 2H), 1.47 (dt, J=14.7, 7.4 Hz, 2H), 1.28-1.42 (m, 4H), 1.18-1.27 (m, 2H).

LCMS (ES): Found 444.2 [MH]+.

Example GG 7-((5-Fluoropyridin-2-yl)(3-(trifluoromethyl)1,2,4-thiadiazol-5-yl)amino)-N-hydroxyheptanamide

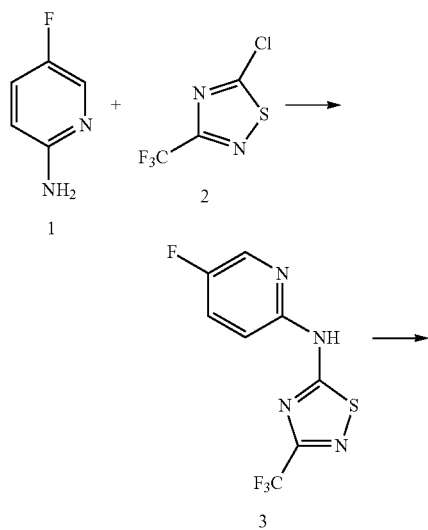

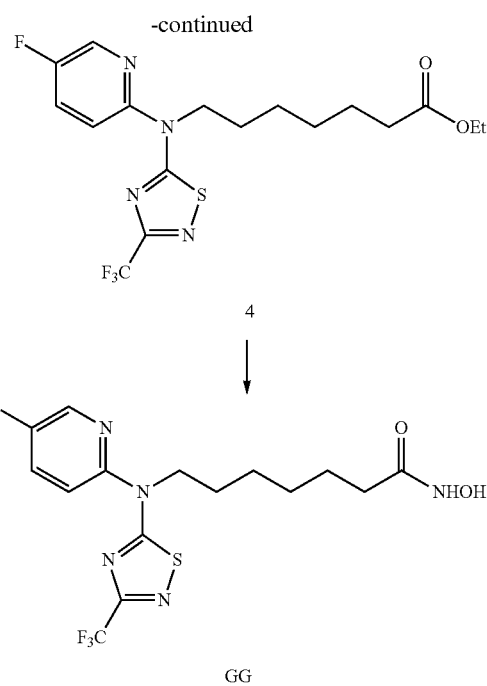

5-Fluoropyridin-2-amine (1) (1.0 g, 8.9 mmol), 5-chloro-3-(trifluoromethyl)1,2,4-thiadiazole (2) (1.68 g, 8.9 mmol), Xantphos (0.52 g, 0.89 mmol), and $Cs_2CO_3$ (4.35 g, 13.3 mmol) were combined in dry 1,4-dioxane (15 mL). The reaction mixture was degassed with $N_2(g)$ and placed under vacuum for 10 min. $Pd_2(dba)_3$ (0.41 g, 0.44 mmol) was then added and the resulting reaction mixture was heated at 90° C. for 30 h. It was then poured onto demineralized water (200 mL), and extracted with EtOAc (3×100 mL). The organic phases were combined, dried over $Na_2SO_4$, filtered and subsequently evaporated under vacuum. The resulting residue was purified by flash chromatography, eluting with EtOAc/Hexane (3:7) to provide N-(5-fluoropyridin-2-yl)-3-(trifluoromethyl)1,2,4-thiadiazol-5-amine (3) as a yellow solid (900 mg, 38%).

LCMS (ES): Found 265.1 [MH]+.

NaH (60%) (45 mg, 1.13 mmol) was added portion-wise to N-(5-fluoropyridin-2-yl)-3-(trifluoromethyl)-1,2,4-thiadiazol-5-amine (3) (300 mg, 1.13 mmol) in DM F (7 mL) at 5° C. under Ar(g). The reaction mixture was then stirred for 20 min, and ethyl-7-iodoheptanoate (419 mg, 1.47 mmol) was added. The reaction mixture was stirred at 70° C. under Ar(g) for 1 h in the dark, then poured onto demineralized water (100 mL), and extracted with EtOAc (3×50 mL). The organic phases were combined, dried over $Na_2SO_4$, filtered and subsequently evaporated under vacuum. The resulting residue was purified by flash chromatography, eluting with EtOAc/Hexane (3:7) to furnish ethyl 7-((5-fluoropyridin-2-yl)(3-methyl-1,2,4-thiadiazol-5-yl)amino)heptanoate (4) as a yellow solid (314 mg, 66%).

LCMS (ES): Found 421.4 [MH]+.

A fresh solution of $NH_2OH$ in MeOH was prepared: [KOH (2.09 g, 37.4 mmol) in MeOH (15 mL) was added to $NH_2OH \cdot HCl$ (2.60 g, 37.4 mmol) in MeOH (15 mL) at 0° C.]. The mixture was stirred for 20 min at 0° C., then filtered to remove salts; the filtrate was then added to ethyl 7-((5-fluoropyridin-2-yl)(3-(trifluoromethyl)1,2,4-thiadiazol-5-yl)amino)heptanoate (4) (314 mg, 0.74 mmol) followed by KOH (419 mg, 7.4 mmol) solubilized in MeOH (5 mL). The reaction mixture was stirred at it for 21 h, then concentrated in vacuo, poured into brine/H₂O (30 mL/70 mL), and extracted with CH₂Cl₂ (3×50 mL). The organic phases were combined, dried over Na₂SO₄, filtered and subsequently evaporated under vacuum. The resulting residue was purified by flash chromatography, eluting with MeOH/CH₂Cl₂ (1:9) to provide 7-((5-fluoropyridin-2-yl)(3-(trifluoromethyl)1,2,4-thiadiazol-5-yl)amino)-N-hydroxyheptanamide, Example GG, as a light orange solid (35 mg, 12%).

¹H NMR (400 MHz, DMSO-d₅) δ: 10.33 (br. s., 1H), 8.52-8.78 (m, 2H), 8.05 (t, J=7.7 Hz, 1H), 7.71 (d, J=8.9 Hz, 1H), 4.44 (t, J=6.5 Hz, 2H), 1.92 (t, J=7.0 Hz, 2H), 1.64-1.79 (m, 2H), 1.47 (dt, J=13.7, 7.1 Hz, 2H), 1.20-1.41 (m, 4H).

LCMS (ES): Found 408.4 [MH]+.

Example HH 8-((5-Fluoropyridin-2-yl)(3-(trifluoromethyl)1,2,4-thiadiazol-5-yl)amino)-N-hydroxyoctanamide

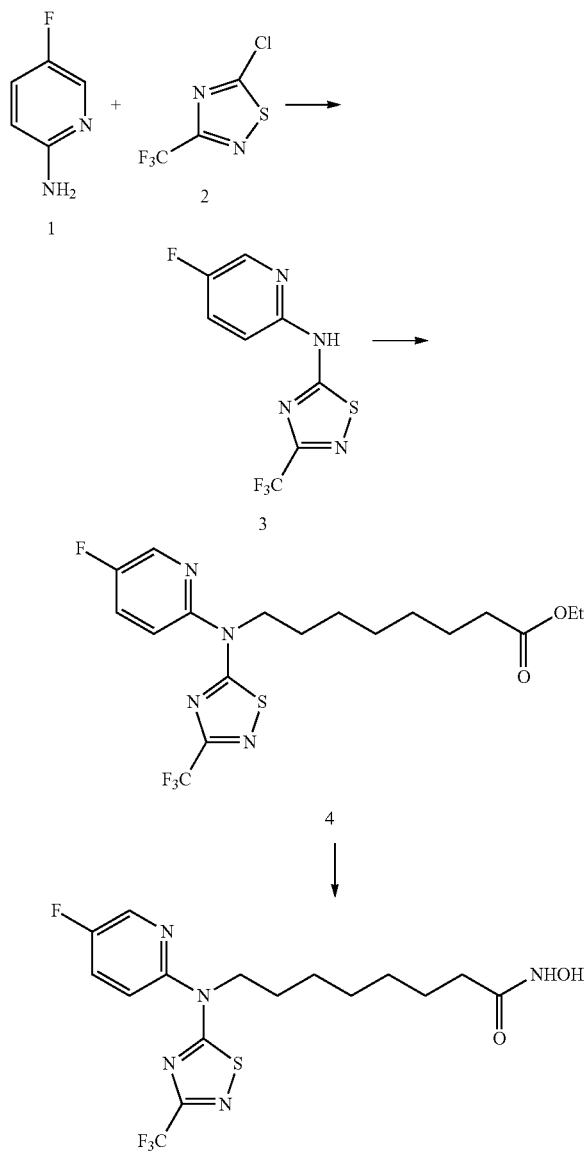

NaH (60%) (61 mg, 1.51 mmol) was added portion-wise to N-(5-fluoropyridin-2-yl)-3-(trifluoromethyl)1,2,4-thiadiazol-5-amine (3) (as per Example GG above) (400 mg, 1.51 mmol) in DMF (10 mL) at 5° C. under Ar(g). The reaction mixture was then stirred for 20 min, and ethyl-8-iodooctanoate (587 mg, 1.96 mmol) was added. The reaction mixture was stirred at 70° C. under Ar(g) for 1 h in the dark, then poured onto demineralized water (100 mL), extracted with EtOAc (3×50 mL). The organic phases were combined, dried over Na₂SO₄, filtered and subsequently evaporated under vacuum. The resulting residue was purified by flash chromatography, eluting with EtOAc/Hexane (3:7) to furnish ethyl 8-((5-fluoropyridin-2-yl)(3-(trifluoromethyl)1,2,4-thiadiazol-5-yl)amino)octanoate (4) as a yellow solid (580 mg, 85%).

LCMS (ES): Found 435.4 [MH]+.

A fresh solution of NH₂OH in MeOH was prepared: [KOH (3.74 g, 66.0 mmol) in MeOH (20 mL) was added to NH₂OH.HCl (4.61 g, 66.0 mmol) in MeOH (20 mL) at 0° C.]. The mixture was stirred for 20 min at 0° C., then filtered to remove salts; the filtrate was then added to ethyl 8-((5-fluoropyridin-2-yl)(3-(trifluoromethyl)1,2,4-thiadiazol-5-yl)amino)octanoate (4) (580 mg, 1.3 mmol) followed by KOH (748 mg, 13.0 mmol) solubilized in MeOH (10 mL). The reaction mixture was stirred at it for 21 h, then concentrated in vacuo, poured onto brine/H₂O (30 mL/70 mL), and extracted with CH₂Cl₂ (3×50 mL). The organic phases were combined, dried over Na₂SO₄, filtered and subsequently evaporated under vacuum. The resulting residue was purified by flash chromatography, eluting with MeOH/CH₂Cl₂ (1:9) to provide 8-((5-fluoropyridin-2-yl)(3-(trifluoromethyl)1,2,4-thiadiazol-5-yl)amino)-N-hydroxyoctanamide, Example HH, as an off-white solid (22 mg, 3.7%).

¹H NMR (400 MHz, DMSO-d₅) δ: 10.33 (br. s., 1H), 8.69 (d, J=2.9 Hz, 1H), 8.65 (br. s., 1H), 8.01-8.10 (m, 1H), 7.71 (dd, J=9.3, 3.2 Hz, 1H), 4.40-4.50 (m, 2H), 1.91 (t, J=7.4 Hz, 2H), 1.64-1.78 (m, 2H), 1.40-1.52 (m, 2H), 1.27-1.40 (m, 4H), 1.16-1.26 (m, 2H).

LCMS (ES): Found 422.4 [MH]+.

Example II 7-(Benzo[d]thiazol-2-yl(pyridin-2-yl)amino)-N-hydroxyheptanamide

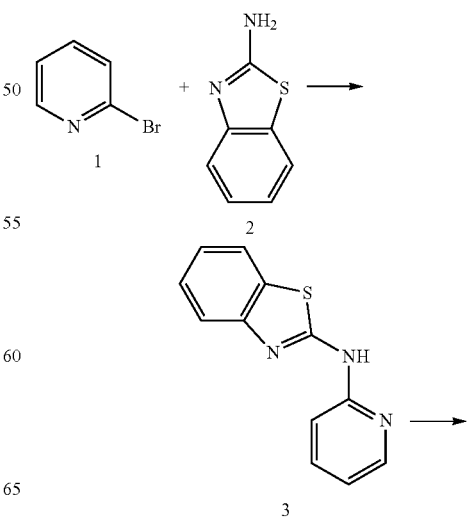

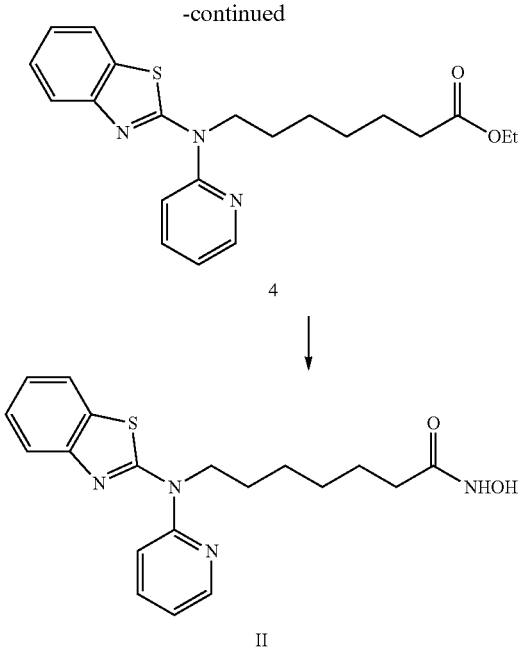

2-Bromopyridine (1) (1.0 g, 6.3 mmol), benzo[d]thiazol-2-amine (2) (0.974 g, 8.22 mmol), Xantphos (0.366 g, 0.63 mmol), and Cs$_2$CO$_3$ (3.09 g, 9.4 mmol) were combined in dry 1,4-dioxane (15 mL). The reaction mixture was degassed with N$_2$(g) and placed under vacuum for 10 min. Pd$_2$(dba)$_3$ (0.29 g, 0.31 mmol) was then added and the resulting reaction mixture was heated at 90° C. for 30 h. It was then poured onto demineralized water (200 mL), and extracted with EtOAc (3×100 mL). The organic phases were combined, dried over Na$_2$SO$_4$, filtered and subsequently evaporated under vacuum. The resulting residue was purified by flash chromatography, eluting with EtOAc/Hexane (1:1) to provide N-(pyridin-2-yl)benzo[d]thiazol-2-amine (3) as a yellow solid (0.86 g, 60%).

LCMS (ES): Found 228.1 [MH]+.

NaH (60%) (34 mg, 0.86 mmol) was added portion-wise to N-(pyridin-2-yl)benzo[d]thiazol-2-amine (3) (188 mg, 0.82 mmol) in DMF (5 mL) at 5° C. under Ar(g). The reaction mixture was then stirred for 20 min, and ethyl-7-iodoheptanoate (305 mg, 1.0 mmol) was added. The reaction mixture was stirred at 70° C. under Ar(g) for 1 h in the dark, then poured onto demineralized water (100 mL), and extracted with EtOAc (3×50 mL). The organic phases were combined, dried over Na$_2$SO$_4$, filtered and subsequently evaporated under vacuum. The resulting residue was purified by flash chromatography, eluting with EtOAc/Hexane (3:7) to furnish ethyl 7-(benzo[d]thiazol-2-yl(pyridin-2-yl)amino)heptanoate (4) as a yellow solid (106 mg, 34%).

LCMS (ES): Found 384.1 [MH]+.

A fresh solution of NH$_2$OH in MeOH was prepared: [KOH (774 mg, 13.8 mmol) in MeOH (10 mL) was added to NH$_2$OH.HCl (960 mg, 13.8 mmol) in MeOH (10 mL) at 0° C.]. The mixture was stirred for 20 min at 0° C., then filtered to remove salts; the filtrate was then added to ethyl 7-(benzo[d]thiazol-2-yl(pyridin-2-yl)amino)heptanoate (4) (106 mg, 0.27 mmol) followed by KOH (154 mg, 2.7 mmol) solubilized in MeOH (5 mL). The reaction mixture was stirred at rt for 21 h, then concentrated in vacuo, poured onto brine/H$_2$O (30 mL/70 mL), and extracted with CH$_2$Cl$_2$ (3×50 mL). The organic phases were combined, dried over Na$_2$SO$_4$, filtered and subsequently evaporated under vacuum. The resulting residue was purified by flash chromatography, eluting with MeOH/CH$_2$Cl$_2$ (1:9) to provide 7-(benzo[d]thiazol-2-yl(pyridin-2-yl)amino)-N-hydroxyheptanamide, Example II, as an off-white liquid (18 mg, 17%).

$^1$H NMR (400 MHz, METHANOL-d$_4$) δ: 8.42 (d, J=4.2 Hz, 1H), 7.82 (t, J=7.6 Hz, 1H), 7.62-7.75 (m, 2H), 7.34 (t, J=7.6 Hz, 1H), 7.29 (d, J=8.5 Hz, 1H), 7.18 (t, J=7.4 Hz, 1H), 7.07 (dd, J=6.8, 5.1 Hz, 1H), 4.28-4.46 (m, 2H), 2.09 (t, J=7.3 Hz, 2H), 1.80 (quin, J=7.3 Hz, 2H), 1.56-1.69 (m, 2H), 1.33-1.53 (m, 4H).

LCMS (ES): Found 371.1 [MH]+

Example JJ 8-(Benzo[d]thiazol-2-yl(pyridin-2-yl)amino)-N-hydroxyoctanamide

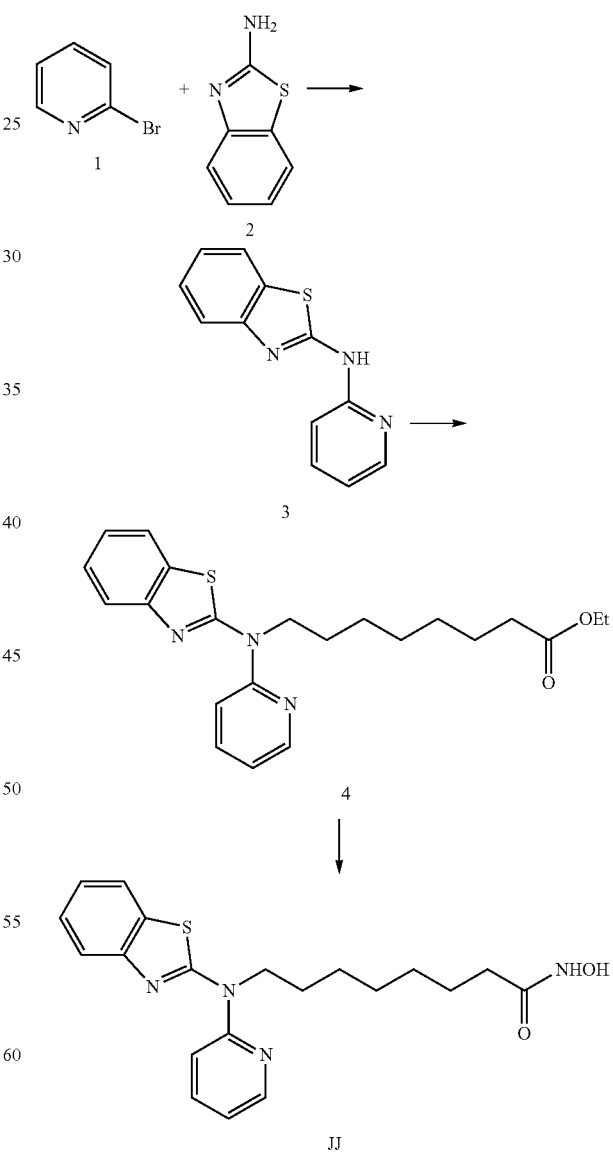

NaH (60%) (75 mg, 1.8 mmol) was added portion-wise to N-(pyridin-2-yl)benzo[d]thiazol-2-amine (3) (as per Example KK above) (430 mg, 1.8 mmol) in DMF (10 mL) at 5° C. under Ar(g). The reaction mixture was then stirred for 20 min, and ethyl-8-iodooctanoate (733 mg, 2.4 mmol) was added. The reaction mixture was stirred at 70° C. under Ar(g) for 1 h in the dark, then poured onto demineralized water (100 mL), and extracted with EtOAc (3×50 mL). The organic phases were combined, dried over $Na_2SO_4$, filtered and subsequently evaporated under vacuum. The resulting residue was purified by flash chromatography, eluting with EtOAc/Hexane (3:7) to furnish ethyl 8-(benzo[d]thiazol-2-yl(pyridin-2-yl)amino)octanoate (4) as a yellow solid (310 mg, 41%).

LCMS (ES): Found 398.1 [MH]+.

A fresh solution of $NH_2OH$ in MeOH was prepared: [KOH (2.18 g, 39.02 mmol) in MeOH (15 mL) was added to $NH_2OH.HCl$ (2.71 g, 39.02 mmol) in MeOH (15 mL) at 0° C. The mixture was stirred for 20 min at 0° C., then filtered to remove salts; the filtrate was then added to ethyl 8-(benzo[d]thiazol-2-yl(pyridin-2-yl)amino)octanoate (4) (310 mg, 0.78 mmol) followed by KOH (437 mg, 7.8 mmol) solubilized in MeOH (8 mL). The reaction mixture was stirred at it for 21 h, then concentrated in vacuo, poured onto brine/$H_2O$ (30 mL/70 mL), and extracted with $CH_2Cl_2$ (3×50 mL). The organic phases were combined, dried over $Na_2SO_4$, filtered and subsequently evaporated under vacuum. The resulting residue was purified by flash chromatography, eluting with MeOH/$CH_2Cl_2$ (1:9) to provide 8-(benzo[d]thiazol-2-yl(pyridin-2-yl)amino)-N-hydroxyoctanamide, Example JJ, as a yellow solid (43 mg, 14%).

$^1$H NMR (400 MHz, DMSO-$d_5$) δ: 10.33 (s, 1H), 8.66 (s, 1H), 8.47 (d, J=3.4 Hz, 1H), 7.89-7.96 (m, 1H), 7.87 (d, J=7.6 Hz, 1H), 7.68 (d, J=8.0 Hz, 1H), 7.41 (d, J=8.5 Hz, 1H), 7.37 (t, J=7.7 Hz, 1H), 7.21 (t, J=7.3 Hz, 1H), 7.15 (dd, J=7.1, 5.0 Hz, 1H), 4.38-4.51 (m, 2H), 1.93 (t, J=7.3 Hz, 2H), 1.65-1.81 (m, 2H), 1.49 (dt, J=14.6, 7.4 Hz, 2H), 1.30-1.43 (m, 4H), 1.18-1.29 (m, 2H).

LCMS (ES): Found 385.0 [MH]+.

Example KK

N-Hydroxy-7-(pyridin-2-yl(thiazol-2-yl)amino)heptanamide

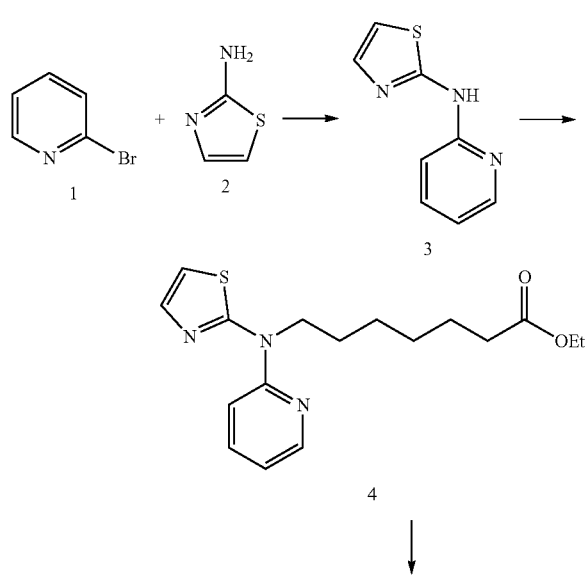

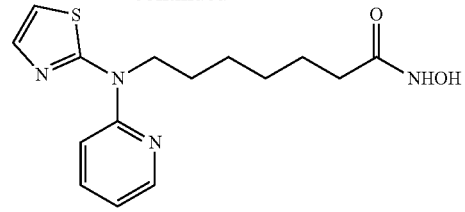

KK

2-Bromopyridine (1) (2.0 g, 12.6 mmol), thiazol-2-amine (2) (1.07 g, 10.7 mmol), Xantphos (0.732 g, 0.12 mmol), and $Cs_2CO_3$ (6.17 g, 18.9 mmol) were combined in dry 1,4-dioxane (15 mL). The reaction mixture was degassed with $N_2(g)$ and placed under vacuum for 10 min. $Pd_2(dba)_3$ (576 mg, 0.63 mmol) was then added and the resulting reaction mixture was heated at 90° C. for 30 h. It was then poured onto demineralized water (200 mL), and extracted with EtOAc (3×100 mL). The organic phases were combined, dried over $Na_2SO_4$, filtered and subsequently evaporated under vacuum. The resulting residue was purified by flash chromatography, eluting with EtOAc/Hexane (1:1) to provide N-(pyridin-2-yl)thiazol-2-amine (3) as a yellow solid (0.8 g, 35%).

LCMS (ES): Found 178.1 [MH]+.

NaH (60%) (45 mg, 1.12 mmol) was added portion-wise to N-(pyridin-2-yl)thiazol-2-amine (3) (200 mg, 1.12 mmol) in DMF (7 mL) at 5° C. under Ar(g). The reaction mixture was then stirred for 20 min, and ethyl-7-iodoheptanoate (417 mg, 1.46 mmol) was added. The reaction mixture was stirred at 70° C. under Ar(g) for 1 h in the dark, then poured onto demineralized water (100 mL), and extracted with EtOAc (3×50 mL). The organic phases were combined, dried over $Na_2SO_4$, filtered and subsequently evaporated under vacuum. The resulting residue was purified by flash chromatography, eluting with EtOAc/Hexane (3:7) to furnish ethyl 7-(pyridin-2-yl(thiazol-2-yl)amino)heptanoate (4) as a yellow solid (170 mg, 45%).

LCMS (ES): Found 334.1 [MH]+.

A fresh solution of $NH_2OH$ in MeOH was prepared: [KOH (1.43 g, 25.4 mmol) in MeOH (15 mL) was added to $NH_2OH.HCl$ (1.77 g, 25.4 mmol) in MeOH (15 mL) at 0° C.]. The mixture was stirred for 20 min at 0° C., then filtered to remove salts; the filtrate was then added to ethyl 7-(pyridin-2-yl(thiazol-2-yl)amino)heptanoate (4) (170 mg, 0.5 mmol) followed by KOH (286 mg, 5.0 mmol) solubilized in MeOH (8 mL). The reaction mixture was stirred at rt for 21 h, then concentrated in vacuo, poured onto brine/$H_2O$ (30 mL/70 mL), and extracted with $CH_2Cl_2$ (3×50 mL). The organic phases were combined, dried over $Na_2SO_4$, filtered and subsequently evaporated under vacuum. The resulting residue was purified by flash chromatography, eluting with MeOH/$CH_2Cl_2$ (1:9) to provide N-hydroxy-7-(pyridin-2-yl(thiazol-2-yl)amino)heptanamide, Example KK, as a light brown liquid (10 mg, 6%).

$^1$H NMR (400 MHz, METHANOL-$d_4$) δ: 8.38 (d, J=4.6 Hz, 1H), 7.73-7.84 (m, 1H), 7.40 (d, J=3.7 Hz, 1H), 7.21 (dd, J=8.5, 3.1 Hz, 1H), 6.95-7.03 (m, 1H), 6.92 (dd, J=3.7, 1.1 Hz, 1H), 4.26-4.37 (m, 2H), 2.09 (t, J=7.4 Hz, 2H), 1.70-1.83 (m, 2H), 1.63 (quin, J=7.2 Hz, 2H), 1.35-1.52 (m, 4H).

LCMS (ES): Found 321.1 [MH]+.

Example LL

N-Hydroxy-8-(pyridin-2-yl(thiazol-2-yl)amino)octanamide

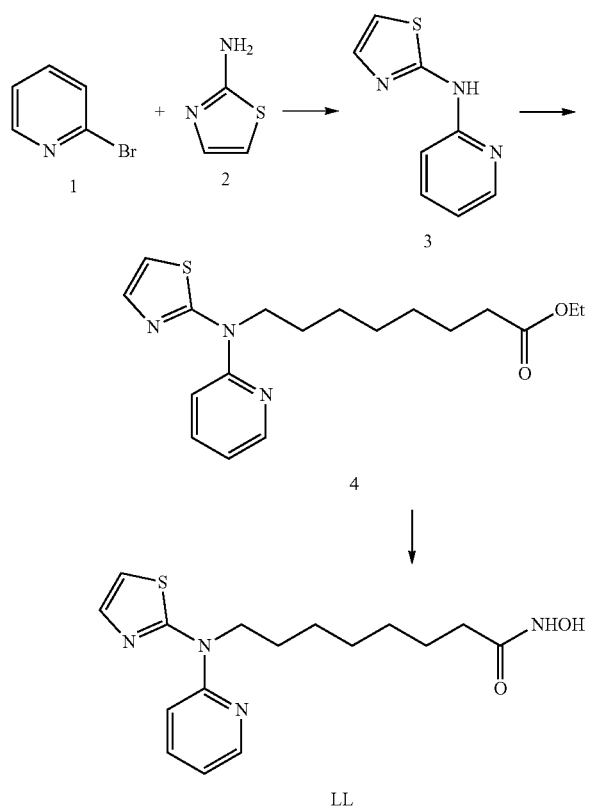

NaH (60%) (66 mg, 1.69 mmol) was added portion-wise to N-(pyridin-2-yl)thiazol-2-amine (3) (300 mg, 1.69 mmol) in DMF (8 mL) at 5° C. under Ar(g). The reaction mixture was then stirred for 20 min, and ethyl-8-iodooctanoate (654 mg, 2.20 mmol) was added. The reaction mixture was stirred at 70° C. under Ar(g) for 1 h in the dark, then poured onto demineralized water (100 mL), and extracted with EtOAc (3×50 mL). The organic phases were combined, dried over Na$_2$SO$_4$, filtered and subsequently evaporated under vacuum. The resulting residue was purified by flash chromatography, eluting with EtOAc/Hexane (3:7) to furnish ethyl 8-(pyridin-2-yl(thiazol-2-yl)amino)octanoate (4) as a yellow solid (180 mg, 30%).

LCMS (ES): Found 348.1 [MH]$^+$

A fresh solution of NH$_2$OH in MeOH was prepared: [KOH (1.42 g, 52.8 mmol) in MeOH (20 mL) was added to NH$_2$OH.HCl (1.75 g, 25.2 mmol) in MeOH (20 mL) at 0° C.]. The mixture was stirred for 20 min at 0° C., then filtered to remove salts; the filtrate was then added to ethyl 8-(pyridin-2-yl(thiazol-2-yl)amino)octanoate (4) (175 mg, 0.5 mmol) followed by KOH (283 mg, 5.04 mmol) solubilized in MeOH (10 mL). The reaction mixture was stirred at rt for 21 h, then concentrated in vacuo, poured onto brine/H$_2$O (30 mL/70 mL), and extracted with CH$_2$Cl$_2$ (3×50 mL). The organic phases were combined, dried over Na$_2$SO$_4$, filtered and subsequently evaporated under vacuum. The resulting residue was purified by flash chromatography, eluting with MeOH/CH$_2$Cl$_2$ (1:9) to provide N-hydroxy-8-(pyridin-2-yl(thiazol-2-yl)amino)octanamide, Example LL, as a light brown solid (65 mg, 38%).

$^1$H NMR (400 MHz, DMSO-d$_5$) δ: 10.33 (s, 1H), 8.66 (br. s., 1H), 8.40 (d, J=3.8 Hz, 1H), 7.77-7.91 (m, 1H), 7.46 (d, J=3.7 Hz, 1H), 7.28 (d, J=8.6 Hz, 1H), 6.99-7.08 (m, 2H), 4.29-4.38 (m, 2H), 1.93 (t, J=7.3 Hz, 2H), 1.60-1.73 (m, 2H), 1.48 (quin, J=7.2 Hz, 2H), 1.28-1.41 (m, 4H), 1.16-1.27 (m, 2H).

LCMS (ES): Found 335.7 [MH]+.

Biochemical Data

Compounds of the invention may be tested for HDAC inhibitory activity by any suitable assay, e.g. the assay described in WO2008/062201. By this assay, the following data were obtained:

In Vitro Biochemical Data

| Example | IC$_{50}$, HDAC1 | IC$_{50}$, HDAC6 |
|---|---|---|
| A | * (226.5 nM) | * (1.76 nM) |
| B | * | * |
| C | * | * |
| D | *** | * |
| E | * | * |
| F | *** | * |
| G | * | * |
| H | *** | * |
| I | ** | * |
| J | *** | * |
| K | * | * |
| L | **** | * |
| M | *** | * |
| N | *** | * |
| O | ** | * |
| P | *** | * |
| Q | **** | * |
| R | *** | * |
| S | ** | * |
| T | *** | * |
| U | *** | * |
| V | **** | * |
| W | *** | * |
| X | *** | * |
| Y | * | * |
| Z | **** | * |
| AA | *** | * |
| BB | **** | * |
| CC | ** | * |
| DD | *** | * |
| EE | *** | * |
| FF | *** | * |
| GG | ** | * |
| HH | *** | * |
| II | *** | * |
| JJ | *** | * |
| KK | *** | * |
| LL | *** | * |

Key:
**** ≥10 uM
*** ≤10 uM ≥1 uM
** ≤1 uM ≥500 nM
* ≤500 nM

In Vitro Cancer Cell Growth Inhibition Data for Compound a

| IC$_{50}$ (µM), A549 | IC$_{50}$ (µM), PC-3 |
|---|---|
| 1.89 | 2.32 |

Comparative Mouse Pharmacokinetic Data for Example a and Example 3 of WO 2010/086646

When comparing compounds of the present invention with Examples in WO 2010/086646, it has been shown that compounds of the invention have increased bioavailability (data below for mice).

Example A

Oral bioavailability, F % = 19

Example 3 of WO/2010/86646

F % = 2

The invention claimed is:

1. A compound of the formula wherein:
  is a single bond and X is N; and
wherein:
  n is 3 to 7;
  R is H;
  each R' is independently selected from H and $QR_1$;
  each Q is independently selected from the group consisting of a bond, CO, $CO_2$, NH, S, SO, $SO_2$ and O;
  each $R_1$ is independently selected from the group consisting of H, $C_1$-$C_{10}$ alkyl, $C_2$-$C_{10}$ alkenyl, $C_2$-$C_{10}$ alkynyl, aryl, heteroaryl, $C_1$-$C_{10}$ cycloalkyl, halogen, $C_1$-$C_{10}$ alkylaryl, $C_1$-$C_{10}$ alkyl heteroaryl, $C_1$-$C_{10}$ heterocycloalkyl and trifluoromethyl;
  L is selected from the group consisting of thiazolyl, imidazolyl, oxazolyl, pyrazolyl, thiadiazolyl and oxadiazolyl, each of which is optionally fused to a benzene;
  Y is pyridyl;
  W is

NHOH:

wherein for each occurrence, aryl or heteroaryl may be substituted by up to five substituents, each of which is selected from the group consisting of $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis($C_1$-$C_3$ alkyl) amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl; and
  each alkyl, alkenyl or alkynyl may be optionally substituted with a substituent selected from the group consisting of aryl, $C_3$-$C_{10}$ cycloalkyl, heteroaryl, halogen, $NH_2$, $NO_2$ and hydroxyl;
  or a pharmaceutically acceptable salt thereof.

2. The compound according to claim 1, wherein in at least one of L and Y, the atom that is directly bonded to X is a carbon, and at least one nitrogen atom is directly bonded to said carbon.

3. The compound according to claim 1, wherein at least one R' is selected from the group consisting of H, $C_1$-$C_{10}$ alkyl, O—($C_1$-$C_{10}$ alkyl) and halogen, wherein the alkyl is optionally substituted with at least one fluorine.

4. The compound according to claim 1, wherein at least one R' is optionally substituted aryl or O-(optionally substituted aryl), wherein the optional substituents are defined in claim 1.

5. The compound according to claim 4, wherein the aryl is substituted with at least one halogen.

6. The compound according to claim 1, wherein n is 5 to 7.

7. The compound according to claim 1, wherein the compound is selected from the group consisting of:
  N-hydroxy-7-[(3-methyl-1,2,4-thiadiazol-5-yl)(pyridin-2-yl)amino]heptanamide;
  N-hydroxy-7-[(3-methyl-1,2,4-thiadiazol-5-yl)(pyridin-3-yl)amino]heptanamide;
  N-hydroxy-7-((3-methyl-1,2,4-oxadiazol-5-yl)(pyridin-2-yl)amino)heptanamide;
  N-hydroxy-8-((3-methyl-1,2,4-oxadiazol-5-yl)(pyridin-2-yl)amino)octanamide;
  N-hydroxy-7-((1-methyl-1H-pyrazol-3-yl)(pyridin-2-yl)amino)heptanamide;
  N-hydroxy-8-((1-methyl-1H-pyrazol-3-yl)(pyridin-2-yl)amino)octanamide;
  N-hydroxy-7-(pyridin-2-yl(1,3,4-thiadiazol-2-yl)amino)heptanamide;
  N-hydroxy-8-(pyridin-2-yl(1,3,4-thiadiazol-2-yl)amino)octanamide;
  N-hydroxy-7-((5-methyl-1,3,4-thiadiazol-2-yl)(pyridin-2-yl)amino)heptanamide;
  N-hydroxy-8-((5-methyl-1,3,4-thiadiazol-2-yl)(pyridin-2-yl)amino)octanamide;

7-(benzo[d]oxazol-2-yl(pyridin-2-yl)amino)-N-hydroxyheptanamide;

8-(benzo[d]oxazol-2-yl(pyridin-2-yl)amino)-N-hydroxyoctanamide;

N-hydroxy-7-((4-methyl-1H-benzo[d]imidazol-2-yl)(pyridin-2-yl)amino)heptanamide;

N-hydroxy-8-((4-methyl-1H-benzo[d]imidazol-2-yl)(pyridin-2-yl)amino)octanamide;

N-hydroxy-7-(pyridin-2-yl(1,2,4-thiadiazol-5-yl)amino)heptanamide;

N-hydroxy-8-(pyridin-2-yl(1,2,4-thiadiazol-5-yl)amino)octanamide;

7-((5-fluoropyridin-2-yl)(3-methyl-1,2,4-oxadiazol-5-yl)amino)-N-hydroxyheptanamide;

8-((5-fluoropyridin-2-yl)(3-methyl-1,2,4-oxadiazol-5-yl)amino)-N-hydroxyoctanamide;

7-((5-fluoropyridin-2-yl)(1-methyl-1H-benzo[d]imidazol-2-yl)amino)-N-hydroxyheptanamide;

8-((5-fluoropyridin-2-yl)(1-methyl-1H-benzo[d]imidazol-2-yl)amino)-N-hydroxyoctanamide;

7-((5-fluoropyridin-2-yl)(1-methyl-1H-pyrazol-3-yl)amino)-N-hydroxyheptanamide;

8-((5-fluoropyridin-2-yl)(1-methyl-1H-pyrazol-3-yl)amino)-N-hydroxyoctanamide;

7-(benzo[d]oxazol-2-yl(5-fluoropyridin-2-yl)amino)-N-hydroxyheptanamide;

8-(benzo[d]oxazol-2-yl(5-fluoropyridin-2-yl)amino)-N-hydroxyoctanamide;

7-((4-(4-fluorophenyl)pyridin-2-yl)(1-methyl-1H-pyrazol-3-yl)amino)-N-hydroxyheptanamide;

8-((4-(4-fluorophenyl)pyridin-2-yl)(1-methyl-1H-pyrazol-3-yl)amino)-N-hydroxy octanamide;

7-((5-fluoropyridin-2-yl)(3-(trifluoromethyl)1,2,4-thiadiazol-5-yl)amino)-N-hydroxyheptanamide;

8-((5-fluoropyridin-2-yl)(3-(trifluoromethyl)1,2,4-thiadiazol-5-yl)amino)-N-hydroxyoctanamide;

7-((5-fluoropyridin-2-yl)(3-methyl-1,2,4-thiadiazol-5-yl)amino)-N-hydroxyheptanamide;

8-((5-fluoropyridin-2-yl)(3-methyl-1,2,4-thiadiazol-5-yl)amino)-N-hydroxyoctanamide;

7-((4-(4-fluorophenyl)pyridin-2-yl)(3-methyl-1,2,4-thiadiazol-5-yl)amino)-N-hydroxyheptanamide;

8-((4-(4-fluorophenyl)-pyridin-2-yl)(3-methyl-1,2,4-thiadiazol-5-yl)amino)-N-hydroxyoctanamide;

7-((5-fluoropyridin-2-yl)(3-(trifluoromethyl)1,2,4-thiadiazol-5-yl)amino)-N-hydroxyheptanamide;

8-((5-fluoropyridin-2-yl)(3-(trifluoromethyl)1,2,4-thiadiazol-5-yl)amino)-N-hydroxyoctanamide;

7-(benzo[d]thiazol-2-yl(pyridin-2-yl)amino)-N-hydroxyheptanamide;

8-(benzo[d]thiazol-2-yl(pyridin-2-yl)amino)-N-hydroxyoctanamide;

N-hydroxy-7-(pyridin-2-yl(thiazol-2-yl)amino)heptanamide; and

N-hydroxy-8-(pyridin-2-yl(thiazol-2-yl)amino)octanamide, or a pharmaceutically acceptable salt thereof.

8. A pharmaceutical composition comprising the compound according to claim 1, and a pharmaceutically acceptable carrier or diluent.

* * * * *